US008333964B2

(12) United States Patent
Agus

(10) Patent No.: US 8,333,964 B2
(45) Date of Patent: Dec. 18, 2012

(54) ERBB ANTAGONISTS FOR PAIN THERAPY

(75) Inventor: David B. Agus, Beverly Hills, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 12/955,693

(22) Filed: Nov. 29, 2010

(65) Prior Publication Data

US 2011/0064737 A1    Mar. 17, 2011

Related U.S. Application Data

(63) Continuation of application No. 11/102,120, filed on Apr. 7, 2005, now abandoned.

(60) Provisional application No. 60/561,076, filed on Apr. 8, 2004.

(51) Int. Cl.
*A61K 39/395* (2006.01)
*C07K 16/28* (2006.01)

(52) U.S. Cl. ............... 424/130.1; 424/133.1; 424/135.1; 424/141.1; 424/143.1; 530/387.1; 530/387.9; 530/388.22

(58) Field of Classification Search .................. None
See application file for complete search history.

(56) References Cited

U.S. PATENT DOCUMENTS

| | | | |
|---|---|---|---|
| 4,968,603 | A | 11/1990 | Slamon et al. |
| 5,183,884 | A | 2/1993 | Kraus et al. |
| 5,480,968 | A | 1/1996 | Kraus et al. |
| 5,641,869 | A | 6/1997 | Vandlen et al. |
| 5,677,171 | A | 10/1997 | Hudziak et al. |
| 5,821,337 | A | 10/1998 | Carter et al. |
| 5,824,311 | A | 10/1998 | Greene et al. |
| 7,041,292 | B1 | 5/2006 | Sliwkowski |
| 2002/0002276 | A1 | 1/2002 | Fitzpatrick et al. |

FOREIGN PATENT DOCUMENTS

| | | |
|---|---|---|
| EP | 599274 | 11/1993 |
| WO | WO 94/00136 | 1/1994 |
| WO | WO 94/22478 | 10/1997 |
| WO | WO 01/00238 A1 | 1/2001 |
| WO | WO 2004/048525 | 6/2004 |

OTHER PUBLICATIONS

Goblirsch et al. (2006). Biology of Bone Cancer Pain. Clin. Cancer Res. 12(20 Suppl):6231s-6235s.*
Aasland, et al., "Expression of Oncogenes in Thyroid Tumours: Coexpression of *c-erbB2/neu* and *c-erbB*", British Journal of Cancer, vol. 57, pp. 358-363, 1988.
Arteaga, et al., "p185$^{n,b13-2}$Signaling enhances Cisplatin-Induced Cytotoxicity in Human Breast Carcinoma Cells: Association between an Oncogenic Receptor Tyrosine Kinase and Drug-Induced DNA Repair", Cancer Research, vol. 54, pp. 3758-3765, 1994.
Bacus et al., "Tumor-Inhibitory Monoclonal Antibodies to the HER-2/Neu Receptor Induce Differentiation of Human Breast Cancer Cells", Cancer Research, vol. 52, pp. 2580-2589, 1992.

Bacus, et al., "Differentiation of Cultured Human Breast Cancer Cells (AU-565 and MCF-7) Associated with Loss of Cell Surface HER-2/neu Antigen", Molecular Carcinogenesis, vol. 3, pp. 350-362, 1990.
Baselga et al., "Phase II Study of Weekly Intravenous Recombinant Humanized Anti-p185$^{HER2}$ Monoclonal Antibody in Patients with HER2/neu-Overexpressing Metastatic Breast Cancer", Journal of Clinical Oncology, vol. 14, No. 3, pp. 737-744, 1996.
Baselga, et al., "Receptor Blockade with Monoclonal Antibodies as Anti-Cancer Therapy", Pharmac. Ther., vol. 64, pp. 127-154, 1994.
Bass et al., :A Note on an Improved Method of Analgetic Evaluation, J. American Pharm. Assoc. Sci. Ed., vol. 41, No. 10, pp. 569-570, 1952.
Bennett, et al., "A Peripheral Mononeuropathy in Rat that Produces Disorders of Pain Sensation like those seen in Man", Pain, vol. 33, pp. 87-107, 1988.
Borst, et al., "Oncogene Alterations in Endometrial Carcinoma" Gynecologic Oncology, vol. 38, pp. 364366, 1990.
Bos et al., "A Target for Phosphoinositide 3-Kinase: Akt/PKB", TIBS, vol. 20, pp. 441-442, 1995.
Carraway et al., "Heregulin Stimulates Mitogenesis and Phosphatidylinositol 3-Kinase in Mouse Fibroblasts Transfected with erbB2/neu and erbB3", The Journal of Biological Chemistry, vol. 270, No. 13, pp. 7111-7116, 1995.
Carraway et al., "Neuregulin-2, a New Ligand of ErbB3/ErbB4-Receptor Tyrosine Kinases", Nature, vol. 387, pp. 512-516, 1997.
Carraway, et al., "A Neu Acquaintance for ErbB3 and ErbB4: A Role for Receptor Heterodimerization in Growth Signaling", Cell, vol. 78, pp. 5-8, 1994.
Chang et al., "Ligands for ErbB-Family Receptors Encoded by a Neuregulin-like Gene", Nature, vol. 387, pp. 509-512, 1997.
Cohen et al., "Expression Pattern of the *Neu* (NGL) Gene-Coded Growth Factor Receptor Protein (p185') in Normal and Transformed Epithelial Tissues of the Digestive Tract", Oncogene, vol. 4, pp. 81-88, 1989.
D. Souza, et al., "Overexpression of ERBB2 in Human Mammary Epithelial Cells Signals Inhibition of Transcription of the E-Cadherin Gene", Proc. Natl. Acad. Sci USA, vol. 91, pp. 7202-7206, 1994.
DiRosa et al., "Studies of the Mediators of the Acute Inflammatory Response Induced in Rats in Different Sites by Carrageenan and Turpentine", J. Pathol., vol. 104, pp. 15-29, 1971.
Drebin et al., "Down-Modulation of an Oncogene Protein Product and Reversion of the Transformed Phenotype by Monoclonal Antibodies", Cell, vol. 41, pp. 695-706, 1985.
Drebin et al., "Monoclonal Antibodies Reactive with Distinct Domains of the *Neu* Oncogene-Encoded p185 Molecule Exert Synergistic Anti-Tumor Effects in Vivo", Oncogene, vol. 2, pp. 273-277, 1988.
Dubinsky, et al., "The Antialgesic Drugs: Human Therapeutic Correlates of the Their Potency in Laboratory Animal Models of Hyperalgesia", Agent Actions, vol. 20, pp. 50-60, 1987.
Earp et al., "Heterodimerization and Functional Interaction Between EGF Receptor Family Members: A New Signaling Paradigm with Implications for Breast Cancer Research", Breast Cancer Research and Treatment, vol. 35, pp. 115-132, 1995.

(Continued)

*Primary Examiner* — Christine J Saoud
*Assistant Examiner* — Jon M Lockard
(74) *Attorney, Agent, or Firm* — Wendy Lee; Ginger R. Dreger; Arnold & Porter LLP

(57) ABSTRACT

The present application describes the use of ErbB antagonist, especially ErbB2 antibodies such as rhuMAb 2C4, for treating pain.

46 Claims, 13 Drawing Sheets

OTHER PUBLICATIONS

Fendley et al., "Characterization of Murine Monoclonal Antibodies Reactive to Either the Human Epidermal Growth Factor Receptor or HER2/neu Gene Product", Cancer Research, vol. 50, pp. 1550-1558, 1990.

Fukushige et al., "Localization of a Novel v-erbB-Related Gene, c-erbB-2, on Human Chromosome 17 and Its Amplification on a Gastric Cancer Cell Line", Molecular and Cellure Biology, vol. 6, No. 3, pp. 955-958, 1986.

Green et al., "A Comparison of Heat and Pressure Analgesiometric Methods in Rats", Brit. J. Pharmacol., vol. 6, pp. 572-585, 1951.

Groenen et al., "Structure-Function Relationships for the EGF/TGF-a Family of Mitogens", Growth Factors, vol. 11, pp. 235-257, 1994.

Gu et al., "Overexpression of her-2/neu in Human Prostate Cancer and Benign Hyperplasia", Cancer Letters, vol. 99, pp. 185-189, 1996.

Guerin et al., "Overexpression of Either c-myc or c-erbB-2/neu Proto-Oncogenes in Human Breast Carcinomas: Correlation with Poor Prognosis", Oncogen Research, vol. 3, pp. 21-31, 1988.

Guilerme et al., "Neurotrophin-4 Mediated TrkB Activation Reinforces Morphine-Induced Analgesia", Nature Neuroscience, vol. 6. No. 3, pp. 221-222, 2003.

Hancock et al., "A Monoclonal Antibody Against the c-erbB-2 Protein Enhances the Cytotoxicity of cisDiamminedichloroplatinum against Human Breast and Ovarian Tumor Cell Lines", Cancer Research, vol. 51, pp. 4575-4580, 1991.

Harari et al., "Neuregulin-4: A Novel Growth Factor that Acts Through the ErbB-4 Receptor Tyrosine Kinase", Oncogene, vol. 18, pp. 2681-2689, 1999.

Harwerth et al., "Monoclonal Antibodies Against the Extracellular Domain of the erbB-2 Receptor Function as Partial Ligand Agonists", The Journal of Biological Chemistry, vol. 267, No. 21, pp. 15160-15167, 1992.

Heiss et al., "Immunotherapy of Malignant Ascites with Trifunctional Antibodies", Intl. J. Cancer, vol. 117, pp. 435-443, 2005.

Holmes et al., "Identification of Heregulin, A Specific Activator of $p185^{th82}$", Science, vol. 256, pp. 12051210, 1992.

Hudziak et al., "$p185^{HER2}$ Monoclonal Antibody has Antiproliferative Effects in Vitro and Sensitizes Human Breast Tumor Cells to Tumor Necrosis Factor", Molecular and Cellular Biology, vol. 9, No. 3, pp. 1165-1172, 1989.

James et al., "A Phase II Study of the Bispecific Antibody MDX-H210 (anti-HER2×CD64) with GM-CSF in HER2+ Advanced Prostate Cancer", British Journal of Cancer, vol. 85, No. 2, pp. 152-156, 2001.

Jones et al., "Binding Interaction of the Heregulini3 egf Domain with ErbB3 and ErbB4 Receptors Assessed by Alanine Scanning Mutagenesis", The Journal of Biological Chemistry vol. 273, No. 19, pp. 11667-16674, 1998.

Karunagaran et al., "ErbB-2 is a Common Auxiliary Subunit of NDF and EGF Receptors: Implications for Breast Cancer", EMBO Journal, vol. 15, No. 2, pp. 254-264, 1996.

Kasprzyk et al., "Therapy of an Animal Model of Human Gastric Cancer Using a Combination of AntierbB-2 Monoclonal Antobodies", Cancer Research, vol. 52, pp. 2771-2776, 1992.

Kern et al., "p185"'Expression in Human Lung Adenocarcinomas Predicts Shortened Survival", Cancer Research, vol. 50, pp. 5184-5191, 1990.

King et al., "Amplification of a Novel v-erbB-Related Gene in a Human Mammary Carcinoma", Science, vol. 229, pp. 974-976, 1985.

Klapper et al., "A Subclass of Tumor-Inhibitory Monoclonal Antibodies to ErbB-2/HER2 Blocks Crosstalk with Growth Factor Receptors", Oncogene, vol. 14, pp. 2099-2109, 1997.

Kotts et al., "Differential Growth Inhibition of Human Carcinoma Cells Exposed to Minoclonal Antibodies Directed Against the Extracellular Domain of the HER2/ERBB2 Protooncoogene" In Vitro, vol. 26, No. 3, pp. 59A, 1990.

Kraus et al., "Isolation and Characterization of ERBB3, a third member of the ERBB/Epidermal Growth Factor Receptor Family: Evidence for the Overexpression in a Subset of Human Mammary Tumors", Proc. Natl. Acad. Sci. USA, vol. 86, pp. 9193-9197, 1989.

Krymskaya et al., "EGF Activates ErbB-2 and Stimulates Phosphatidylinositol 3-Kinas in Human Airway Smooth Muscle Cells", The American Physiological Society, vol. 276, pp. L246-255, 1999.

Kumar et al., "Regulation of Phosphorylation of the c-erbB-2/HER2 Gene Product by a Monoclonal Antibody and Serum Growth Factor(s) in Human Mammary Carcinoma Cells", Molecular and Cellular Biology, vol. 11, No. 2, pp. 979-986, 1991.

Lariviere et al., "The Bee Venom Test: A New Tonic-Pain Test", Pain, vol. 66, pp. 271-277, 1996.

Lee et al., "Transforming Growth Factor a: Expression, Regulation, and Biological Activities", Pharmacological Reviews, vol. 47, No. 1, pp. 51-85, 1995.

Lemke et al., "Neuregulins in Development", Molecular and Cellular Neuroscience, vol. 7, pp. 247-262, 1996.

Levi et al., "The Influence of Heregulins on Human Schwann Cell Proliferation", The Journal of Neuroscience, vol. 15, No. 2, pp. 1329-1340, 1995.

Lewis et al., "Differential Response of Human Tumor Cell Lines to Anti-$p185^{HER2}$ Monoclonal Antibodies", Cancer Immunology Immunotherapy, vol. 37, pp. 255-263, 1993.

Lewis et al., "Growth Regulation of Human Breast and Ovarian Tumor Cells by Heregulin: Evidence for the Requirement of ErbB2 as a Critical Component in Mediating Heregulin Responsiveness", Cancer research, vol. 56,pp. 1457-1465, 1996.

Maier et al., Requrienments for the Internalization of a Murine Monoclonal Antibody Directed Against the HER-2/neu Gene Product c-erbB-2, Cancer Research, vol. 51, pp. 5361-5369, 1991.

Mary Eaton, Ph.D., "Common Animal Models for Spasticity and Pain", Journal of Rehabilitation Research and Development, vol. 40, No. 4, pp. 41-54, 2003.

Masui et al., Growth Inhibition of Human Tumor Cells in Athymic Mice by Anti-Epidermal Growth Factor Receptor Monoclonal Antibodies, Cancer Research 44, pp. 1002-1007, 1984.

McCann et al., "c-erbB-2 Oncoprotein Expression in Primary Human Tumors", Cancer, vol. 65, pp. 88-92, 1990.

McKenzie et al., "Generation and Characterization of Monoclonal Antibodies Specific for the Human Neu Oncogene Product, p185", Oncogene, vol. 4, pp. 543-548, 1989.

Menendez et al., "Initial Thermal Heat Hypoalgesia in a Murine Model of Bone Cancer Pain", Brain Research, vol. 969, pp. 102-109, 2003.

Miller, George A., "The Magical Number SeVen, Plus or Minus Two: Some Limits on our Capacity for Processing Information", The Psychological Review, vol. 63, No. 2, pp. 81-97, 1956.

Morrissey et al., "Axon-induced Mitogenesis of Human Schwann Cell Involves Heregulin and $p185^{ba2}$", Proc. Natl. Acad. Sci USA, vol. 92, pp. 1431-14235, 1995.

Myers et al., "Biological Effects of Monoclonal Antireceptor Antibodies Reactive with Neu Oncogene Product, $p185^{c'e}$" Methods in Enzymology, vol. 198, pp. 277-290, 1991.

O'Callaghan et al., "Quantification of the Analgesic Activity of Narcotic Antagonists by a Modified Hot-Plate Procedure$^{1,2,3}$", Journal of Pharmacology and Experimental Therapeutics, vol. 192, No. 3, pp. 497-505, 1975.

Olayioye et al., "ErbB-1 and•ErbB-2 Acquire Distinct Signaling Properties Dependent upon their Dimerization Partner", Molecular and Cellular Biology, vol. 18, No. 9, pp. 5042-5051, 1998.

Park et al., "Amplification, Overexpression, and Rearrangement of the erbB-2 Protooncogene in Primary Human Stomach Carcinomas", Cancer Research, vol. 49, pp. 6605-6609, 1989.

Pietras et al., "Antibody to HER-2/neu Receptor Blocks DNA Repair after Cisplatin in Human Breast and Ovarian Cancer Cells", Oncogene, vol. 9, pp. 1829-1838, 1994.

Plowman et al., "Heregulin Induces Tyrosine Phosphorylation of HER4/$p180er^{bB4}$", Nature, vol. 366, pp. 473-475, 1993.

Plowman et al., "Ligand-Specific Activation of HER4/$p180^{crbB4}$, a fourth member of the Epidermal Growth Factor Receptor Family", Proc. Natl. Acad. Sci. USA, vol. 90, pp. 1746-1750, 1993.

Ritesh et al., "Activated T Cells Armed with Anti-CD3×Anti-HER2/neu Bispecifie Antibody III. Kinetics and Survival of Armed ATC in Prostate Cancer Patients", Blood, vol. 100, No. 11 (Abstract No. 3684), 2002.

Ross et al., "HER-2/neu Gene Amplification Status on Prostate Cancer by Fluorescence in Situ Hybridization", Hum. Pathol., vol. 28, pp. 827-833, 1997.

Ross et al., "Prognostic Significance of HER-2/neu Gene Amplification Status by Fluorescence in Situ Hybridization of Prostate Carcinoma", American Cancer Society, vol. 79, pp. 2162-2170, 1997.

Sadasivan et al., "Overexpression of HER-2/neu may be an Indicator of Poor Prognosis in Prostate Cancer", The Journal of Urology, vol. 150, pp. 126-131, 1993.

Sarup et al., "Characterization of an Anti-p185$^{HER2}$ Monoclonal Antibody that Stimulates Receptor Function and Inhibits Tumor Cell Growth", Growth Regulation, vol. 1, pp. 72-82, 1991.

Schaefer et al., "A Discrete Three-Amino Acid Segment (LVI) at the C-Terminal End of Kinase-Impaired ErbB3 is Required for Transactivation of ErbB2", The Journal of Biological Chemistry, vol. 274, No. 2, pp. 859-866, 1999.

Schaefer et al., "y-Heregulin: aANovel Heregulin Isoform that is an Autocrine Growth Factor for the Human Breast Cancer Cell Line, MDA-B-175", Oncogene, vol. 15, pp. 1385-1394, 1997.

Scott, et al., "p185$^{HER2}$ Signal Transduction in Breast Cancer Cells", The Journal of Biological Chemistry, vol. 266, No. 22, pp. 14300-14305, 1991.

Shawyer, et al., "Ligand-like Effects Induced by Anti-c-erbB-2 Antibodies Do Not Correlate with and Are Not Required for Growth Inhibition if Human Carcinoma Cells", Cancer Research, vol. 54, pp. 1367-1373, 1994.

Shepard et al., "Monoclonal Antibody Therapy of Human Cancer: Taking the HER2 Protooncogene to the Clinic", Journal of Clinical Immunology, vol. 11, No. 3, pp. 117-126, 1991.

Shimoyama et al., "A Mouse Model of Neuropathic Cancer Pain", Pain, vol. 99, pp. 167-174, 2002.

Slamon et al., "Human Breast Cancer: Correlation of Relapse and Survival with Amplification of the HER2/neu Oncogene", Science, vol. 235, pp. 177-182, 1987.

Slamon et al., "Studies of the Her-2/neu Proto-oncogene in Human Breast and Ovarian Cancer", Science, vol. 244, pp. 707-712, 1989.

Sliwkowski et al., "Coexpression of erbB2 and erbB3 Proteins Reconstitutes a High Affinity Receptor for Heregulin", The Journal of Biological Chemistry, vol. 269, No. 20, pp. 14461-14665, 1994.

Stancovski et al., "Mechanistic Aspects of the Opposing Effects of Monoclonal Antibodies to the ERBB2 Receptor on Tumor Growth", Proc. Natl., Acad. Sci USA, vol. 88, pp. 8691-8695, 1991.

Sumikura et al., "Spatial and Temporal Profiles of Flare and Hyperalgesia after Intradermal Capsaicin", Pain. vol. 105, pp. 285-291, 2003.

Tagliabue et al., "Selection of Monoclonal Antibodies which Induce Internalization and Phosphorylation of p185$^{HER2}$ and Growth Inhibition of Cells with HER2/NEU Gene Amplification", Int. J. Cancer, vol. 47, pp. 933-937, 1991.

Takahasi et al., "Metastatic Braest Cancer of HER2 Scored 2+ by IHC and HER2 Gene Amplifacation Assayed by FISH has a Good Response to Single Agent Therapy with Trastuzumab: A Case Report", Breast Cancer, vol. 10, No. 2, pp. 170-174, 2003.

Tan et al., "Geregulin BI-Activated Phosphatidylinositol 3-Kinase Enhances Aggregation of MCF-7 Breast Cancer Cells Independent of Extracellular Signal-Regulated Kinase", Cancer Research, vol. 59, pp. 16201625, 1999.

Turk et al., "Core Outcome Domains for Chronic Pain Clinical Trails: Immpact Recommendations", Pain, vol. 106, pp. 337-345, 2003.

Vitetta, et al., "Monoclonal Antibodies as Agonists: An Expanded Role for Their Use in Cancer Therapy", Cancer Research, vol. 54, pp. 5301-5309, 1994.

Wacnik et al., "Tumor Implantation in Mouse Humerus Evoks Movement-Related Hyperalgesia Exceeding that Evoked by Intramuscular Carregeenan", Pain, vol. 101, pp. 175-186, 2003.

Weiner et al., "Expression of the *neu* Gene-encoded Protein (P185')  in Human Non-Small Cell Carcinomas of the Lung", Cancer Research, vol. 50, pp. 421-425, 1990.

Williams et al., "Expression of c-erbB-2 in Human Pancreatic Adenocarcinomas", Pathobiology, vol. 59, pp. 46-52, 1991.

Wu et al., "Apoptosis Induced by an Anti-Epidermal Growth Factor Receptor Monoclonal Antibody in a Human Colorectal Carcinoma Cell Line and its Delay by Insulin", J. Clin. Invest., vol. 95, pp. 1897-1905, 1995.

Xiong et al., "Cetuximab, A Monoclonal Antibody Targeting the Epidermal Growth Factor Receptor, in Combination with Gemcitabine for Advanced Pancreatic Cancer: A Multicenter Phase II Trial", Journal of Clinical Oncology, vol. 22, No. 13, pp. 2610-2616, 2004.

Xu et al., "Antibody-induced Growth Inhibition is Mediated through Immunochemically and Functionally Distinct Epitopes on the Extracellular Domain of the *c-erbB-2* (HER-2/neu) Gene Product p185", Int. J. Cancer, vol. 53, pp. 501-408, 1993.

Yokota et al., "Amplification of *c-erbB-2* Oncogene in Human Adenocarcinomas In Vivo", The Lancet, vol. 1, pp. 765-767, 1986.

Yonemura et al., "Evaluation of Immunoreactivity for erbB-2 Protein as a Marker of Poor Short Term Prognosis in Gastric Cancer", Cancer Research, vol. 51, pp. 1034-1038, 1991.

Zhang et al., "Neuregulin-3 (NRG3): A Novel Neural Tissue-Enriched Protein that Binds and Activates ErbB4", Proc. Natl. Acad. Sci. USA, vol. 94, pp. 9562-9567, 1997.

Zhau et al., "Amplification and Expression of the c-erb B-2/neu Proto-Oncogene in Human Bladder Cancer", Molecular Carcinogensis, vol. 3, pp. 254-257, 1990.

* cited by examiner (SEQ ID NO: 13)

FIG. 1A

```
        VARIABLE LIGHT
                 10        20        30        40
2C4     DIVMTQSHKIMSTSVGDRVSITC [KASQDVSIGVA] WYQQRP
        **    ****  *         *
574     DIQMTQSPSSLSASVGDRVTITC [KASQDVSIGVA] WYQQKP
                                   *  ** ***
hum κI  DIQMTQSPSSLSASVGDRVTITC [RASQSISNYLA] WYQQKP 50        60        70        80
2C4     GQSPKLLIY [SASYRYT] GVPDRFTGSGSGTDFTFTISSVQA
          **                   *  *          *   * *
574     GKAPKLLIY [SASYRYT] GVPSRFSGSGSGTDFTLTISSLQP
          * ******
hum κI  GKAPKLLIY [AASSLES] GVPSRFSGSGSGTDFTLTISSLQP 90        100
2C4     EDLAVYYC [QQYYIYPYT] FGGGTKLEIK (SEQ ID NO:1)
          * *                      *   *
574     EDFATYYC [QQYYIYPYT] FGQGTKVEIK (SEQ ID NO:3)
                    ***  *
hum κI  EDFATYYC [QQYNSLPWT] FGQGTKVEIK (SEQ ID NO:5)
```

FIG. 7A

```
        VARIABLE HEAVY
                 10        20        30        40
2C4     EVQLQQSGPELVKPGTSVKISCKAS [GFTFTDYTMD] WVKQS
           **  **  *   * ***  *                 * *
574     EVQLVESGGGLVQPGGSLRLSCAAS [GFTFTDYTMD] WVRQA
                                      ***   *
hum III EVQLVESGGGLVQPGGSLRLSCAAS [GFTFSSYAMS] WVRQA 50    a   60             70        80
2C4     HGKSLEWIG [DVNPNSGGSIYNQRFKG] KASLTVDRSSRIVYM
         *  **                        ***   ****  *
574     PGKGLEWVA [DVNPNSGGSIYNQRFKG] RFTLSVDRSKNTLYL
        * ******  ***  ****              * *
hum III PGKGLEWVA [VISGDGGSTYYADSVKG] RFTISRDNSKNTLYL abc   90         100ab         110
2C4     ELRSLTFEDTAVYYCAR [NLGPSFYFDY] WGQGTTLTVSS (SEQ ID NO:2)
         ***  *                          **
574     QMNSLRAEDTAVYYCAR [NLGPSFYFDY] WGQGTLVTVSS (SEQ ID NO:4)
                                ********
hum III QMNSLRAEDTAVYYCAR [GRVGYSLYDY] WGQGTLVTVSS (SEQ ID NO:6)
```

FIG. 7B

SEQUENCE LISTING

```
<160> NUMBER OF SEQ ID NOS: 13

<210> SEQ ID NO 1
<211> LENGTH: 107
<212> TYPE: PRT
<213> ORGANISM: Artificial Sequence
<220> FEATURE:
```

-continued

<223> OTHER INFORMATION: Murine monoclonal antibody 2C4 (variable light)

<400> SEQUENCE: 1

Asp Thr Val Met Thr Gln Ser His Lys Ile Met Ser Thr Ser Val Gly
1               5                   10                  15

Asp Arg Val Ser Ile Thr Cys Lys Ala Ser Gln Asp Val Ser Ile Gly
            20                  25                  30

Val Ala Trp Tyr Gln Gln Arg Pro Gly Gln Ser Pro Lys Leu Leu Ile
        35                  40                  45

Tyr Ser Ala Ser Tyr Arg Tyr Thr Gly Val Pro Asp Arg Phe Thr Gly
50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln Tyr Tyr Ile Tyr Pro Tyr
                85                  90                  95

Thr Phe Gly Gly Gly Thr Lys Leu Glu Ile Lys
            100                 105

<210> SEQ ID NO 2
<211> LENGTH: 119
<212> TYPE: PRT
<213> ORGANISM: Artificial Sequence
<220> FEATURE:
<223> OTHER INFORMATION: Murine monoclonal antibody 2C4 (variable heavy)

<400> SEQUENCE: 2

Glu Val Gln Leu Gln Gln Ser Gly Pro Glu Leu Val Lys Pro Gly Thr
1               5                   10                  15

Ser Val Lys Ile Ser Cys Lys Ala Ser Gly Phe Thr Phe Thr Asp Tyr
            20                  25                  30

Thr Met Asp Trp Val Lys Gln Ser His Gly Lys Ser Leu Glu Trp Ile
        35                  40                  45

Gly Asp Val Asn Pro Asn Ser Gly Gly Ser Ile Tyr Asn Gln Arg Phe
50                  55                  60

Lys Gly Lys Ala Ser Leu Thr Val Asp Arg Ser Ser Arg Ile Val Tyr
65                  70                  75                  80

Met Glu Leu Arg Ser Leu Thr Phe Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Thr Leu Thr Val Ser Ser
        115

<210> SEQ ID NO 3
<211> LENGTH: 107
<212> TYPE: PRT
<213> ORGANISM: Artificial Sequence
<220> FEATURE:
<223> OTHER INFORMATION: Humanized monoclonal antibody 2C4 version 574
      (variable light)

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly

```
                50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ile Tyr Pro Tyr
                    85                  90                  95

Thr Phe Gly Gln Gly Thr Lys Val Glu Ile Lys
                100                 105

<210> SEQ ID NO 4
<211> LENGTH: 119
<212> TYPE: PRT
<213> ORGANISM: Artificial Sequence
<220> FEATURE:
<223> OTHER INFORMATION: Humanized monoclonal antibody 2C4 version 574
      (variable heavy)

<400> SEQUENCE: 4

Glu Val Gln Leu Val Glu Ser Gly Gly Leu Val Gln Pro Gly Gly
 1               5                  10                  15

Ser Leu Arg Leu Ser Cys Ala Ala Ser Gly Phe Thr Phe Thr Asp Tyr
                20                  25                  30

Thr Met Asp Trp Val Arg Gln Ala Pro Gly Lys Gly Leu Glu Trp Val
                35                  40                  45

Ala Asp Val Asn Pro Asn Ser Gly Gly Ser Ile Tyr Asn Gln Arg Phe
 50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
                100                 105                 110

Thr Leu Val Thr Val Ser Ser
        115

<210> SEQ ID NO 5
<211> LENGTH: 107
<212> TYPE: PRT
<213> ORGANISM: Artificial Sequence
<220> FEATURE:
<223> OTHER INFORMATION: Consensus human framework for the humanized
      antibody hum kI (variable light)

<400> SEQUENCE: 5

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Asn Tyr
                20                  25                  30

Leu Ala Trp Tyr Gln Gln Lys Pro Gly Lys Ala Pro Lys Leu Leu Ile
                35                  40                  45

Tyr Ala Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Leu Pro Trp
                85                  90                  95

Thr Phe Gly Gln Gly Thr Lys Val Glu Ile Lys
                100                 105

<210> SEQ ID NO 6
```

```
<211> LENGTH: 119
<212> TYPE: PRT
<213> ORGANISM: Artificial Sequence
<220> FEATURE:
<223> OTHER INFORMATION: Consensus human framework for the humanized
      antibody hum III (variable heavy)

<400> SEQUENCE: 6

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Val Ile Ser Gly Asp Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Val Gly Tyr Ser Leu Tyr Asp Tyr Trp Gly Gln Gly
            100                 105                 110

Thr Leu Val Thr Val Ser Ser
        115

<210> SEQ ID NO 7
<211> LENGTH: 10
<212> TYPE: PRT
<213> ORGANISM: Artificial Sequence
<220> FEATURE:
<223> OTHER INFORMATION: humanized anitbody (variable heavy)
<221> NAME/KEY: UNSURE
<222> LOCATION: 10
<223> OTHER INFORMATION: X= Asp or Ser

<400> SEQUENCE: 7

Gly Phe Thr Phe Thr Asp Tyr Thr Met Xaa
 1               5                  10

<210> SEQ ID NO 8
<211> LENGTH: 17
<212> TYPE: PRT
<213> ORGANISM: Artificial Sequence
<220> FEATURE:
<223> OTHER INFORMATION: humanized anitbody (variable heavy)

<400> SEQUENCE: 8

Asp Val Asn Pro Asn Ser Gly Gly Ser Ile Tyr Asn Gln Arg Phe Lys
 1               5                  10                  15

Gly

<210> SEQ ID NO 9
<211> LENGTH: 10
<212> TYPE: PRT
<213> ORGANISM: Artificial Sequence
<220> FEATURE:
<223> OTHER INFORMATION: humanized anitbody (variable heavy)

<400> SEQUENCE: 9

Asn Leu Gly Pro Ser Phe Tyr Phe Asp Tyr
 1               5                  10

<210> SEQ ID NO 10
<211> LENGTH: 11
```

```
<212> TYPE: PRT
<213> ORGANISM: Artificial Sequence
<220> FEATURE:
<223> OTHER INFORMATION: humanized anitbody (variable light)

<400> SEQUENCE: 10

Lys Ala Ser Gln Asp Val Ser Ile Gly Val Ala
 1               5                  10

<210> SEQ ID NO 11
<211> LENGTH: 7
<212> TYPE: PRT
<213> ORGANISM: Artificial Sequence
<220> FEATURE:
<223> OTHER INFORMATION: humanized anitbody (variable light)
<221> NAME/KEY: UNSURE
<222> LOCATION: 5
<223> OTHER INFORMATION: X=Arg or Leu
<221> NAME/KEY: UNSURE
<222> LOCATION: 6
<223> OTHER INFORMATION: X=Tyr or Glu
<221> NAME/KEY: UNSURE
<222> LOCATION: 7
<223> OTHER INFORMATION: X=Thr or Ser

<400> SEQUENCE: 11

Ser Ala Ser Tyr Xaa Xaa Xaa
 1               5

<210> SEQ ID NO 12
<211> LENGTH: 9
<212> TYPE: PRT
<213> ORGANISM: Artificial Sequence
<220> FEATURE:
<223> OTHER INFORMATION: humanized anitbody (variable light)

<400> SEQUENCE: 12

Gln Gln Tyr Tyr Ile Tyr Pro Tyr Thr
 1               5

<210> SEQ ID NO 13
<211> LENGTH: 525
<212> TYPE: PRT
<213> ORGANISM: homo sapiens

<400> SEQUENCE: 13

Met Glu Leu Ala Ala Leu Cys Arg Trp Gly Leu Leu Leu Ala Leu Leu
 1               5                  10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
         35                  40                  45

Leu Tyr Gln Gly Cys Gln Val Val Gln Gly Asn Leu Glu Leu Thr Tyr
     50                  55                  60

Leu Pro Thr Asn Ala Ser Leu Ser Phe Leu Gln Asp Ile Gln Glu Val
 65                  70                  75                  80

Ile Val Arg Gly Thr Gln Leu Phe Glu Asp Asn Tyr Ala Leu Ala Val
                85                  90                  95

Leu Asp Asn Gly Asp Pro Leu Asn Asn Thr Thr Pro Val Thr Gly Ala
            100                 105                 110

Ser Pro Gly Gly Leu Arg Glu Leu Gln Leu Arg Ser Leu Thr Glu Ile
        115                 120                 125

Leu Lys Gly Gly Val Leu Ile Gln Arg Asn Pro Gln Leu Cys Tyr Gln
    130                 135                 140
```

-continued

```
Asp Thr Ile Leu Trp Lys Asp Ile Phe His Lys Asn Asn Gln Leu Ala
145                 150                 155                 160

Gly Ser Arg Cys Trp Gly Glu Ser Ser Glu Asp Cys Gln Ser Leu Thr
                165                 170                 175

Arg Thr Val Cys Ala Gly Gly Cys Ala Arg Cys Lys Gly Pro Leu Pro
            180                 185                 190

Thr Asp Cys Cys His Glu Gln Cys Ala Ala Gly Cys Thr Gly Pro Lys
        195                 200                 205

His Ser Asp Cys Leu Ala Cys Leu His Phe Asn His Ser Gly Ile Cys
    210                 215                 220

Glu Leu His Cys Pro Ala Leu Val Thr Tyr Asn Thr Asp Thr Phe Glu
225                 230                 235                 240

Tyr Asn Tyr Leu Ser Thr Asp Val Gly Ser Cys Thr Leu Val Cys Pro
                245                 250                 255

Leu His Asn Gln Glu Val Thr Ala Glu Asp Gly Thr Gln Arg Cys Glu
            260                 265                 270

Lys Cys Ser Lys Pro Cys Ala Arg Val Cys Tyr Gly Leu Gly Met Glu
        275                 280                 285

His Leu Arg Glu Val Arg Ala Val Thr Ser Ala Asn Ile Gln Glu Phe
    290                 295                 300

Ala Gly Cys Lys Lys Ile Phe Gly Ser Leu Ala Phe Leu Pro Glu Ser
305                 310                 315                 320

Glu Thr Leu Glu Glu Ile Thr Gly Tyr Leu Tyr Ile Ser Ala Trp Pro
                325                 330                 335

Asp Ser Leu Pro Asp Leu Ser Val Phe Gln Asn Leu Gln Val Ile Arg
            340                 345                 350

Gly Arg Ile Leu His Asn Gly Ala Tyr Ser Leu Thr Leu Gln Gly Leu
        355                 360                 365

Gly Ile Ser Trp Leu Gly Leu Arg Ser Leu Arg Glu Leu Gly Ser Gly
    370                 375                 380

Leu Ala Leu Ile His His Asn Thr His Leu Cys Phe Val His Thr Val
385                 390                 395                 400

Glu Asp Glu Cys Val Gly Glu Gly Leu Ala Cys His Gln Leu Cys Ala
                405                 410                 415

Arg Gly His Cys Trp Gly Pro Gly Pro Thr Gln Cys Val Asn Cys Ser
            420                 425                 430

Gln Phe Leu Arg Gly Gln Glu Cys Val Glu Glu Cys Arg Val Leu Gln
        435                 440                 445

Gly Leu Pro Arg Glu Tyr Val Asn Ala Arg His Cys Leu Pro Cys His
    450                 455                 460

Pro Glu Cys Gln Pro Gln Asn Gly Ser Val Thr Cys Phe Gly Pro Glu
465                 470                 475                 480

Pro Ser Gly Val Lys Pro Asp Leu Ser Tyr Met Pro Ile Trp Lys Phe
                485                 490                 495

Pro Asp Glu Glu Gly Ala Cys Gln Pro Cys Pro Ile Asn Cys Thr His
            500                 505                 510

Ser Cys Val Asp Leu Asp Asp Lys Gly Cys Pro Ala Glu
        515                 520                 525
```

ERBB ANTAGONISTS FOR PAIN THERAPY

CROSS-REFERENCE TO RELATED APPLICATIONS

This application is a continuation application of U.S. patent application Ser. No. 11/102,120, filed Apr. 7, 2005, now abandoned which claims priority under 35 U.S.C. Section 119(e) and the benefit of U.S. Provisional Application Ser. No. 60/561,076, filed on Apr. 8, 2004, the contents of which are incorporated herein by reference in their entireties.

FIELD OF THE INVENTION

The present invention concerns ErbB antagonists for treating pain.

BACKGROUND OF THE INVENTION

Anti-ErbB Antibodies and their Use in Cancer Treatment

The ErbB family of receptor tyrosine kinases are important mediators of cell growth, differentiation and survival. The receptor family includes four distinct members including epidermal growth factor receptor (EGFR or ErbB1), HER2 (ErbB2 or p185$^{neu}$), HER3 (ErbB3) and HER4 (ErbB4 or tyro2).

EGFR, encoded by the erbB1 gene, has been causally implicated in human malignancy. In particular, increased expression of EGFR has been observed in breast, bladder, lung, head, neck and stomach cancer as well as glioblastomas. Increased EGFR receptor expression is often associated with increased production of the EGFR ligand, transforming growth factor alpha (TGF-α), by the same tumor cells resulting in receptor activation by an autocrine stimulatory pathway. Baselga and Mendelsohn *Pharmac. Ther.* 64:127-154 (1994). Monoclonal antibodies directed against the EGFR or its ligands, TGF-α and EGF, have been evaluated as therapeutic agents in the treatment of such malignancies. See, e.g., Baselga and Mendelsohn., supra; Masui et al. *Cancer Research* 44:1002-1007 (1984); and Wu et al. *J. Clin. Invest.* 95:1897-1905 (1995).

The second member of the ErbB family, p185$^{neu}$, was originally identified as the product of the transforming gene from neuroblastomas of chemically treated rats. The activated form of the neu proto-oncogene results from a point mutation (valine to glutamic acid) in the transmembrane region of the encoded protein. Amplification of the human homolog of neu is observed in breast and ovarian cancers and correlates with a poor prognosis (Slamon et al., *Science*, 235:177-182 (1987); Slamon et al., *Science*, 244:707-712 (1989); and U.S. Pat. No. 4,968,603). To date, no point mutation analogous to that in the neu proto-oncogene has been reported for human tumors. Overexpression of ErbB2 (frequently but not uniformly due to gene amplification) has also been observed in other carcinomas including carcinomas of the stomach, endometrium, salivary gland, lung, kidney, colon, thyroid, pancreas and bladder. See, among others, King et al., *Science*, 229:974 (1985); Yokota et al., *Lancet*: 1:765-767 (1986); Fukushige et al., *Mol Cell Biol.*, 6:955-958 (1986); Guerin et al., *Oncogene Res.*, 3:21-31 (1988); Cohen et *Oncogene*, 4:81-88 (1989); Yonemura et al., *Cancer Res.*, 51:1034 (1991); Borst et al., *Gynecol. Oncol.*, 38:364 (1990); Weiner et al., *Cancer Res.*, 50:421-425 (1990); Kern et al., *Cancer Res.*, 50:5184 (1990); Park et al., *Cancer Res.*, 49:6605 (1989); Zhau et al., *Mol. Carcinog.*, 3:354-357 (1990); Aasland et al. *Br. J. Cancer* 57:358-363 (1988); Williams et al. Pathobiology 59:46-52 (1991); and McCann et al., *Cancer*, 65:88-92 (1990). ErbB2 may be overexpressed in prostate cancer (Gu et al. *Cancer Lett.* 99:185-9 (1996); Ross et al. *Hum. Pathol.* 28:827-33 (1997); Ross et al. *Cancer* 79:2162-70 (1997); and Sadasivan et al. *J. Urol.* 150:126-31 (1993)).

Antibodies directed against the rat p185$^{neu}$ and human ErbB2 protein products have been described. Drebin and colleagues have raised antibodies against the rat neu gene product, p185$^{neu}$ See, for example, Drebin et al., *Cell* 41:695-706 (1985); Myers et al., *Meth. Enzym.* 198:277-290 (1991); and WO94/22478. Drebin et al. *Oncogene* 2:273-277 (1988) report that mixtures of antibodies reactive with two distinct regions of p185$^{neu}$ result in synergistic anti-tumor effects on neu-transformed NIH-3T3 cells implanted into nude mice. See also U.S. Pat. No. 5,824,311 issued Oct. 20, 1998.

Hudziak et al., *Mol. Cell. Biol.* 9(3):1165-1172 (1989) describe the generation of a panel of anti-ErbB2 antibodies which were characterized using the human breast tumor cell line SK-BR-3. Relative cell proliferation of the SK-BR-3 cells following exposure to the antibodies was determined by crystal violet staining of the monolayers after 72 hours. Using this assay, maximum inhibition was obtained with the antibody called 4D5 which inhibited cellular proliferation by 56%. Other antibodies in the panel reduced cellular proliferation to a lesser extent in this assay. The antibody 4D5 was further found to sensitize ErbB2-overexpressing breast tumor cell lines to the cytotoxic effects of TNF-α. See also U.S. Pat. No. 5,677,171 issued Oct. 14, 1997. The anti-ErbB2 antibodies discussed in Hudziak et al. are further characterized in Fendly et al. *Cancer Research* 50:1550-1558 (1990); Kotts et al. In Vitro 26(3):59A (1990); Sarup et al. *Growth Regulation* 1:72-82 (1991); Shepard et al. *J. Clin. Immunol.* 11(3):117-127 (1991); Kumar et al. *Mol. Cell. Biol.* 11(2):979-986 (1991); Lewis et al. *Cancer Immunol. Immunother.* 37:255-263 (1993); Pietras et al. *Oncogene* 9:1829-1838 (1994); Vitetta et al. *Cancer Research* 54:5301-5309 (1994); Sliwkowski et al. *J. Biol. Chem.* 269(20):14661-14665 (1994); Scott et al. *J. Biol. Chem.* 266:14300-5 (1991); D'souza et al. *Proc. Natl. Acad. Sci.* 91:7202-7206 (1994); Lewis et al. *Cancer Research* 56:1457-1465 (1996); and Schaefer et al. *Oncogene* 15:1385-1394 (1997).

A recombinant humanized version of the murine anti-ErbB2 antibody 4D5 (huMAb4D5-8, rhuMAb HER2 or HERCEPTIN®; U.S. Pat. No. 5,821,337) is clinically active in patients with ErbB2-overexpressing metastatic breast cancers that have received extensive prior anti-cancer therapy (Baselga et al., *J. Clin. Oncol.* 14:737-744 (1996)). HERCEPTIN® received marketing approval from the Food and Drug Administration Sep. 25, 1998 for the treatment of patients with metastatic breast cancer whose tumors overexpress the ErbB2 protein.

Other anti-ErbB2 antibodies with various properties have been described in Tagliabue et al. *Int. J. Cancer* 47:933-937 (1991); McKenzie et al. *Oncogene* 4:543-548 (1989); Maier et al. *Cancer Res.* 51:5361-5369 (1991); Bacus et al. *Molecular Carcinogenesis* 3:350-362 (1990); Stancovski et al. *PNAS (USA)* 88:8691-8695 (1991); Bacus et al. *Cancer Research* 52:2580-2589 (1992); Xu et al. *Int. J. Cancer* 53:401-408 (1993); WO94/00136; Kasprzyk et al. *Cancer Research* 52:2771-2776 (1992); Hancock et al. *Cancer Res.* 51:4575-4580 (1991); Shawver et al. *Cancer Res.* 54:1367-1373 (1994); Arteaga et al. *Cancer Res.* 54:3758-3765 (1994); Harwerth et al. *J. Biol. Chem.* 267:15160-15167 (1992); U.S. Pat. No. 5,783,186; and Klapper et al. *Oncogene* 14:2099-2109 (1997).

Homology screening has resulted in the identification of two other ErbB receptor family members; ErbB3 (U.S. Pat. Nos. 5,183,884 and 5,480,968 as well as Kraus et al. *PNAS*

(*USA*) 86:9193-9197 (1989)) and ErbB4 (EP Pat Appln No 599,274; Plowman et al., *Proc. Natl. Acad. Sci. USA*, 90:1746-1750 (1993); and Plowman et al., *Nature,* 366:473-475 (1993)). Both of these receptors display increased expression on at least some breast cancer cell lines.

The ErbB receptors are generally found in various combinations in cells and heterodimerization is thought to increase the diversity of cellular responses to a variety of ErbB ligands (Earp et al. *Breast Cancer Research and Treatment* 35: 115-132 (1995)). EGFR is bound by six different ligands; epidermal growth factor (EGF), transforming growth factor alpha (TGF-α), amphiregulin, heparin binding epidermal growth factor (HB-EGF), betacellulin and epiregulin (Groenen et al. *Growth Factors* 11:235-257 (1994)). A family of heregulin proteins resulting from alternative splicing of a single gene are ligands for ErbB3 and ErbB4. The heregulin family includes alpha, beta and gamma heregulins (Holmes et al., *Science,* 256:1205-1210 (1992); U.S. Pat. No. 5,641,869; and Schaefer et al. *Oncogene* 15:1385-1394 (1997)); neu differentiation factors (NDFs), glial growth factors (GGFs); acetylcholine receptor inducing activity (ARIA); and sensory and motor neuron derived factor (SMDF). For a review, see Groenen et al. *Growth Factors* 11:235-257 (1994); Lemke, G. *Molec. & Cell. Neurosci.* 7:247-262 (1996) and Lee et al. *Pharm. Rev.* 47:51-85 (1995). Recently three additional ErbB ligands were identified; neuregulin-2 (NRG-2) which is reported to bind either ErbB3 or ErbB4 (Chang et al. *Nature* 387 509-512 (1997); and Carraway et al *Nature* 387:512-516 (1997)); neuregulin-3 which binds ErbB4 (Zhang et al. *PNAS* (*USA*) 94(18):9562-7 (1997)); and neuregulin-4 which binds ErbB4 (Harari et al. *Oncogene* 18:2681-89 (1999)) HB-EGF, betacellulin and epiregulin also bind to ErbB4.

While EGF and TGFα do not bind ErbB2, EGF stimulates EGFR and ErbB2 to form a heterodimer, which activates EGFR and results in transphosphorylation of ErbB2 in the heterodimer. Dimerization and/or transphosphorylation appears to activate the ErbB2 tyrosine kinase. See Earp et al., supra. Likewise, when ErbB3 is co-expressed with ErbB2, an active signaling complex is formed and antibodies directed against ErbB2 are capable of disrupting this complex (Sliwkowski et al., *J. Biol. Chem.,* 269(20):14661-14665 (1994)). Additionally, the affinity of ErbB3 for heregulin (HRG) is increased to a higher affinity state when co-expressed with ErbB2. See also, Levi et al., *Journal of Neuroscience* 15: 1329-1340 (1995); Morrissey et al., *Proc. Natl. Acad. Sci. USA* 92: 1431-1435 (1995); and Lewis et al., *Cancer Res.,* 56:1457-1465 (1996) with respect to the ErbB2-ErbB3 protein complex. ErbB4, like ErbB3, forms an active signaling complex with ErbB2 (Carraway and Cantley, *Cell* 78:5-8 (1994)).

Pain Management

Chronic pain is a common symptom of a variety of diseases and pathologic conditions, and includes nociceptive pain (pain caused by an injury to body tissues), neuropathic pain (pain caused by abnormalities in the nerves, spinal cord, or brain), and psychogenic pain (entirely or mostly related to a psychological disorder). Nociceptive pain includes somatic pain, which arises from bone, joint, muscle, skin, or connective tissue, and visceral pain, which arises from visceral organs, such as the gastrointestinal tract and the pancreas.

Mild to moderate pain is typically treated by nonsteroidal antiinflammatory drugs (NSAIDs), such as acetaminophen, ibuprofen, aspirin, ketorolac, etodolac, and the like. Treatment of more severe chronic pain may include opiate and NSAID combinations, such as aspirin and oxycodone (Percodan), acetaminophen and hydrocodone (Vicodin and Lortab).

Pain is also a frequent symptom of advanced cancer. For example, about 60% of patients with hormone-refractory prostate cancer suffer significant pain. Typically the pain results directly from the cancer (including cancer metastasis), although sometimes it can also be associated with the cancer treatment itself For example, chronic pain may develop if there has been nerve damage during surgical removal of cancer. Chemotherapy can also cause pain in several ways. Some chemotherapy drugs, referred to as vesicants, can harm tissues if they leak out of the vein. In some instances, chemotherapy causes sores in the mouth (stomatitis) or lining of the intestines (mucositis). Peripheral neuropathy can occur with certain chemotherapy drugs when they are administered long-term in high doses. Radiation treatment can also cause pain because it can affect normal cells that surround the cancerous tumor being treated.

At present, cancer-related pain is usually managed by opiate analgesics, such as morphine or heroin with the goal to relieve the patient's pain by adjusting the opiate dosage to maintain a pain score of 3 or less on a 10-point visual analog scale. This treatment, however, is not optimal. Common side effects include drowsiness and constipation. In addition, patients often experience tolerance and develop a physical dependency on opiate analgesics, which reduces the effectiveness of the pain treatment and raises serious issues of drug dependency. When an opioid is discontinued, withdrawal symptoms may appear, the character and severity of which are dependent upon such factors as the particular opioid being withdrawn, the daily dose of the opioid that is being withdrawn, the duration of opioid treatment, and the condition of the drug-dependent individual. Withdrawal itself is associated with symptoms including severe pain. Often the only effective treatment for cancer-related pain is successful eradication of the tumor.

Severe, persisting pain is debilitating for patients and their caregivers, and is often under-treated due to fear of opioid addition by both patients and medical professionals. Since current therapies are unsatisfactory, it is important to develop further treatment modalities for the management of chronic pain, including cancer-related pain, that are more effective and are devoid of the undesired side-effects and risks associated with current treatment approaches.

SUMMARY OF THE INVENTION

This invention is based, at least in part, on the surprising observation that patients with prostate cancer treated with an ErbB antagonist, namely rhuMAb 2C4, experienced diminished pain or showed reduced analgesia requirement, even where the tumor was progressing. This indicates that rhuMAb 2C4 has analgesic properties.

In one aspect, the invention concern a method of treating pain in a patient comprising administering an effective dose of an ErbB antagonist to the patient.

In another aspect, the invention concerns a method of treating pain in a patient comprising administering an ErbB antagonist to the patient in a dose confirmed to reduce or eliminate the pain or the analgesia requirement of the patient.

In one embodiment, the pain is measured by a pain score or quality of life score reflective of pain. Pain may, for example, be measured by the McGill Pain Index on a six point scale of 0 to 5. Pain may alternatively be measured by using a visual analog scale of 0-100 reflective of the subjective feeling of pain of the patient. The analgesia requirement may be measured using an analgesia score. In a particular embodiment, one dose of a non-steroidal analgesic agent corresponds to an analgesia score of 1, and one 10 mg dose of morphine, or an equivalent dose of another opiate analgesic agent corresponds to an analgesia score of 2.

In another embodiment, pain is monitored daily.

In yet another embodiment, analgesia requirement is monitored daily.

In another aspect, the invention concerns a method for treating cancer-related pain in a patient diagnosed with cancer, comprising administering an effective amount of an ErbB antagonist to the patient, wherein the cancer is not in remission or continues to grow during said treatment.

In a specific embodiment of the method, the cancer is not in remission during said treatment, or continues to group during treatment.

The cancer can be any kind of cancer, including, for example, breast cancer, ovarian cancer, prostate cancer, pancreatic cancer, squamous cell cancer, lung cancer, cancer of the peritoneum, hepatocellular cancer, gastric cancer, glioblastoma, cervical cancer, liver cancer, bladder cancer, hepatoma, colon cancer, rectal cancer, colorectal cancer, endometrial or uterine carcinoma, salivary gland carcinoma, kidney cancer, vulval cancer, thyroid cancer, hepatic carcinoma, anal carcinoma, penile carcinoma, and head and neck cancer.

In a particular embodiment, the cancer is metastatic cancer.

In another embodiment, the metastasis is soft tissue metastasis.

In yet another embodiment, the metastasis includes bone metastasis.

In a preferred embodiment, the cancer is prostate cancer, specifically including androgen independent prostate cancer.

In another embodiment, the cancer is prostate cancer, and the patient's PSA shows no reduction during treatment, or becomes elevated during treatment.

In a further aspect, the invention concerns a method for treating non-cancer related pain in a patient comprising administering an effective amount of an ErbB antagonist to the patient.

In a still further aspect, the invention concerns a kit comprising an effective amount of an ErbB antagonist, and instructions to administer said antagonist for the treatment of pain.

In all aspects, the ErbB antagonist preferably is an antibody. The antibody can, for example, be a monoclonal antibody that binds an ErbB. In another embodiment, the antibody blocks ligand activation of an ErbB. In yet another embodiment, the antibody blocks formation of an ErbB heterodimer. In a preferred embodiment, the antibody blocks binding of monoclonal antibody 2C4 to ErbB2. In another preferred embodiment, the antibody has a biological characteristic of monoclonal antibody 2C4. In a further preferred embodiment, the antibody comprises monoclonal antibody 2C4 or humanized 2C4.

The antibody may be an antibody fragment, such as, for example, a Fab fragment and may, or may not be conjugated with a cytotoxic agent.

The pain treated in accordance with the present invention can be acute pain or chronic pain, such as, without limitation., nociceptive pain, neuropathic pain and psychogenic pain, and can be cancer related or not associated with cancer. When the pain is cancer related the cancer may, but does not have to, express an ErbB receptor, such as, ErbB2 and/or EGFR. In a specific embodiment, the cancer is metastatic cancer, where the metastasis can be soft tissue and/or bone metastasis.

In another embodiment, the cancer is selected from the group consisting of breast cancer, ovarian cancer, prostate cancer, pancreatic cancer, squamous cell cancer, lung cancer, cancer of the peritoneum, hepatocellular cancer, gastric cancer, glioblastoma, cervical cancer, liver cancer, bladder cancer, hepatoma, colon cancer, rectal cancer, colorectal cancer, endometrial or uterine carcinoma, salivary gland carcinoma, kidney cancer, vulval cancer, thyroid cancer, hepatic carcinoma, anal carcinoma, penile carcinoma, and head and neck cancer.

In a particular embodiment, the cancer is prostate cancer, such as, for example, androgen independent prostate cancer.

BRIEF DESCRIPTION OF THE DRAWINGS

Figure 1A:
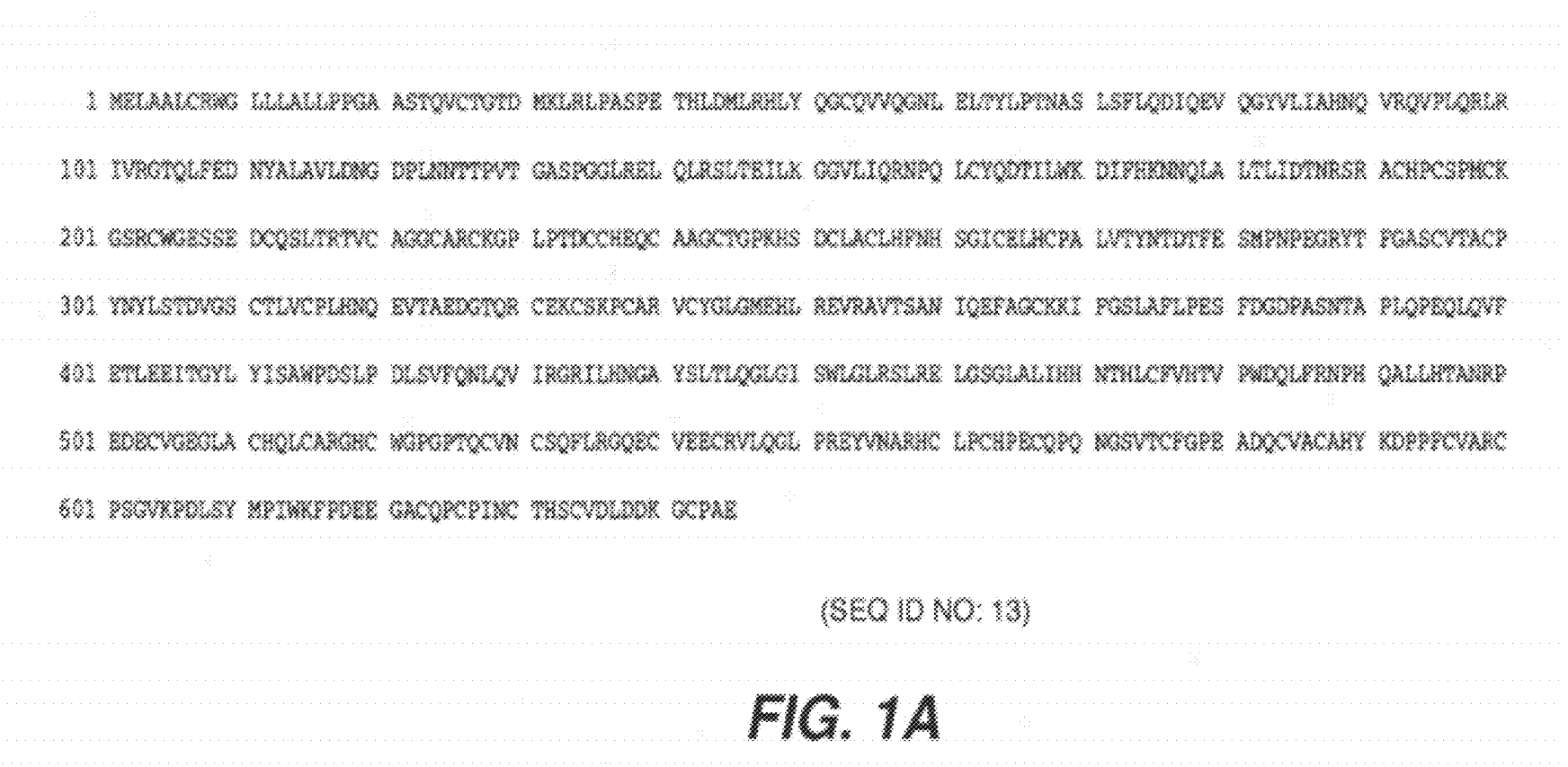

FIGS. 1A and 1B depict epitope mapping of residues 22-645 within the extracellular domain (ECD) of ErbB2 (amino acid sequence, including signal sequence, shown in FIG. 1A; SEQ ID NO:13) as determined by truncation mutant analysis and site-directed mutagenesis (Nakamura et al. *J. of Virology* 67(10):6179-6191 (1993); and Renz et al. *J. Cell Biol.* 125(6):1395-1406 (1994)). The various ErbB2-ECD truncations or point mutations were prepared from cDNA using polymerase chain reaction technology. The ErbB2 mutants were expressed as gD fusion proteins in a mammalian expression plasmid. This expression plasmid uses the cytomegalovirus promoter/enhancer with SV40 termination and polyadenylation signals located downstream of the inserted cDNA. Plasmid DNA was transfected into 293 cells. One day following transfection, the cells were metabolically labeled overnight in methionine and cysteine-free, low glucose DMEM containing 1% dialyzed fetal bovine serum and 25 μCi each of $^{35}$S methionine and $^{35}$S cysteine. Supernatants were harvested and either the anti-ErbB2 monoclonal antibodies or control antibodies were added to the supernatant and incubated 2-4 hours at 4° C. The complexes were precipitated, applied to a 10-20% Tricine SDS gradient gel and electrophoresed at 100 V. The gel was electroblotted onto a membrane and analyzed by autoradiography. As shown in FIG. 1B, the anti-ErbB2 antibodies 7C2, 7F3, 2C4, 7D3, 3E8, 4D5, 2H11 and 3H4 bind various ErbB2 ECD epitopes.

FIG. 2A shows dose-response curves for 2C4 or 7F3 inhibition of HRG stimulation of tyrosine phosphorylation. FIG. 2B shows dose-response curves for the inhibition of $^{125}$I-labeled rHRGβ1$_{177-244}$ binding to MCF7 cells by 2C4 or 7F3.

FIG. 6A shows inhibition of $^{125}$I-HRG binding to MCF7 cells by chimeric 2C4 Fab or intact murine monoclonal antibody 2C4. MCF7 cells were seeded in 24-well plates ($1\times10^5$ cells/well) and grown to about 85% confluency for two days. Binding experiments were conducted as described in Lewis et al. *Cancer Research* 56:1457-1465 (1996). FIG. 6B depicts inhibition of rHRGβ1 activation of p180 tyrosine phosphorylation in MCF7 cells performed as described in Lewis et al. *Cancer Research* 56:1457-1465 (1996).

FIGS. 7A and 7B depict alignments of the amino acid sequences of the variable light ($V_L$) (FIG. 7A) and variable heavy ($V_H$) (FIG. 7B) domains of murine monoclonal antibody 2C4 (SEQ ID Nos. 1 and 2, respectively); $V_L$ and $V_H$ domains of humanized 2C4 version 574 (SEQ ID Nos. 3 and 4, respectively), and human $V_L$ and $V_H$ consensus frameworks (hum κ1, light kappa subgroup I; humIII, heavy subgroup III) (SEQ ID Nos. 5 and 6, respectively). Asterisks identify differences between humanized 2C4 version 574 and murine monoclonal antibody 2C4 or between humanized 2C4 version 574 and the human framework. Complementarity Determining Regions (CDRs) are in brackets.

DETAILED DESCRIPTION OF THE PREFERRED EMBODIMENTS

Figure 1B:
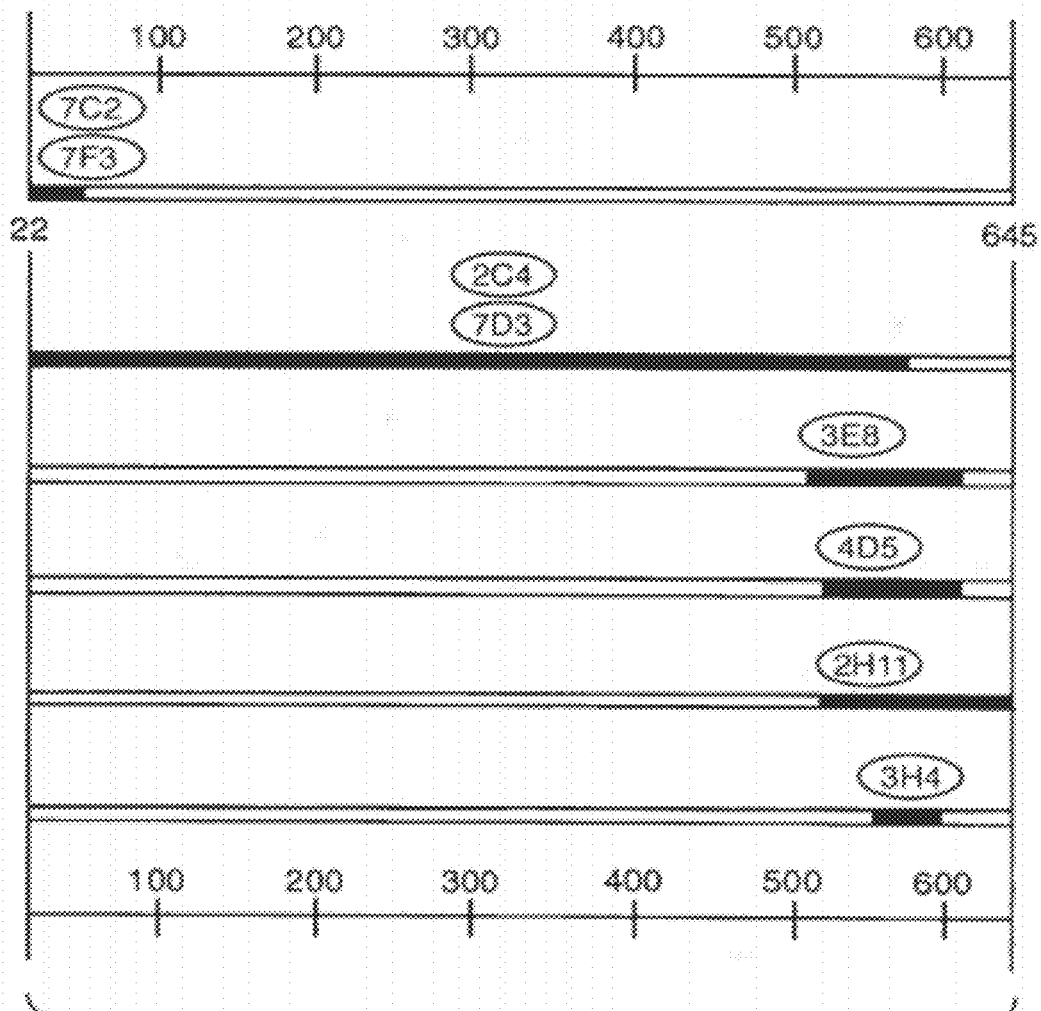

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994) provides one skilled in the art with a general guide to many of the terms used in the present disclosure.

I. Definitions

The term "pain" is used herein in the broadest sense and refers to all types of pain, including acute and chronic pain, such as nociceptive pain, e.g. somatic pain and visceral pain; neuropathic pain, e.g. centrally generated pain and peripherally generated pain; and psychogenic pain. The term preferably refers to chronic pain, most preferably nociceptive pain, including somatic pain and visceral pain, which can be cancer related, not associated with cancer, or only partially associated with cancer.

The term "nociceptive pain" is used to include all pain caused by injury to body tissues, including, without limitation, by a cut, bruise, bone fracture, crush injury, burn, and the like. This type of pain is typically aching, sharp, or throbbing. Pain receptors for tissue injury (nociceptor) are located mostly in the skin or in the internal organs.

The term "somatic pain" is used to refer to pain arising from bone, joint, muscle, skin, or connective tissue. This type of pain is typically aching or throbbing in quality and is well localized.

The term "visceral pain" is used herein to refer to pain arising from visceral organs, such as the gastrointestinal tract and pancreas. Visceral pain includes aching and fairly well localized pain caused by tumor involvement of the organ capsule. Another type of visceral pain, which is typically caused by obstruction of hollow viscus, is characterized by intermittent cramping and poorly localized pain.

The term "neuropathic pain" is used herein to refer to pain originating from abnormal processing of sensory input by the peripheral or central nervous system.

The term "analgesia" is used to refer to the absence of pain in response to a stimulus that would be normally painful and to a treatment with an analgesic agent. The term "analgesic agent" and grammatical equivalents thereof refer to agents that are capable of invoking analgesia.

The term "analgesia requirement" of a patient is used herein to refer to the need of administering an analgesic agent (other than an ErbB antagonist) to a patient in order to manage the patient's pain.

"Treatment" refers to both therapeutic treatment and prophylactic or preventative measures. Those in need of treatment include those already experiencing pain as well as those in which pain is to be prevented.

The term "effective amount" refers to an amount of the ErbB antagonist effective to reduce pain, at least to some extent, or to reduce or eliminate the analgesia requirement while maintaining the same or reduced pain score or subjective feeling of pain as experienced under analgesia, prior to the administration of the ErbB antagonist. Pain and reduction in pain can be evaluated by using any of the pain score systems well known in the art of pain management and/or a Quality of Life Score system for pain. Preferably, pain is measured based on the McGill Pain Index using a 6 point scale (0-5), where 0=no pain, 1=mild pain, 2=discomforting pain, 3=distressing pain, 4=horrible pain, 5=excruciating pain. Quality of Life Score for pain can be determined using a visual analog scale of 0-100.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

The term "PSA" is used herein to refer to the level of a prostate-specific antigen in the blood produced by the prostate, as determined by the prostate-specific antigen test. The amount of this antigen increases if the prostate is cancerous, and typically continues to increase as the cancer progresses.

An "ErbB" is a receptor protein tyrosine kinase which belongs to the ErbB receptor family and includes EGFR, ErbB2, ErbB3 and ErbB4 receptors and other members of this family to be identified in the future. The ErbB will generally comprise an extracellular domain, which may bind an ErbB ligand; a lipophilic transmembrane domain; a conserved intracellular tyrosine kinase domain; and a carboxyl-terminal signaling domain harboring several tyrosine residues which can be phosphorylated. The ErbB may be a "native sequence" ErbB or an "amino acid sequence variant" thereof. Preferably the ErbB is native sequence human ErbB.

The terms "ErbB1", "epidermal growth factor receptor," "HER1," and "EGFR" are used interchangeably herein and refer to EGFR as disclosed, for example, in Carpenter et al. *Ann. Rev. Biochem.* 56:881-914 (1987), including naturally occurring mutant forms thereof (e.g. a deletion mutant EGFR as in Humphrey et al. *PNAS (USA)* 87:4207-4211 (1990); type II EGFR mutant (U.S. Pat. No. 6,455,498) etc). erbB1 refers to the gene encoding the EGFR protein product.

The expressions "ErbB2" and "HER2" are used interchangeably herein and refer to human HER2 protein described, for example, in Semba et al., *PNAS (USA)* 82:6497-6501 (1985) and Yamamoto et al. *Nature* 319:230-234 (1986) (Genebank accession number X03363). The term "erbB2" refers to the gene encoding human ErbB2 and "neu" refers to the gene encoding rat p185$^{neu}$. Preferred ErbB2 is native sequence human ErbB2.

"ErbB3" and "HER3" refer to the receptor polypeptide as disclosed, for example, in U.S. Pat. Nos. 5,183,884 and 5,480,968 as well as Kraus et al. *PNAS (USA)* 86:9193-9197 (1989).

The terms "ErbB4" and "HER4" herein refer to the receptor polypeptide as disclosed, for example, in EP Pat Appln No 599,274; Plowman et al., *Proc. Natl. Acad. Sci. USA,* 90:1746-1750 (1993); and Plowman et al., *Nature,* 366:473-475 (1993), including isoforms thereof, e.g., as disclosed in WO99/19488, published Apr. 22, 1999.

By "ErbB ligand" is meant a polypeptide which binds to and/or activates an ErbB. The term includes membrane-bound precursor forms of the ErbB ligand, as well as proteolytically processed soluble forms of the ErbB ligand. The ErbB ligand of particular interest herein is a native sequence human ErbB ligand such as epidermal growth factor (EGF) (Savage et al., *J. Biol. Chem.* 247:7612-7621 (1972)); transforming growth factor alpha (TGF-α) (Marquardt et al., *Science* 223:1079-1082 (1984)); amphiregulin also known as schwanoma or keratinocyte autocrine growth factor (Shoyab et al. *Science* 243:1074-1076 (1989); Kimura et al. *Nature* 348:257-260 (1990); and Cook et al. *Mol. Cell. Biol.* 11:2547-2557 (1991)); betacellulin (Shing et al., *Science* 259:1604-1607 (1993); and Sasada et al. *Biochem. Biophys. Res. Commun.* 190:1173 (1993)); heparin-binding epidermal growth factor (HB-EGF) (Higashiyama et al., *Science* 251:936-939 (1991)); epiregulin (Toyoda et al., *J. Biol. Chem.* 270:7495-7500 (1995); and Komurasaki et al. *Oncogene* 15:2841-2848 (1997)); a heregulin (see below); neuregulin-2 (NRG-2) (Carraway et al., *Nature* 387:512-516 (1997)); neuregulin-3 (NRG-3) (Zhang et al., *Proc. Natl. Acad. Sci.* 94:9562-9567 (1997)); neuregulin-4 (NRG-4) (Harari et al. *Oncogene* 18:2681-89 (1999)) or cripto (CR-1) (Kannan et al. *J. Biol. Chem.* 272(6):3330-3335 (1997)). ErbB ligands which bind EGFR include EGF, TGF-α, amphiregulin, betacellulin, HB-EGF and epiregulin. ErbB ligands which bind ErbB3 include heregulins. ErbB ligands capable of binding ErbB4 include betacellulin, epiregulin, HB-EGF, NRG-2, NRG-3, NRG-4 and heregulins.

"Heregulin" (HRG) when used herein refers to a polypeptide encoded by the heregulin gene product as disclosed in U.S. Pat. No. 5,641,869 or Marchionni et al., *Nature,* 362:312-318 (1993). Examples of heregulins include heregulin-α, heregulin-β1, heregulin-β2 and heregulin-β3 (Holmes et al., *Science,* 256:1205-1210 (1992); and U.S. Pat. No. 5,641,869); neu differentiation factor (NDF) (Peles et al. *Cell* 69:205-216 (1992)); acetylcholine receptor-inducing activity (ARIA) (Falls et al. *Cell* 72:801-815 (1993)); glial growth factors (GGFs) (Marchionni et al., *Nature,* 362:312-318 (1993)); sensory and motor neuron derived factor (SMDF) (Ho et al. *J. Biol. Chem.* 270:14523-14532 (1995)); γ-heregulin (Schaefer et al. *Oncogene* 15:1385-1394 (1997)). The term includes biologically active fragments and/or amino acid sequence variants of a native sequence HRG polypeptide, such as an EGF-like domain fragment thereof (e.g. HRGβ1$_{177-244}$).

An "ErbB hetero-oligomer" herein is a noncovalently associated oligomer comprising at least two different ErbBs. Such complexes may form when a cell expressing two or more ErbBs is exposed to an ErbB ligand (Sliwkowski et al., *J. Biol. Chem.,* 269(20):14661-14665 (1994)). Examples of such ErbB hetero-oligomers include EGFR-ErbB2, ErbB2-ErbB3 and ErbB3-ErbB4 complexes. Moreover, the ErbB hetero-oligomer may comprise two or more ErbB2 receptors combined with a different ErbB, such as ErbB3, ErbB4 or EGFR. Other proteins, such as a cytokine receptor subunit (e.g. gp130) may be included in the hetero-oligomer. The patient herein may have been subjected to an assay to determine whether ErbB heterodimers, especially an EGFR-ErbB2 and/or ErbB2-ErbB3 heterodimer are present in cells of the patient, e.g. in diseased tissue therefrom.

By "ligand activation of an ErbB" is meant signal transduction (e.g. that caused by an intracellular kinase domain of an ErbB phosphorylating tyrosine residues in the ErbB or a substrate polypeptide) mediated by ErbB ligand binding to a ErbB hetero-oligomer comprising the ErbB of interest. Generally, this will involve binding of an ErbB ligand to an ErbB hetero-oligomer which activates a kinase domain of one or more of the ErbBs in the hetero-oligomer and thereby results in phosphorylation of tyrosine residues in one or more of the ErbBs and/or phosphorylation of tyrosine residues in additional substrate polypeptides(s). ErbB activation can be quantified using various tyrosine phosphorylation assays.

An "ErbB antagonist" is a molecule which blocks (reduces or prevents) a biological activity of one or more ErbB(s). Preferably, the antagonist blocks (reduces or prevents) ligand activation of an ErbB. Generally, the antagonist will be an antibody, small peptide or non-peptide (organic) molecule, antisense molecule, oligonucleotide decoy, and the like, which inhibits a biological activity of an ErbB receptor. Thus, for example, an antagonist may bind to or otherwise associate with an ErbB and reduce tyrosine kinase activation thereof. ErbB antagonists also include molecules that bind to or associate with ErbB ligands or other members of the ErbB signaling pathway, thereby inhibiting ErbB biological activity. The preferred ErbB antagonist is an antibody that binds ErbB2, or EGFR, or a hetero-oligomer (e.g. a heterodimer) comprising ErbB2 and/or EGFR, and blocks ligand activation of an ErbB. The most preferred antagonist is rhuMAb 2C4 or a molecule having a biological characteristic of rhuMAb 2C4. By way of example, the antagonist may also be an EGFR-targeted drug and/or a tyrosine kinase inhibitor.

As used herein, the term "EGFR-targeted drug" refers to a therapeutic agent that binds to EGFR and, optionally, inhibits EGFR activation. Examples of such agents include antibodies and small molecules that bind to EGFR. Examples of antibodies which bind to EGFR include MAb 579 (ATCC CRL HB 8506), MAb 455 (ATCC CRL HB8507), MAb 225

(ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (11225) (see, WO 96/40210, Imclone Systems Inc.); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF (see WO98/50433, Abgenix). The anti-EGFR antibody may be conjugated with a cytotoxic agent, thus generating an immunoconjugate (see, e.g., EP659,439A2, Merck Patent GmbH). Examples of small molecules that bind to EGFR include ZD1839 or Gefitinib (IRESSA®; Astra Zeneca), CP-358,774 (TARCEVA®; Genentech/OSI) and AG1478, AG1571 (SU 5271; Sugen).

A "tyrosine kinase inhibitor" is a molecule which inhibits to some extent tyrosine kinase activity of a tyrosine kinase such as an ErbB. Examples of such inhibitors include the EGFR-targeted drugs noted in the preceding paragraph as well as quinazolines such as PD 153035,4-(3-chloroanilino) quinazoline, pyridopyrimidines, pyrimidopyrimidines, pyrrolopyrimidines, such as CGP 59326, CGP 60261 and CGP 62706, and pyrazolopyrimidines, 4-(phenylamino)-7H-pyrrolo[2,3-d]pyrimidines, curcumin (diferuloyl methane, 4,5-bis(4-fluoroanilino)phthalimide), tryphostines containing nitrothiophene moieties; PD-0183805 (Warner-Lamber); antisense molecules (e.g. those that bind to ErbB-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-ErbB inhibitors such as CI-1033 (Pfizer); Affinitac (ISIS 3521; Isis/Lilly); Imatinib mesylate (Gleevac; Novartis); PKI 166 (Novartis); GW2016 (Glaxo SmithKline); CI-1033 (Pfizer); EKB-569 (Wyeth); Semaxanib (Sugen); ZD6474 (AstraZeneca); PTK-787 (Novartis/Schering AG); INC-1C11 (Imclone); or as described in any of the following patent publications: U.S. Pat. No. 5,804, 396; WO99/09016 (American Cyanimid); WO98/43960 (American Cyanamid); WO97/38983 (Warner Lambert); WO99/06378 (Warner Lambert); WO99/06396 (Warner Lambert); WO96/30347 (Pfizer, Inc); WO96/33978 (Zeneca); WO96/3397 (Zeneca); and WO96/33980 (Zeneca).

A "native sequence" polypeptide is one which has the same amino acid sequence as a polypeptide (e.g., ErbB or ErbB ligand) derived from nature. Such native sequence polypeptides can be isolated from nature or can be produced by recombinant or synthetic means. Thus, a native sequence polypeptide can have the amino acid sequence of naturally occurring human polypeptide, murine polypeptide, or polypeptide from any other mammalian species.

The term "amino acid sequence variant" refers to polypeptides having amino acid sequences that differ to some extent from a native sequence polypeptide. Ordinarily, amino acid sequence variants will possess at least about 70% homology with at least one receptor binding domain of a native ErbB ligand or with at least one ligand binding domain of a native ErbB, and preferably, they will be at least about 80%, more preferably at least about 90% homologous with such receptor or ligand binding domains. The amino acid sequence variants possess substitutions, deletions, and/or insertions at certain positions within the amino acid sequence of the native amino acid sequence.

"Homology" is defined as the percentage of residues in the amino acid sequence variant that are identical after aligning the sequences and introducing gaps, if necessary, to achieve the maximum percent homology. Methods and computer programs for the alignment are well known in the art. One such computer program is "Align 2", authored by Genentech, Inc., which was filed with user documentation in the United States Copyright Office, Washington, D.C. 20559, on Dec. 10, 1991.

The term "antibody" herein is used in the broadest sense and specifically covers intact monoclonal antibodies, polyclonal antibodies, multispecific antibodies (e.g. bispecific antibodies) formed from at least two intact antibodies, and antibody fragments, so long as they exhibit the desired biological activity.

The term "monoclonal antibody" as used herein refers to an antibody obtained from a population of substantially homogeneous antibodies, i.e., the individual antibodies comprising the population are identical except for variants that may arise during production of the antibody. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature,* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature,* 352:624-628 (1991) and Marks et al., *J. Mol. Biol.,* 222:581-597 (1991), for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA,* 81:6851-6855 (1984)). Chimeric antibodies of interest herein include "primatized" antibodies comprising variable domain antigen-binding sequences derived from a non-human primate (e.g. Old World Monkey, Ape etc) and human constant region sequences.

"Antibody fragments" comprise a portion of an intact antibody, preferably comprising the antigen-binding or variable region thereof. Examples of antibody fragments include Fab, Fab', F(ab')$_2$, and Fv fragments; diabodies; linear antibodies; single-chain antibody molecules; and multispecific antibodies formed from antibody fragment(s).

An "intact" antibody is one which comprises an antigen-binding variable region as well as a light chain constant domain ($C_L$) and heavy chain constant domains, $C_H1$, $C_H2$ and $C_H3$. The constant domains may be native sequence constant domains (e.g. human native sequence constant domains) or amino acid sequence variant thereof. Preferably, the intact antibody has one or more effector functions.

Antibody "effector functions" refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc.

Depending on the amino acid sequence of the constant domain of their heavy chains, intact antibodies can be assigned to different "classes". There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or U.S. Pat. No. 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

"Complement dependent cytotoxicity" or "CDC" refers to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods* 202:163 (1996), may be performed.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')₂ fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')₂ antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (κ) and lambda (λ), based on the amino acid sequences of their constant domains.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the scFv to form the desired structure for antigen binding. For a review of scFv see Plückthun in *The Pharmacology of Monoclonal Antibodies*, vol. 113, Rosenburg and Moore eds., Springer-Verlag, New York, pp. 269-315 (1994). Anti-ErbB2 antibody scFv fragments are described in WO93/16185; U.S. Pat. No. 5,571,894; and U.S. Pat. No. 5,587,458.

The term "diabodies" refers to small antibody fragments with two antigen-binding sites, which fragments comprise a variable heavy domain ($V_H$) connected to a variable light domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

Humanized anti-ErbB2 antibodies include huMAb4D5-1, huMAb4D5-2, huMAb4D5-3, huMAb4D5-4, huMAb4D5-5, huMAb4D5-6, huMAb4D5-7 and huMAb4D5-8 (HERCEPTIN®) as described in Table 3 of U.S. Pat. No. 5,821,337 expressly incorporated herein by reference; humanized 520C9 (WO93/21319) and humanized 2C4 antibodies as described hereinbelow.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody "which binds" an antigen of interest, e.g. ErbB2 antigen, is one capable of binding that antigen with sufficient affinity such that the antibody is useful as a therapeutic agent in targeting a cell expressing the antigen. Where the antibody is one which binds ErbB2, it will usually preferentially bind ErbB2 as opposed to other ErbBs, and may be one which does not significantly cross-react with other proteins such as EGFR, ErbB3 or ErbB4. In such embodiments, the extent of binding of the antibody to these non-ErbB2 proteins (e.g., cell surface binding to endogenous receptor) will be less than 10% as determined by fluorescence activated cell sorting (FACS) analysis or radioimmunoprecipitation (RIA). Sometimes, the anti-ErbB2 antibody will not significantly cross-react with the rat neu protein, e.g., as described in Schecter et al. *Nature* 312:513 (1984) and Drebin et al., *Nature* 312:545-548 (1984).

An antibody which "blocks" ligand activation of an ErbB is one which reduces or prevents such activation as hereinabove defined, wherein the antibody is able to block ligand activation of the ErbB substantially more effectively than monoclonal antibody 4D5, e.g. about as effectively as monoclonal antibodies 7F3 or 2C4 or Fab fragments thereof and preferably about as effectively as monoclonal antibody 2C4 or a Fab fragment thereof. For example, the antibody that blocks ligand activation of an ErbB may be one which is about 50-100% more effective than 4D5 at blocking formation of an ErbB hetero-oligomer. Blocking of ligand activation of an ErbB can occur by any means, e.g. by interfering with: ligand binding to an ErbB, ErbB complex formation, tyrosine kinase activity of an ErbB in an ErbB complex and/or phosphorylation of tyrosine kinase residue(s) in or by an ErbB. Examples of antibodies which block ligand activation of an ErbB include monoclonal antibodies 2C4 and 7F3 (which block HRG activation of ErbB2/ErbB3 and ErbB2/ErbB4 hetero-oligomers; and EGF, TGF-α, amphiregulin, HB-EGF and/or epiregulin activation of an EGFR/ErbB2 hetero-oligomer); and L26, L96 and L288 antibodies (Klapper et al. *Oncogene* 14:2099-2109 (1997)), which block EGF and NDF binding to T47D cells which express EGFR, ErbB2, ErbB3 and ErbB4.

An antibody having a "biological characteristic" of a designated antibody, such as the monoclonal antibody designated 2C4, is one which possesses one or more of the biological characteristics of that antibody which distinguish it from other antibodies that bind to the same antigen (e.g. ErbB2). For example, an antibody with a biological characteristic of 2C4 may block HRG activation of an ErbB hetero-oligomer comprising ErbB2 and ErbB3 or ErbB4; block EGF, TGF-α HB-EGF, epiregulin and/or amphiregulin activation of an ErbB comprising EGFR and ErbB2; block EGF, TGF-α and/or HRG mediated activation of MAPK; and/or bind the same epitope in the extracellular domain of ErbB2 as that bound by 2C4 (e.g. which blocks binding of monoclonal antibody 2C4 to ErbB2).

Unless indicated otherwise, the expression "monoclonal antibody 2C4" refers to an antibody that has antigen binding residues of, or derived from, the murine 2C4 antibody of the Examples below. For example, the monoclonal antibody 2C4 may be murine monoclonal antibody 2C4 or a variant thereof, such as humanized antibody 2C4, possessing antigen binding amino acid residues of murine monoclonal antibody 2C4. Examples of humanized 2C4 antibodies are provided in Example 3 below. Unless indicated otherwise, the expression "rhuMAb 2C4" when used herein refers to an antibody comprising the variable light ($V_L$) and variable heavy ($V_H$) sequences of SEQ ID Nos. 3 and 4, respectively, fused to human light and heavy IgG1 (non-A allotype) constant region sequences optionally expressed by a Chinese Hamster Ovary (CHO) cell.

Unless indicated otherwise, the term "monoclonal antibody 4D5" refers to an antibody that has antigen binding residues of, or derived from, the murine 4D5 antibody (ATCC CRL 10463). For example, the monoclonal antibody 4D5 may be murine monoclonal antibody 4D5 or a variant thereof, such as a humanized 4D5, possessing antigen binding residues of murine monoclonal antibody 4D5. Exemplary humanized 4D5 antibodies include huMAb4D5-1, huMAb4D5-2, huMAb4D5-3, huMAb4D5-4, huMAb4D5-5, huMAb4D5-6, huMAb4D5-7 and huMAb4D5-8 (HERCEPTIN®) as in U.S. Pat. No. 5,821,337, with huMAb4D5-8 (HERCEPTIN®) being a preferred humanized 4D5 antibody.

A "growth inhibitory agent" when used herein refers to a compound or composition which inhibits growth of a cell, especially an ErbB expressing cell either in vitro or in vivo. Thus, the growth inhibitory agent may be one which significantly reduces the percentage of ErbB expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13.

Examples of "growth inhibitory" antibodies are those which bind to ErbB2 and inhibit the growth of cells overexpressing ErbB2. Preferred growth inhibitory anti-ErbB2 antibodies inhibit growth of SK-BR-3 breast tumor cells in cell culture by greater than 20%, and preferably greater than 50% (e.g. from about 50% to about 100%) at an antibody concentration of about 0.5 to 30 μg/ml, where the growth inhibition is determined six days after exposure of the SK-BR-3 cells to the antibody (see U.S. Pat. No. 5,677,171 issued Oct. 14, 1997). The SK-BR-3 cell growth inhibition assay is described in more detail in that patent and hereinbelow. The preferred growth inhibitory antibody is monoclonal antibody 4D5, e.g., humanized 4D5.

An antibody which "induces cell death" is one which causes a viable cell to become nonviable. The cell is generally one which expresses the ErbB2 receptor, especially where the cell overexpresses the ErbB2 receptor. Preferably, the cell is a cancer cell, e.g. a breast, ovarian, stomach, endometrial, salivary gland, lung, kidney, colon, thyroid, pancreatic or bladder cell. In vitro, the cell may be a SK-BR-3, BT474, Calu 3, MDA-MB-453, MDA-MB-361 or SKOV3 cell. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e. in the absence of complement) and in the absence of immune effector cells. To determine whether the antibody is able to induce cell death, loss of membrane integrity as evaluated by uptake of propidium iodide (PI), trypan blue (see Moore et al. *Cytotechnology* 17:1-11 (1995)) or 7AAD can be assessed relative to untreated cells. Preferred cell death-inducing antibodies are those which induce PI uptake in the PI uptake assay in BT474 cells (see below).

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses the ErbB2 receptor. Preferably the cell is a tumor cell, e.g. a breast, ovarian, stomach, endometrial, salivary gland, lung, kidney, colon, thyroid, pancreatic or bladder cell. In vitro, the cell may be a SK-BR-3, BT474, Calu 3 cell, MDA-MB-453, MDA-MB-361 or SKOV3 cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody which induces apoptosis is one which results in about 2 to 50 fold, preferably about 5 to 50 fold, and most preferably about 10 to 50 fold, induction of annexin binding relative to untreated cell in an annexin binding assay using BT474 cells (see below). Sometimes the pro-apoptotic antibody will be one which further blocks ErbB ligand activation of an ErbB (e.g. 7F3 antibody); i.e. the antibody shares a biological characteristic with monoclonal antibody 2C4. In other situations, the antibody is one which does not significantly block ErbB ligand activation of an ErbB (e.g. 7C2). Further, the antibody may be one like 7C2 which, while inducing apoptosis, does not induce a large reduction in the percent of cells in S phase (e.g. one which only induces about 0-10% reduction in the percent of these cells relative to control).

The "epitope 2C4" is the region in the extracellular domain of ErbB2 to which the antibody 2C4 binds. In order to screen for antibodies which bind to the 2C4 epitope, a routine cross-blocking assay such as that described in *Antibodies, A Labo-*

*ratory Manual*, Cold Spring Harbor Laboratory, Ed Harlow and David Lane (1988), can be performed. Alternatively, epitope mapping can be performed to assess whether the antibody binds to the 2C4 epitope of ErbB2 (e.g. any one or more residues in the region from about residue 22 to about residue 584 of ErbB2, inclusive; see FIGS. 1A-B).

The "epitope 4D5" is the region in the extracellular domain of ErbB2 to which the antibody 4D5 (ATCC CRL 10463) binds. This epitope is close to the transmembrane domain of ErbB2. To screen for antibodies which bind to the 4D5 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to assess whether the antibody binds to the 4D5 epitope of ErbB2 (e.g. any one or more residues in the region from about residue 529 to about residue 625, inclusive; see FIGS. 1A-B).

The "epitope 3H4" is the region in the extracellular domain of ErbB2 to which the antibody 3H4 binds. This epitope includes residues from about 541 to about 599, inclusive, in the amino acid sequence of ErbB2 extracellular domain; see FIGS. 1A-B.

The "epitope 7C2/7F3" is the region at the N terminus of the extracellular domain of ErbB2 to which the 7C2 and/or 7F3 antibodies (each deposited with the ATCC, see below) bind. To screen for antibodies which bind to the 7C2/7F3 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to establish whether the antibody binds to the 7C2/7F3 epitope on ErbB2 (e.g. any one or more of residues in the region from about residue 22 to about residue 53 of ErbB2; see FIGS. 1A-B).

An "ErbB-expressing cell" is one which has ErbB protein present at its cell surface, such that an anti-ErbB2 antibody can bind thereto.

A cell "characterized by excessive activation" of an ErbB is one in which the extent of ErbB activation therein significantly exceeds the level of activation of that receptor in a normal cell of the same tissue type. Such excessive activation may result from overexpression or amplification of the ErbB and/or greater than normal levels of an ErbB ligand available for activating the ErbB in the cell. Such excessive activation may cause and/or be caused by a diseased state of the cell. In some embodiments, a sample from the patient will be subjected to a diagnostic or prognostic assay to determine whether amplification and/or overexpression of an ErbB is occurring which results in such excessive activation of the ErbB. Alternatively, or additionally, a sample from the patient may be subjected to a diagnostic or prognostic assay to determine whether amplification, overexpression and/or increased proteolytic processing of an ErbB ligand is occurring in the patient which attributes to excessive activation of the receptor. Sometimes, excessive activation of the receptor may result from an autocrine stimulatory pathway.

In an "autocrine" stimulatory pathway, self stimulation occurs by virtue of the cell producing both an ErbB ligand and its cognate ErbB. For example, the cell may express or overexpress EGFR and also express or overexpress an EGFR ligand (e.g. EGF, TGF-α, or HB-EGF). In another embodiment, the cell may express or overexpress ErbB2 and also express or overexpress a heregulin (e.g. γ-HRG).

A cell which "overexpresses" an ErbB is one which has significantly higher levels of an ErbB, such as ErbB2, at the cell surface thereof, compared to a normal cell of the same tissue type. Such overexpression may be caused by gene amplification or by increased transcription or translation. ErbB overexpression may be determined in a diagnostic or prognostic assay by evaluating increased levels of the ErbB protein present on the surface of a cell (e.g. via an immunohistochemistry assay; IHC, immunoenzyme, Western blot, ligand binding, kinase activity). Alternatively, or additionally, one may measure levels of ErbB-encoding nucleic acid in the cell, e.g. via fluorescent in situ hybridization (FISH; see WO98/45479 published October, 1998), southern blotting, or polymerase chain reaction (PCR) techniques, such as real time quantitative PCR (RT-PCR). One may also study ErbB overexpression by measuring shed antigen (e.g., ErbB extracellular domain) in a biological fluid such as serum (see, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al. *J. Immunol. Methods* 132: 73-80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

Conversely, a cell which is "not characterized by overexpression of an ErbB" is one which, in a diagnostic assay, does not express higher than normal levels of ErbB compared to a normal cell of the same tissue type.

A cell which "overexpresses" an ErbB ligand is one which produces significantly higher levels of that ligand compared to a normal cell of the same tissue type. Such overexpression may be caused by gene amplification or by increased transcription or translation. Overexpression of the ErbB ligand may be determined diagnostically by evaluating levels of the ligand (or nucleic acid encoding it) in the patient, e.g. in a biopsy or by various diagnostic assays such as the IHC, immunoenzyme, Western blot, ligand binding, FISH, southern blotting, PCR or in vivo assays described above.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and docetaxel (TAXOTERE®, Rhône-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on cells such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

An "anti-angiogenic agent" refers to a compound which blocks, or interferes with to some degree, the development of blood vessels. The anti-angiogenic factor may, for instance, be a small molecule or antibody that binds to a growth factor or growth factor receptor involved in promoting angiogenesis. The preferred anti-angiogenic factor herein is an antibody that binds to Vascular Endothelial Growth Factor (VEGF), such as the recombinant humanized anti-VEGF antibody AVASTIN® (Genentech).

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ, colony stimulating factors (CSFs) such as macrophage-CSF (M-CSF); granulocyte-macrophage-CSF (GM-CSF); and granulocyte-CSF (G-CSF); interleukins (Ms) such as IL-1, IL-1α, IL-2, IL-3, IL-4, IL-5, IL-6, IL-7, IL-8, IL-9, IL-10, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "package insert" is used to refer to instructions customarily included in commercial packages of therapeutic products, that contain information about the indications, usage, dosage, administration, contraindications and/or warnings concerning the use of such therapeutic products.

A "cardioprotectant" is a compound or composition which prevents or reduces myocardial dysfunction (i.e. cardiomyopathy and/or congestive heart failure) associated with administration of a drug, such as an anthracycline antibiotic and/or an anti-ErbB2 antibody, to a patient. The cardioprotectant may, for example, block or reduce a free-radical-mediated cardiotoxic effect and/or prevent or reduce oxidative-stress injury. Examples of cardioprotectants encompassed by the present definition include the iron-chelating agent dexrazoxane (ICRF-187) (Seifert et al. *The Annals of Pharmacotherapy* 28:1063-1072 (1994)); a lipid-lowering agent and/or anti-oxidant such as probucol (Singal et al. *J. Mol. Cell. Cardiol.* 27:1055-1063 (1995)); amifostine (aminothiol 2-[(3-aminopropyl)amino]ethanethiol-dihydrogen phosphate ester, also called WR-2721, and the dephosphorylated cellular uptake form thereof called WR-1065) and S-3-(3-methylaminopropylamino)propylphosphorothioic acid (WR-151327), see Green et al. *Cancer Research* 54:738-741 (1994); digoxin (Bristow, M. R. In: Bristow M R, ed. *Drug-Induced Heart Disease*. New York: Elsevier 191-215 (1980)); beta-blockers such as metoprolol (Hjalmarson et al. *Drugs* 47:Suppl 4:31-9 (1994); and Shaddy et al. *Am. Heart J.* 129:197-9 (1995)); vitamin E; ascorbic acid (vitamin C); free radical scavengers such as oleanolic acid, ursolic acid and N-acetylcysteine (NAC); spin trapping compounds such as alpha-phenyl-tert-butyl nitrone (PBN); (Paracchini et al., *Anticancer Res.* 13:1607-1612 (1993)); selenoorganic compounds such as P251 (Elbesen); and the like.

II. Detailed Description

The ErbB (HER) family of transmembrane tyrosine kinase receptors is composed of four members, ErbB1 (HER1, EGFR); ErbB2 (HER2 or p185$^{neu}$), ErbB3 (HER3) and ErbB4 (HER4 or tyro2).

ErbB2/HER2/p185$^{neu}$ and ErbB1/EGFR are significantly over-expressed in most epithelial malignancies, including breast cancer, head and neck cancer, stomach cancer, prostate cancer, ovarian cancer, pancreatic cancer, lung cancer bladder, as well as glioblastomas. HER2 amplifies the signal provided by other receptors of the HER family by forming heterodimers. The essential role of HER2 in the HER signaling network led to the development of anti-HER2 monoclonal antibodies (MAbs) for cancer therapy. In particular, a humanized anti-ErbB2 MAb (transtuzumab, Herceptin®, Genentech, Inc.) is widely used for the treatment of women with HER2 overexpressing breast cancers. Trastuzumab induces HER2 receptor downmodulation and, as a result, inhibits critical signalling pathways (i.e. ras-Raf-MAPK and PI3K/

Akt) and blocks cell cycle progression by inducing the formation of p27/Cdk2 complexes. Trastuzumab also inhibits HER2 cleavage, preceding antibody-induced receptor downmodulation, which effect might contribute to its antitumor activity in some cancers. In vivo, trastuzumab inhibits angiogenesis and induces antibody-dependent cellular cytotoxicity. HER2 is known to form heterodimers with HER1 (EGFR), HER3 or HER4. A humanized monoclonal antibody, called 2C4, is in clinical development for cancer treatment. 2C4 binds to a different epitope of HER2 ectodomain than trastuzumab and sterically hinders HER2 recruitment in heterodimers with other HER receptors. This results in the inhibition of signalling by HER2-based heterodimers both in cells with low and high HER2 expression. In vitro and in vivo antitumor activity has been reported in a range of breast and prostate tumor models. Small-molecule anti-HER2/neu peptidomimetics (ARNP) have also been developed and tested for efficacy in cancer therapy (Zhang et al., *Drug News Perspect.* 13(6):325-9 (2000).

The present invention is, at least partially, based on the unexpected finding that ErbB antagonists exhibit analgesic effects and are, therefore, useful in the management of pain, including chronic pain, such as cancer-related pain. In particular, prostate cancer patients treated with the humanized anti-ErbB2 antibody 2C4 recorded less pain and reduced analgesia even when their PSA value was not reduced. Similarly, the analgesic effect of the humanized 2C4 antibody was observed during the treatment of liposarcoma.

Therefore, in its broadest aspect, the invention relates to pain management using ErbB antagonists. In particular, the invention concerns the management of pain, including acute and chronic pain, either cancer related or not associated with cancer, with ErbB antagonists. The invention concerns the treatment of any type of pain, including, without limitation, nociceptive pain, somatic pain, visceral pain, neuropathic pain, centrally generated pain (including deafferentiation pain and sympathetically maintained pain), and peripherally generated pain (including painful polyneuropathies and painful mononeuropethies).

ErbB Antagonists

The ErbB antagonists of the present invention are molecules that block (reduce or prevent) a biological activity of one or more ErbB(s). Preferably, the antagonist blocks (reduces or prevents) ligand activation of an ErbB. In a particular embodiment, the ErbB antagonists of the present invention inhibit a biological activity mediated by an ErbB2 (HER2) and/or ErbB1 (EGFR) receptor or a receptor complex comprising such receptor(s).

The ErbB antagonists herein include, without limitation, polypeptides (including antibodies and antibody fragments), peptides, peptide mimetics, non-peptide small organic molecules, antisense molecules, and oligonucleotide decoy molecules.

Small organic molecules that compete with ATP binding to the kinase pocket of EGFR are reviewed, for example, by Arteaga CL., *Exp. Cell. Res.* 284(1):122-30 (2003). A small molecule EGFR inhibitor, Iressa™ (ZD1839, gefinitib, Aztra-Zeneca) is described, for example, in Kris M et al. *JAMA*, 290(16):2149-2158 (2003). Further small molecule EGFR antagonists include CP-358,774 (TARCEVA; Genentech/OSI) and AG1478, AG1571 (SU 5271; Sugen).

Anti-EGFR antibodies are also known in the art and include, for example, Erbitux® (IMC-C225, cetuximab, ImClone) a chimeric anti-EGFR MAb, and reshaped human 225 (H225) (see, WO 96/40210, ImClone Systems Inc.). Further examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, humanized and chimeric antibodies that bind EGFR as described in U.S. Pat. No. 5,891,996, and human antibodies that bind EGFR, such as ABX-EGF (see WO98/50433, Abgenix). The anti-EGFR antibody may be conjugated with a cytotoxic agent, thus generating an immunoconjugate (see, e.g., EP659,439A2, Merck Patent GmbH).

CP-654577 (Pfizer) a selective inhibitor of ErbB2 relative to EGFR tyrosine kinase, is disclosed, for example, in Barbacci et al., *Cancer Res.* 63(15):4450-9 (2003). A small molecule form of anti-ErbB2 peptidomimetic is described by Zhang et al., *Drug Nes Perspect* 13(6):325-9 (2000).

Identification of ErbB Antagonists

New agents that target and inhibit a biological activity of ErbB receptors, such as EGFR and/or ErbB2, can be identified by methods known in the art.

In general, the first step in identifying new ErbB antagonists is in vitro screening followed by in vivo assays in an appropriate animal model and ultimately human clinical trials.

To identify compounds that bind to an ErbB receptor or receptor complex, receptor-binding tests can be performed using ErbB receptors or receptor complexes isolated from their respective native sources, or produced by recombinant DNA technology and/or chemical synthesis. The binding affinity of the candidate compounds can be tested by direct binding or by indirect, e.g. competitive, binding. In competitive binding experiments, the concentration of a compound necessary to displace 50% of another compound bound to the receptor ($IC_{50}$) is usually used as a measure of binding affinity.

In another method, in order to identify novel ErbB antagonists, DNA encoding the sequence encoding the target ErbB receptor (e.g. ErbB2 or EGFR) is cloned into an expression vector containing a selectable marker. The vector is used to transfect recombinant host cells. Following several rounds of selection stable lines which express the ErbB receptor are identified. New ErbB antagonists can then be identified by virtue of their ability to compete effectively with a known inhibitor of the target ErbB receptor. Binding coefficients can be determined by any known manner, e.g. by Scatchard analysis.

Binding experiments can also be performed using cells or cell lines known to express the target ErbB receptor.

To identify a candidate molecule which blocks ligand activation of an ErbB, the ability of the molecule to block ErbB ligand binding to cells expressing the ErbB (e.g. in conjugation with another ErbB with which the ErbB of interest forms an ErbB hetero-oligomer) may be determined. For example, cells naturally expressing, or transfected to express, ErbBs of the ErbB hetero-oligomer may be incubated with the candidate molecule and then exposed to labeled ErbB ligand. The ability of the candidate molecule to block ligand binding to the ErbB in the ErbB hetero-oligomer may then be evaluated.

Alternatively, or additionally, the ability of a candidate molecule to block ErbB ligand-stimulated tyrosine phosphorylation of an ErbB present in an ErbB hetero-oligomer may be assessed. For example, cells endogenously expressing the ErbBs or transfected to expressed them may be incubated with the candidate molecule and then assayed for ErbB ligand-dependent tyrosine phosphorylation activity using an anti-phosphotyrosine monoclonal (which is optionally conjugated with a detectable label). The kinase receptor activation assay described in U.S. Pat. No. 5,766,863 is also available for determining ErbB activation and blocking of that activity by an antagonist.

One may also assess the growth inhibitory effects of a candidate molecule on MDA-MB-175 cells, e.g., essentially as described in Schaefer et al. *Oncogene* 15:1385-1394 (1997). According to this assay, MDA-MB-175 cells may treated with a candidate antagonist and stained with crystal violet. Incubation with a candidate antagonist may show a growth inhibitory effect on this cell line similar to that displayed by monoclonal antibody 2C4. In a further embodiment, exogenous HRG will not significantly reverse this inhibition. Preferably, the antagonist will be able to inhibit cell proliferation of MDA-MB-175 cells to a greater extent than monoclonal antibody 4D5 (and optionally to a greater extent than monoclonal antibody 7F3), both in the presence and absence of exogenous HRG.

In one embodiment, the antagonist may block heregulin dependent association of ErbB2 with ErbB3 in both MCF7 and SK-BR-3 cells as determined in a co-immunoprecipitation experiment such as that described in Example 2 substantially more effectively than monoclonal antibody 4D5, and preferably substantially more effectively than monoclonal antibody 7F3.

To identify antagonists with growth inhibitory properties, one may screen for antibodies which inhibit the growth of cancer cells which overexpress ErbB2.

To select for antagonists which induce cell death, loss of membrane integrity as indicated by, e.g., PI, trypan blue or 7AAD uptake may be assessed relative to control. The preferred assay is the PI uptake assay using BT474 cells. Details of this assay will be provided hereinafter, with particular reference to antibodies.

In order to select for antagonists which induce apoptosis, for example an annexin binding assay using BT474 cells or a DNA staining assay using BT 474 cells can be used, These assays will be described in detail hereinbelow, with reference to antibodies with apoptotic properties.

According to a further approach, ErbB2 and EGFR antagonists are identified by correlating EGFR, TGF-α (a ligand for EGFR), and ErbB2 mRNA expression levels with the results of cytotoxicity assays of the 49000 compounds in the National Cancer Institute (NCI) drug screen database (Wosikowski et al., *J. Natl. Cancer Inst.* 89(20):1505-15 (1997)).

After determining the inhibition of a target biological activity in an in vitro assay, the ability of a candidate antagonist to control pain can be tested in in vivo models of pain.

In a preferred embodiment, the analgesic activity of a candidate ErbB antagonist is tested in an animal model used in pain research.

Animal Models of Pain (i) Noxious Pain

A suitable animal model of noxious pain is the "tail flick" test (Bass and Wanderbrook, *J. Am. Pharm. Assoc. Sci. Ed.* 41:569-70 (1952)) This method is based on measuring pain sensitivity in mice or rats as they respond to the application of heat to a small area of their tails with or without administration of a candidate ErbB antagonist. The test is based on measuring the withdrawal time of the tail following application of radiant heat, and can be performed by using commercially available equipment, such as, for example, the Tail Flick Analgesia Meter (SDI, San Diego, Calif.).

Another animal model of noxious pain is the "hot plate paw-licking" test. In this test, animals (rats or mice) are individually placed on a hot plate. The latency to first sign of hind paw licking is taken or jump response is taken as an index of nociceptive threshold. The effect of drug administration on this threshold is considered to be an index of analgesic response. (O'Callaghan and Holzman, *J. Pharmaceol.* *Exp. Ther.* 192:497-505 (1975)). The route of drug administration may differ but typically is subcutaneous.

The paw-pressure, or mechanical hyperalgesia, test uses a pressure of increasing intensity applied to a punctiform area on the hindpaw or, less commonly, on the tail. In practice, the paw or tail is placed between a plane surface and a blunt, plastic-coated point mounted on top of a system of cogwheels, with a cursor that can be displaced along the length of a graduated beam (Green et al., *Br. J. Pharmacol.* 6:572-85 (1957) for an automated readout. The application of increasing pressure is interrupted when the animal removes its tail, an action that is read out as force in grams for the threshold of response.

Chemical stimuli can also be used to model noxious pain in animals. Typically the chemical agents are administered intradermally or intraperitoneally. For example, in the formalin (paw) test usually a 0.5 to 15% (generally about 3.5%) solution of formalin is injected into the dorsal or plantar surface of the rat fore- or hindpaw, and produces a painful response of increasing and decreasing intensity for about 60 minutes. Typical responses include paw lifting, licking, nibbling or shaking, which can be monitored in the absence and presence of a test substance (Lariviere and Melzack, *Pain* 66:271-7 (1996)).

(ii) Visceral Pain

Visceral pain is typically tested by intraperitoneal injections of irritants (Writhing Test), such as, for example, acetic acid/ethacrinic acid or phenylbenzoquinone. The agents provoke a stereotypical response in rodents, characterized by abdominal contractions, whol ebody movements, contortions of the abdominal muscles, reduced motor activity and incoordination. These responses are considered indicative of visceral pain associated with visceral chemoreceptors. The writhing test has been successfully used to predict effective analgesic doses for treatment of humans (Dubinsky et al., *Agents Actions* 20:50-60 (1987)).

(iii) Inflammatory Pain

Inflammatory pain is typically modeled using p-benzoquinone-induced Writhing Test or the carrageean-induced hind paw edema model (DiRosa et al., *J. Pathol.* 101:15-29 (1971)).

In another animal model of inflammatory pain, intradermal injection of capsaicin is used to neurogenic inflammation and hyperalgesia. Originally, response was observed and quantitated by visual inspection However, recent developments in thermography and laser-Doppler Flowmetry have proved to be invaluable tools in quantitating neurogenic inflammation and inflammatory responses. For further details see, e.g. Sumikura et al., *Pain* 105(285-291 (2003).

(iv) Licking, Scratching and Biting Responses

Such responses can be induced, for example, by TNF-α (typically 100 pg), IFN-γ (typically 100 pg), or IL-1β (typically 100 pg) injected intratracheally (i.t.), especially at higher dose (3 g/kg). In addition, similar responses can be elicited by i.t. injections of glutamate (20 µg), N-methyl-D-aspartic acid (50 ng), α-amino-3-hydroxy-5-methylisoxazole-4-proprionic acid (13 ng) or kainic acid, or by administration for substance P or capsaicin.

(v) Neuropathic Pain

Chronic constriction injury (CCI) of the sciatic nerve in rats induces persistent mechanical hyperalgesia and allodyinia, and is a widely used model of neuropathic pain (Bennett and Xie, *Pain* 33:87-107 (1988)).

(vi) Cancer Pain

Candidate agents for the treatment of cancer pain can be tested in the above-listed animals models of acute and chronic pain or inflammatory pain. In addition, there are several animal models available that have been specifically designed to test cancer pain.

For example, a candidate ErbB antagonist can be tested in a murine model of bone cancer pain, as described in Menendez et al., *Brain Res.* 969(102):102-9 (2003). This test investigated the reactivity to noxious heat of C3G/HeJ mice receiving an intratibial (i.t.) injection of NCTC 2472 cells. NCTC2472 cells are able to induce osteosarcoma, and break through bone into soft tissues about two weeks after inoculation, producing a macroscopical increase of the limb size from the fourth week. Thermal reactivity is diminished during the first two weeks after cell implantation, and this hyperalgesia is reversed by the administration of naloxone (10 mg/kg). According to the authors, during the fourth and fifth weeks after NCTC 2472 cell implantation, an increased nociceptive heat reactivity, instead of hypoalgesia, was observed. This hyperalgesia was prevented by the systemic administration of morphine (15 mg/kg). This animal model of bone cancer pain can be used to identify and study new agents, such as ErbB antagonists for the management of bone cancer pain, and potentially cancer pain in general.

Similarly, the effect of candidate ErbB antagonists on cancer pain can be studied in tumor implanted mice, as described by Wacnik et al., *Pain* 101(1-2):175-86 (2003).

A mouse model of neuropathic cancer pain has been developed by Shimoyama et al., *Pain* 99(1-2):167-74 (2002). In this model, Meth A sarcoma cells were inoculated to the immediate proximity of the scietic nerve in BALB/c mice. The growing tumor gradually compresses the nerve, thereby causing nerve injury. Time courses of thermal hyperalgesia and mechanical sensitivity to von Frey hairs are determined and signs of spontaneous pain are evaluated.

An example of using mutant mice for pain threshold research is described by Guilherme et al., *Nature Neurosci.* 6:221-222 (2003).

For a general overview of common animal models for pain see, e.g. Eaton, M., *J. of Rehabilitation Research and Development* 40(4) Suppl. 1:41-54 (2003).

Human Clinical Trials

Pain measurement is essential for assessing analgesia. In human clinical trials, the pain experienced by an individual patient is assessed by using one or more of the known measures of pain, including a Visual Analog Scale (VAS), descriptive scale, numeric scale, Health Assessment Questionare (HAQ) pain index, and the like. A workshop sponsored by the Initiative on Methods, Measurement, and Pain Assessment in Clinical Trials (IIVIMPACT) described six consensus domains recommended to be included in all chronic pain trials (Turk et al., *Pain,* 106(3):337-45 (2003)).

Most frequently, pain is assessed using a VAS recorded on various scales, such as a scale of 0 to 100, or 0 to 10, where the lowest score represents no pain, and the highest score represents the worst possible pain. Since it has been reported that patients have difficulty discriminating 100 levels of pain, the most frequently used VAS system operates on a scale of 0 to 10 (Miller, G A, *Psychological Review* 63:81-97 (1956).

The descriptive scale typically includes the following descriptions: no pain, mild pain, moderate pain, severe pain, very severe pain, and worst possible pain.

In a preferred embodiment, the ErbB antagonists of the present invention are anti-ErbB2 antibodies.

Production of Anti-ErbB2 Antibodies

A description follows as to exemplary techniques for the production of the antibodies used in accordance with the present invention. The ErbB2 antigen to be used for production of antibodies may be, e.g., a soluble form of the extracellular domain of ErbB2 or a portion thereof, containing the desired epitope. Alternatively, cells expressing ErbB2 at their cell surface (e.g. NIH-3T3 cells transformed to overexpress ErbB2; or a carcinoma cell line such as SK-BR-3 cells, see Stancovski et al. *PNAS (USA)* 88:8691-8695 (199.1)) can be used to generate antibodies. Other forms of ErbB2 useful for generating antibodies will be apparent to those skilled in the art.

(i) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies

Monoclonal antibodies are obtained from a population of substantially homogeneous antibodies, i.e., the individual antibodies comprising the population are identical except for variants that may arise during the production of the antibody. Thus, the modifier "monoclonal" indicates the character of the antibody as not being a mixture of discrete antibodies.

For example, the monoclonal antibodies may be made using the hybridoma method first described by Kohler et al., *Nature,* 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); and Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional antibody purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.*, 130: 151-188 (1992).

In a further embodiment, monoclonal antibodies or antibody fragments can be isolated from antibody phage libraries generated using the techniques described in McCafferty et al., *Nature*, 348:552-554 (1990). Clackson et al., *Nature*, 352: 624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy chain and light chain constant domains in place of the homologous murine sequences (U.S. Pat. No. 4,816,567; and Morrison, et al., *Proc. Natl. Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iii) Humanized Antibodies

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., *J. Immunol.*, 151:2296 (1993); Chothia et al., *J. Mol. Biol.*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Example 3 below describes production of exemplary humanized anti-ErbB2 antibodies which bind ErbB2 and block ligand activation of an ErbB. The humanized antibody of particular interest herein blocks EGF, TGF-α and/or HRG mediated activation of MAPK essentially as effectively as murine monoclonal antibody 2C4 (or a Fab fragment thereof) and/or binds ErbB2 essentially as effectively as murine monoclonal antibody 2C4 (or a Fab fragment thereof). The humanized antibody herein may, for example, comprise non-human hypervariable region residues incorporated into a human variable heavy domain and may further comprise a framework region (FR) substitution at a position selected from the group consisting of 69H, 71H and 73H utilizing the variable domain numbering system set forth in Kabat et al., *Sequences of Proteins of Immunological Interest*, 5th Ed. Public Health Service, National Institutes of Health, Bethesda, Md. (1991). In one embodiment, the humanized antibody comprises FR substitutions at two or all of positions 69H, 71H and 73H.

An exemplary humanized antibody of interest herein comprises variable heavy domain complementarity determining residues GFTFTDYTMX, where X is preferably D or S (SEQ ID NO:7); DVNPNSGGSIYNQRFKG (SEQ ID NO:8); and/or NLGPSFYFDY (SEQ ID NO:9), optionally comprising amino acid modifications of those CDR residues, e.g. where the modifications essentially maintain or improve affinity of the antibody. For example, the antibody variant of interest may have from about one to about seven or about five amino acid substitutions in the above variable heavy CDR sequences. Such antibody variants may be prepared by affinity maturation, e.g., as described below. The most preferred humanized antibody comprises the variable heavy domain amino acid sequence in SEQ ID NO:4.

The humanized antibody may comprise variable light domain complementarity determining residues KASQD-VSIGVA (SEQ ID NO:10); SASYX$^1$X$^2$X$^3$, where X$^1$ is preferably R or L, X$^2$ is preferably Y or E, and X$^3$ is preferably T or S (SEQ ID NO:11); and/or QQYYIYPYT (SEQ ID NO:12), e.g. in addition to those variable heavy domain CDR residues in the preceding paragraph. Such humanized antibodies optionally comprise amino acid modifications of the above CDR residues, e.g. where the modifications essentially maintain or improve affinity of the antibody. For example, the antibody variant of interest may have from about one to about seven or about five amino acid substitutions in the above variable light CDR sequences. Such antibody variants may be prepared by affinity maturation, e.g., as described below. The most preferred humanized antibody comprises the variable light domain amino acid sequence in SEQ ID NO:3.

The present application also contemplates affinity matured antibodies which bind ErbB2 and block ligand activation of an ErbB. The parent antibody may be a human antibody or a humanized antibody, e.g., one comprising the variable light and/or heavy sequences of SEQ ID Nos. 3 and 4, respectively (i.e. variant 574). The affinity matured antibody preferably binds to ErbB2 receptor with an affinity superior to that of murine 2C4 or variant 574 (e.g. from about two or about four fold, to about 100 fold or about 1000 fold improved affinity, e.g. as assessed using a ErbB2-extracellular domain (ECD) ELISA). Exemplary variable heavy CDR residues for substitution include H28, H30, H34, 1135, H64, H96, H99, or combinations of two or more (e.g. two, three, four, five, six, or seven of these residues). Examples of variable light CDR residues for alteration include L28, L50, L53, L56, L91, L92, L93, L94, L96, L97 or combinations of two or more (e.g. two to three, four, five or up to about ten of these residues).

Various forms of the humanized antibody or affinity matured antibody are contemplated. For example, the humanized antibody or affinity matured antibody may be an antibody fragment, such as a Fab, which is optionally conjugated with one or more cytotoxic agent(s) in order to generate an immunoconjugate. Alternatively, the humanized antibody or affinity matured antibody may be an intact antibody, such as an intact IgG1 antibody.

(iv) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggemann et al., *Year in Immuno.*, 7:33 (1993); and U.S. Pat. Nos. 5,591,669, 5,589,369 and 5,545,807.

Alternatively, phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson, Kevin S, and Chiswell, David J., *Current Opinion in Structural Biology* 3:564-571 (1993). Several sources of V-gene segments can be used for phage display. Clackson et al., *Nature*, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

Human anti-ErbB2 antibodies are described in U.S. Pat. No. 5,772,997 issued Jun. 30, 1998; WO 97/00271 published Jan. 3, 1997; and WO01/09187 published Feb. 8, 2001 (Medarex).

(v) Antibody Fragments

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science*, 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. The antibody fragment may also be a "linear antibody", e.g., as described in U.S. Pat. No. 5,641,870 for example. Such linear antibody fragments may be monospecific or bispecific. Single chain intracellular antibodies (sFv) that bind ErbB2 are described in WO01/56604 and U.S. Pat. No. 6,028,059.

(vi) Bispecific Antibodies

Bispecific antibodies are antibodies that have binding specificities for at least two different epitopes. Exemplary bispecific antibodies may bind to two different epitopes of the ErbB2 protein. Other such antibodies may combine an ErbB2 binding site with binding site(s) for EGFR, ErbB3 and/or ErbB4. Alternatively, an anti-ErbB2 arm may be combined with an arm which binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the ErbB2-expressing cell. Bispecific antibodies may also be used to localize cytotoxic agents to cells which express ErbB2. These antibodies possess an ErbB2-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. F(ab')$_2$ bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the coexpression of two immunoglobulin heavy chain-light chain pairs, where the two chains have different specificities (Milstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991). U.S. Pat. No. 6,270,765B1 published Aug. 7, 2001 describes trispecific antibodies that bind ErbB2, EGFR and FcR.

(vii) Other Amino Acid Sequence Modifications

Amino acid sequence modification(s) of the anti-ErbB2 antibodies described herein are contemplated. For example, it may be desirable to improve the binding affinity and/or other biological properties of the antibody. Amino acid sequence variants of the anti-ErbB2 antibody are prepared by introducing appropriate nucleotide changes into the anti-ErbB2 antibody nucleic acid, or by peptide synthesis. Such modifications include, for example, deletions from, and/or insertions into and/or substitutions of, residues within the amino acid sequences of the anti-ErbB2 antibody. Any combination of deletion, insertion, and substitution is made to arrive at the final construct, provided that the final construct possesses the desired characteristics. The amino acid changes also may alter post-translational processes of the anti-ErbB2 antibody, such as changing the number or position of glycosylation sites.

A useful method for identification of certain residues or regions of the anti-ErbB2 antibody that are preferred locations for mutagenesis is called "alanine scanning mutagenesis" as described by Cunningham and Wells *Science,* 244: 1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with ErbB2 antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed anti-ErbB2 antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-ErbB2 antibody with an N-terminal methionyl residue or the antibody fused to a cytotoxic polypeptide. Other insertional variants of the anti-ErbB2 antibody molecule include the fusion to the—or C-terminus of the anti-ErbB2 antibody to an enzyme (e.g. for ADEPT) or a polypeptide which increases the serum half-life of the antibody.

Another type of variant is an amino acid substitution variant. These variants have at least one amino acid residue in the anti-ErbB2 antibody molecule replaced by a different residue. The sites of greatest interest for substitutional mutagenesis include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | Ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | Ala | ala |
| Ser (S) | Thr | thr |
| Thr (T) | Ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the anti-ErbB2 antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human ErbB2. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceyl-galactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-ErbB2 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-ErbB2 antibody.

It may be desirable to modify the antibody of the invention with respect to effector function, e.g. so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989).

Antibody variants with altered Fc region sequence and improved or diminished C1q binding are described in WO99/51642. Antibody variants with altered Fc region sequences and altered FcR binding function are described in WO00/42072.

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

(viii) Screening for Antibodies with the Desired Properties

Techniques for generating antibodies have been described above. One may further select antibodies with certain biological characteristics, as desired.

To identify an antibody which blocks ligand activation of an ErbB, the ability of the antibody to block ErbB ligand binding to cells expressing the ErbB (e.g. in conjugation with another ErbB with which the ErbB of interest forms an ErbB hetero-oligomer) may be determined. For example, cells naturally expressing, or transfected to express, ErbBs of the ErbB hetero-oligomer may be incubated with the antibody and then exposed to labeled ErbB ligand. The ability of the anti-ErbB2 antibody to block ligand binding to the ErbB in the ErbB hetero-oligomer may then be evaluated.

For example, inhibition of HRG binding to MCF7 breast tumor cell lines by anti-ErbB2 antibodies may be performed using monolayer MCF7 cultures on ice in a 24-well-plate format essentially as described in Example 1 below. Anti-ErbB2 monoclonal antibodies may be added to each well and incubated for 30 minutes. $^{125}$I-labeled $rHRG\beta 1_{177-224}$ (25 pm) may then be added, and the incubation may be continued for 4 to 16 hours. Dose response curves may be prepared and an $IC_{50}$ value may be calculated for the antibody of interest. In one embodiment, the antibody which blocks ligand activation of an ErbB will have an $IC_{50}$ for inhibiting HRG binding to MCF7 cells in this assay of about 50 nM or less, more preferably 10 nM or less. Where the antibody is an antibody fragment such as a Fab fragment, the $IC_{50}$ for inhibiting HRG binding to MCF7 cells in this assay may, for example, be about 100 nM or less, more preferably 50 nM or less. Other, non-antibody, ErbB antagonist candidates can be tested in a similar manner.

Alternatively, or additionally, the ability of the anti-ErbB2 antibody to block ErbB ligand-stimulated tyrosine phosphorylation of an ErbB present in an ErbB hetero-oligomer may be assessed. For example, cells endogenously expressing the ErbBs or transfected to expressed them may be incubated with the antibody and then assayed for ErbB ligand-dependent tyrosine phosphorylation activity using an anti-phosphotyrosine monoclonal (which is optionally conjugated with a detectable label). The kinase receptor activation assay described in U.S. Pat. No. 5,766,863 is also available for determining ErbB activation and blocking of that activity by an antibody.

In one embodiment, one may screen for an antibody which inhibits HRG stimulation of p180 tyrosine phosphorylation in MCF7 cells essentially as described in Example 1 below. For example, the MCF7 cells may be plated in 24-well plates and monoclonal antibodies to ErbB2 may be added to each well and incubated for 30 minutes at room temperature; then $rHRG\beta1_{177-244}$ may be added to each well to a final concentration of 0.2 nM, and the incubation may be continued for 8 minutes. Media may be aspirated from each well, and reactions may be stopped by the addition of 100 µl of SDS sample buffer (5% SDS, 25 mM DTT, and 25 mM Tris-HCl, pH 6.8). Each sample (25 µl) may be electrophoresed on a 4-12% gradient gel (Novex) and then electrophoretically transferred to polyvinylidene difluoride membrane. Antiphosphotyrosine (at 1 µg/ml) immunoblots may be developed, and the intensity of the predominant reactive band at $M_r$~180,000 may be quantified by reflectance densitometry. The antibody selected will preferably significantly inhibit HRG stimulation of p180 tyrosine phosphorylation to about 0-35% of control in this assay. A dose-response curve for inhibition of HRG stimulation of p180 tyrosine phosphorylation as determined by reflectance densitometry may be prepared and an $IC_{50}$ for the antibody of interest may be calculated. In one embodiment, the antibody which blocks ligand activation of an ErbB will have an $IC_{50}$ for inhibiting HRG stimulation of p180 tyrosine phosphorylation in this assay of about 50 nM or less, more preferably 10 nM or less. Where the antibody is an antibody fragment such as a Fab fragment, the $IC_{50}$ for inhibiting HRG stimulation of p180 tyrosine phosphorylation in this assay may, for example, be about 100 nM or less, more preferably 50 nM or less.

One may also assess the growth inhibitory effects of the antibody on MDA-MB-175 cells, e.g, essentially as described in Schaefer et al. *Oncogene* 15:1385-1394 (1997). According to this assay, MDA-MB-175 cells may treated with an anti-ErbB2 monoclonal antibody (10 µg/mL) for 4 days and stained with crystal violet. Incubation with an anti-ErbB2 antibody may show a growth inhibitory effect on this cell line similar to that displayed by monoclonal antibody 2C4. In a further embodiment, exogenous HRG will not significantly reverse this inhibition. Preferably, the antibody will be able to inhibit cell proliferation of MDA-MB-175 cells to a greater extent than monoclonal antibody 4D5 (and optionally to a greater extent than monoclonal antibody 7F3), both in the presence and absence of exogenous HRG.

In one embodiment, the anti-ErbB2 antibody of interest may block heregulin dependent association of ErbB2 with ErbB3 in both MCF7 and SK-BR-3 cells as determined in a co-immunoprecipitation experiment such as that described in Example 2 substantially more effectively than monoclonal antibody 4D5, and preferably substantially more effectively than monoclonal antibody 7F3.

To identify growth inhibitory anti-ErbB2 antibodies, one may screen for antibodies which inhibit the growth of cancer cells which overexpress ErbB2. In one embodiment, the growth inhibitory antibody of choice is able to inhibit growth of SK-BR-3 cells in cell culture by about 20-100% and preferably by about 50-100% at an antibody concentration of about 0.5 to 30 µg/ml. To identify such antibodies, the SK-BR-3 assay described in U.S. Pat. No. 5,677,171 can be performed. According to this assay, SK-BR-3 cells are grown in a 1:1 mixture of F12 and DMEM medium supplemented with 10% fetal bovine serum, glutamine and penicillin streptomycin. The SK-BR-3 cells are plated at 20,000 cells in a 35 mm cell culture dish (2 mls/35 mm dish). 0.5 to 30 µg/ml of the anti-ErbB2 antibody is added per dish. After six days, the number of cells, compared to untreated cells are counted using an electronic COULTER□ cell counter. Those antibodies which inhibit growth of the SK-BR-3 cells by about 20-100% or about 50-100% may be selected as growth inhibitory antibodies.

To select for antibodies which induce cell death, loss of membrane integrity as indicated by, e.g., PI, trypan blue or 7AAD uptake may be assessed relative to control. The preferred assay is the PI uptake assay using BT474 cells. According to this assay, BT474 cells (which can be obtained from the American Type Culture Collection (Rockville, Md.)) are cultured in Dulbecco's Modified Eagle Medium (D-MEM): Ham's F-12 (50:50) supplemented with 10% heat-inactivated FBS (Hyclone) and 2 mM L-glutamine. (Thus, the assay is performed in the absence of complement and immune effector cells). The BT474 cells are seeded at a density of $3 \times 10^6$ per dish in 100×20 mm dishes and allowed to attach overnight. The medium is then removed and replaced with fresh medium alone or medium containing 10 µg/ml of the appropriate monoclonal antibody. The cells are incubated for a 3 day time period. Following each treatment, monolayers are washed with PBS and detached by trypsinization. Cells are then centrifuged at 1200 rpm for 5 minutes at 4° C., the pellet resuspended in 3 ml ice cold $Ca^{2+}$ binding buffer (10 mM Hepes, pH 7.4, 140 mM NaCl, 2.5 mM $CaCl_2$) and aliquoted into 35 mm strainer-capped 12×75 tubes (1 ml per tube, 3 tubes per treatment group) for removal of cell clumps. Tubes then receive PI (10 µg/ml). Samples may be analyzed using a FACSCAN® flow cytometer and FACSCONVERT® CellQuest software (Becton Dickinson). Those antibodies which induce statistically significant levels of cell death as determined by PI uptake may be selected as cell death-inducing antibodies.

In order to select for antibodies which induce apoptosis, an annexin binding assay using BT474 cells is available. The BT474 cells are cultured and seeded in dishes as discussed in the preceding paragraph. The medium is then removed and replaced with fresh medium alone or medium containing 10 µg/ml of the monoclonal antibody. Following a three day incubation period, monolayers are washed with PBS and detached by trypsinization. Cells are then centrifuged, resuspended in $Ca^{2+}$ binding buffer and aliquoted into tubes as discussed above for the cell death assay. Tubes then receive labeled annexin (e.g. annexin V-FTIC) (1 µg/ml). Samples may be analyzed using a FACSCAN® flow cytometer and FACSCONVERT® CellQuest software (Becton Dickinson).

Those antibodies which induce statistically significant levels of annexin binding relative to control are selected as apoptosis-inducing antibodies.

In addition to the annexin binding assay, a DNA staining assay using BT474 cells is available. In order to perform this assay, BT474 cells which have been treated with the antibody of interest as described in the preceding two paragraphs are incubated with 9 μg/ml HOECHST 33342® for 2 hr at 37° C., then analyzed on an EPICS ELITE® flow cytometer (Coulter Corporation) using MODFIT LT® software (Verity Software House). Antibodies which induce a change in the percentage of apoptotic cells which is 2 fold or greater (and preferably 3 fold or greater) than untreated cells (up to 100% apoptotic cells) may be selected as pro-apoptotic antibodies using this assay.

To screen for antibodies which bind to an epitope on ErbB2 bound by an antibody of interest, a routine cross-blocking assay such as that described in *Antibodies, A Laboratory Manual*, Cold Spring Harbor Laboratory, Ed Harlow and David Lane (1988), can be performed. Alternatively, or additionally, epitope mapping can be performed by methods known in the art (see, e.g. FIGS. 1A and 1B herein).

The antibodies identified as antagonists can then be tested in any of the animal models of pain discussed above.

(ix) Immunoconjugates

The ErbB antagonist antibodies of the invention can also be in the form of immunoconjugates comprising an antibody conjugated to a cytotoxic agent such as a chemotherapeutic agent, toxin (e.g. a small molecule toxin or an enzymatically active toxin of bacterial, fungal, plant or animal origin, including fragments and/or variants thereof), or a radioactive isotope (i.e., a radioconjugate).

Chemotherapeutic agents useful in the generation of such immunoconjugates have been described above. Conjugates of an antibody and one or more small molecule toxins, such as a calicheamicin, a maytansine (U.S. Pat. No. 5,208,020), a trichothene, and CC1065 are also contemplated herein.

In one preferred embodiment of the invention, the antibody is conjugated to one or more maytansine molecules (e.g. about 1 to about 10 maytansine molecules per antibody molecule). Maytansine may, for example, be converted to May-SS-Me which may be reduced to May-SH3 and reacted with modified antibody (Chari et al. *Cancer Research* 52: 127-131 (1992)) to generate a maytansinoid-antibody immunoconjugate.

Another immunoconjugate of interest comprises an anti-ErbB2 antibody conjugated to one or more calicheamicin molecules. The calicheamicin family of antibiotics are capable of producing double-stranded DNA breaks at sub-picomolar concentrations. Structural analogues of calicheamicin which may be used include, but are not limited to, $\gamma_1^I$, $\alpha_2^I$, $\alpha_3^I$, N-acetyl-$\gamma_1^I$, PSAG and $\theta^I_1$, (Hinman et al. *Cancer Research* 53: 3336-3342 (1993) and Lode et al. *Cancer Research* 58: 2925-2928 (1998)). See, also, U.S. Pat. Nos. 5,714,586; 5,712,374; 5,264,586; and 5,773,001 expressly incorporated herein by reference.

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g. a ribonuclease or a DNA endonuclease such as a deoxyribonuclease; DNase).

A variety of radioactive isotopes are available for the production of radioconjugated anti-ErbB2 antibodies. Examples include $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu.

Conjugates of the antibody and cytotoxic agent may be made using a variety of bifunctional protein coupling agents such as N-succinimidyl-3-(2-pyridyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, dimethyl linker or disulfide-containing linker (Chari et al. *Cancer Research* 52: 127-131 (1992)) may be used.

Alternatively, a fusion protein comprising the anti-ErbB2 antibody and cytotoxic agent may be made, e.g. by recombinant techniques or peptide synthesis. Immunoconjugates of anti-ErbB2 antibody fused to a chemokine (e.g. RANTES) are described in WO98/33914).

In yet another embodiment, the antibody may be conjugated to a "receptor" (such streptavidin) for utilization in pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

(x) Antibody Dependent Enzyme Mediated Prodrug Therapy (ADEPT)

The antibodies of the present invention may also be used in ADEPT by conjugating the antibody to a prodrug-activating enzyme which converts a prodrug (e.g. a peptidyl chemotherapeutic agent, see WO81/01145) to an active drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the active drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328: 457-458 (1987)). Antibody-abzyme conjugates can be prepared as described herein for delivery of the abzyme to a cell population.

The enzymes of this invention can be covalently bound to the anti-ErbB2 antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature,* 312: 604-608 (1984).

(xi) Other Antibody Modifications

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylrnethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences,* 16th edition, Oslo, A., Ed., (1980).

The anti-ErbB2 antibodies disclosed herein may also be formulated as immunoliposomes. Liposomes containing the antibody are prepared by methods known in the art, such as described in Epstein et al., *Proc. Natl. Acad. Sci. USA,* 82:3688 (1985); Hwang et al., *Proc. Natl. Acad. Sci. USA,* 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. *J. Biol. Chem.* 257: 286-288 (1982) via a disulfide interchange reaction. A chemotherapeutic agent is optionally contained within the liposome. See Gabizon et al. *J. National Cancer Inst.* 81(19)1484 (1989).

Pharmaceutical Formulations

Therapeutic formulations of the ErbB antagonists of the present invention can be prepared as pharmaceutical formulations, using standard ingredients and techniques as described, for example, in *Remington's Pharmaceutical Sciences* 16th edition, Osol, A. Ed. (1980). Thus, anti-ErbB antibodies are prepared for storage by mixing an antagonist having the desired degree of purity with optional pharmaceutically acceptable carriers, excipients or stabilizers, in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN®, PLURONICS® or polyethylene glycol (PEG). Preferred lyophilized anti-ErbB2 antibody formulations are described in WO 97/04801, expressly incorporated herein by reference.

The formulation herein may also contain more than one active compound as necessary for the particular indication being treated, preferably those with complementary activities that do not adversely affect each other. For example, it may be desirable to further provide antibodies which bind to EGFR, ErbB2 (e.g. an antibody which binds a different epitope on ErbB2), ErbB3, ErbB4, or vascular endothelial factor (VEGF) in the one formulation. Alternatively, or additionally, the composition may further comprise a chemotherapeutic agent, cytotoxic agent, cytokine, growth inhibitory agent, anti-hormonal agent, EGFR-targeted drug, tyrosine kinase inhibitor, immunosuppressive agent, anti-angiogenic agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences*, supra.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

If the ErbB antagonist is a small organic molecule, it is preferably formulated in a form suitable for oral administration, although liquid preparations for injection or infusion administration are also suitable.

Pain Treatment with the ErbB Antagonist

The ErbB antagonists can be administered to human patients in accord with known methods. Thus, for example, anti-ErbB (e.g. anti-ErbB2) antibodies can be administered intravenously, e.g., as a bolus or by continuous infusion over a period of time, or by intramuscular, intraperitoneal, intracerobrospinal, subcutaneous, intra-articular, intrasynovial, intrathecal, oral, topical, or inhalation routes. Intravenous or subcutaneous administration of the antibodies is preferred.

Optimal dosage can be determined based upon dosing experiments in relevant animal models and fine tuned in human clinical trials. Typically, an effective dose will reduce the patient's pain score by at least 1, preferably by at least 2, more preferably by at least 3 grades, and preferably results in a pain score (on a 0 to 10 scale) of no more than 5, more preferably no more than 4, even more preferably no more than 3, most preferably no more than 2. The effective dose will also depend on the nature and severity of the initial pain.

The analgesic activity of a candidate ErbB antagonist is generally tested in a double-blind, randomized, placebo-controlled clinical trial. For general overview of the design of randomized controlled trials see, e.g. Jadad A R, Haynes R B. *Med Decis Making* 1998; 18:2-9.

Other therapeutic regimens may be combined with the administration of the ErbB antagonists, such as anti-ErbB2 antibodies. The combined administration includes coadministration, using separate formulations or a single pharmaceutical formulation, and consecutive administration in either order, wherein preferably there is a time period while both (or all) active agents simultaneously exert their biological activities.

In one preferred embodiment, the patient is treated with two different anti-ErbB2 antibodies. For example, the patient may be treated with a first anti-ErbB2 antibody which blocks ligand activation of an ErbB or an antibody having a biological characteristic of monoclonal antibody 2C4 as well as a second anti-ErbB2 antibody which is growth inhibitory (e.g. HERCEPTIN®) or an anti-ErbB2 antibody which induces apoptosis of an ErbB2-overexpressing cell (e.g. 7C2, 7F3 or humanized variants thereof). Preferably such combined therapy results in a synergistic therapeutic effect. One may, for instance, treat the patient with HERCEPTIN® and thereafter treat with rhuMAb 2C4, e.g. where the patient does not respond to HERCEPTIN® therapy. In another embodiment, the patient may first be treated with rhuMAb 2C4 and then receive HERCEPTIN® therapy. In yet a further embodiment, the patient may be treated with both rhuMAb 2C4 and HERCEPTIN® simultaneously.

It may also be desirable to combine administration of the anti-ErbB2 antibody or antibodies, with administration of an antibody directed against EGFR, ErbB3, ErbB4, or vascular endothelial growth factor (VEGF).

In one embodiment, the treatment of the present invention involves the combined administration of an anti-ErbB2 antibody (or antibodies) and one or more chemotherapeutic agents, cytotoxic agents, or growth inhibitory agents, including coadministration of cocktails of different chemotherapeutic agents. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

The antibody may be combined with an anti-hormonal compound; e.g., an anti-estrogen compound such as tamoxifen; an anti-progesterone such as onapristone (see, EP 616 812); or an anti-androgen such as flutamide, in dosages known for such molecules.

Sometimes, it may be beneficial to also coadminister a cardioprotectant (to prevent or reduce myocardial dysfunction associated with the therapy) or one or more cytokines to the patient. One may also coadminister an anti-angiogenic agent. In addition to the above therapeutic regimes, the patient may be subjected to surgery, radiation therapy, or phototherapy.

The anti-ErbB2 antibodies herein may also be combined with an EGFR-targeted drug, tyrosine kinase inhibitor and/or immunosuppressive agent, such as those discussed above in the definitions section resulting in a complementary, and potentially synergistic, therapeutic effect.

Suitable dosages for any of the above coadministered agents are those presently used and may be lowered due to the combined action (synergy) of the agent and anti-ErbB2 antibody.

As discussed above, for the prevention or treatment of pain, the appropriate dosage of antibody will depend on the type of and severity of pain to be treated, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. preferably about 0.1 or 0.5 to about 20 or about 30 mg/kg) of antibody is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. The preferred dosage of the antibody will be in the range from about 0.5 mg/kg to about 30 mg/kg. Thus, one or more doses of about 0.5 mg/kg, 2.0 mg/kg, 4.0 mg/kg, 6 mg/kg, 8 mg/kg, 10 mg/kg or 15 mg/kg (or any combination thereof) may be administered to the patient. Such doses may be administered intermittently, e.g. every week, every three weeks, monthly or less frequently, for instance every 3 or 4 months (e.g. such that the patient receives from about two to about twenty, e.g. about six doses of the anti-ErbB2 antibody). An initial higher loading dose, followed by one or more lower doses may be administered. An exemplary dosing regimen comprises administering an initial loading dose of about 4 mg/kg, followed by a weekly maintenance dose of about 2 mg/kg of the anti-ErbB2 antibody. However, other dosage regimens may be useful. The progress of this therapy is easily monitored by conventional techniques and assays.

While the antibody administered is preferably "naked" or "not conjugated with a cytotoxic agent," in certain embodiments, an immunoconjugate comprising the anti-ErbB (e.g. anti-ErbB2) antibody conjugated with a cytotoxic agent is administered to the patient. Preferably, the immunoconjugate and/or ErbB2 protein to which it is bound is/are internalized by the cell, resulting in increased therapeutic efficacy of the immunoconjugate. In a preferred embodiment, the cytotoxic agent targets or interferes with nucleic acid in a cell. Examples of such cytotoxic agents include maytansinoids, calicheamicins, ribonucleases and DNA endonucleases.

Aside from administration of the antibody protein to the patient, the present application contemplates administration of the antibody by gene therapy. Such administration of nucleic acid encoding the antibody is encompassed by the expression "administering a therapeutically effective amount of an antibody". See, for example, WO96/07321 published Mar. 14, 1996 and WO01/56604 published Aug. 9, 2001 concerning antibodies to HER2 administered by gene therapy.

There are two major approaches to getting the nucleic acid (optionally contained in a vector) into the patient's cells; in vivo and ex vivo. For in vivo delivery the nucleic acid is injected directly into the patient, usually at the site where the antibody is required. For ex vivo treatment, the patient's cells are removed, the nucleic acid is introduced into these isolated cells and the modified cells are administered to the patient either directly or, for example, encapsulated within porous membranes which are implanted into the patient (see, e.g. U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., *J. Biol. Chem.* 262:4429-4432 (1987); and Wagner et al., *Proc. Natl. Acad. Sci. USA* 87:3410-3414 (1990). For review of the currently known gene marking and gene therapy protocols see Anderson et al., *Science* 256:808-813 (1992). See also WO 93/25673 and the references cited therein.

Deposit of Materials

The following hybridoma cell lines have been deposited with the American Type Culture Collection (ATCC), 10801 University Boulevard, Manassas, Va. 20110-2209, USA (ATCC):

| Antibody Designation | ATCC No. | Deposit Date |
|---|---|---|
| 7C2 | ATCC HB-12215 | Oct. 17, 1996 |
| 7F3 | ATCC HB-12216 | Oct. 17, 1996 |
| 4D5 | ATCC CRL 10463 | May 24, 1990 |
| 2C4 | ATCC HB-12697 | Apr. 8, 1999 |

Further details of the invention are illustrated by the following non-limiting Examples. The disclosures of all citations in the specification are expressly incorporated herein by reference.

EXAMPLE 1

Production and Characterization of Monoclonal Antibody 2C4

The murine monoclonal antibodies 2C4, 7F3 and 4D5 which specifically bind the extracellular domain of ErbB2 were produced as described in Fendly et al., *Cancer Research* 50:1550-1558 (1990). Briefly, NIH 3T3/HER2-3$_{400}$ cells (expressing approximately 1×10$^5$ ErbB2 molecules/cell) produced as described in Hudziak et al *Proc. Natl. Acad. Sci. (USA)* 84:7158-7163 (1987) were harvested with phosphate buffered saline (PBS) containing 25 mM EDTA and used to immunize BALB/c mice. The mice were given injections i.p. of 10$^7$ cells in 0.5 ml PBS on weeks 0, 2, 5 and 7. The mice with antisera that immunoprecipitated $^{32}$P-labeled ErbB2 were given i.p. injections of a wheat germ agglutinin-Sepharose (WGA) purified ErbB2 membrane extract on weeks 9 and 13. This was followed by an i.v. injection of 0.1 ml of the ErbB2 preparation and the splenocytes were fused with mouse myeloma line X63-Ag8.653.

Hybridoma supernatants were screened for ErbB2-binding by ELISA and radioimmunoprecipitation.

The ErbB2 epitopes bound by monoclonal antibodies 4D5, 7F3 and 2C4 were determined by competitive binding analysis (Fendly et al. *Cancer Research* 50:1550-1558 (1990)). Cross-blocking studies were done on antibodies by direct fluorescence on intact cells using the PANDEX® Screen Machine to quantitate fluorescence. Each monoclonal antibody was conjugated with fluorescein isothiocyanate (FITC), using established procedures (Wofsy et al. *Selected Methods in Cellular Immunology*, p. 287, Mishel and Schiigi (eds.) San Francisco: W.J. Freeman Co. (1980)). Confluent monolayers of NIH 3T3/HER2-3$_{400}$ cells were trypsinized, washed once, and resuspended at 1.75×10$^6$ cell/ml in cold PBS containing 0.5% bovine serum albumin (BSA) and 0.1% NaN$_3$. A final concentration of 1% latex particles (IDC, Portland, Oreg.) was added to reduce clogging of the PANDEX® plate membranes. Cells in suspension, 20 µl, and 20 µl of purified monoclonal antibodies (100 µg/ml to 0.1 µg/ml) were added to the PANDEX® plate wells and incubated on ice for 30 minutes. A predetermined dilution of FITC-labeled monoclonal antibodies in 20 µl was added to each well, incubated for 30 minutes, washed, and the fluorescence was quantitated by the PANDEX®. Monoclonal antibodies were considered to share an epitope if each blocked binding of the other by 50% or greater in comparison to an irrelevant monoclonal antibody control. In this experiment, monoclonal antibodies 4D5, 7F3 and 2C4 were assigned epitopes I, G/F and F, respectively.

The growth inhibitory characteristics of monoclonal antibodies 2C4, 7F3 and 4D5 were evaluated using the breast tumor cell line, SK-BR-3 (see Hudziak et al. *Molec. Cell. Biol.* 9(3):1165-1172 (1989)). Briefly, SK-BR-3 cells were detached by using 0.25% (vol/vol) trypsin and suspended in complete medium at a density of 4×10$^5$ cells per ml. Aliquots of 100 µl (4×10$^4$ cells) were plated into 96-well microdilution plates, the cells were allowed to adhere, and 100 µl of media alone or media containing monoclonal antibody (final concentration 5 µg/ml) was then added. After 72 hours, plates were washed twice with PBS (pH 7.5), stained with crystal violet (0.5% in methanol), and analyzed for relative cell proliferation as described in Sugarman et al. *Science* 230:943-945 (1985). Monoclonal antibodies 2C4 and 7F3 inhibited SK-BR-3 relative cell proliferation by about 20% and about 38%, respectively, compared to about 56% inhibition achieved with monoclonal antibody 4D5.

Monoclonal antibodies 2C4, 4D5 and 7F3 were evaluated for their ability to inhibit HRG-stimulated tyrosine phosphorylation of proteins in the $M_r$ 180,000 range from whole-cell lysates of MCF7 cells (Lewis et al. *Cancer Research* 56:1457-1465 (1996)). MCF7 cells are reported to express all known ErbBs, but at relatively low levels. Since ErbB2, ErbB3, and ErbB4 have nearly identical molecular sizes, it is not possible to discern which protein is becoming tyrosine phosphorylated when whole-cell lysates are evaluated by Western blot analysis.

However, these cells are ideal for HRG tyrosine phosphorylation assays because under the assay conditions used, in the absence of exogenously added HRG, they exhibit low to undetectable levels of tyrosine phosphorylation proteins in the $M_r$ 180,000 range.

MCF7 cells were plated in 24-well plates and monoclonal antibodies to ErbB2 were added to each well and incubated for 30 minutes at room temperature; then rHRGβ1$_{177-244}$ was added to each well to a final concentration of 0.2 nM, and the incubation was continued for 8 minutes. Media was carefully aspirated from each well, and reactions were stopped by the addition of 100 μl of SDS sample buffer (5% SDS, 25 mM DTT, and 25 mM Tris-HCl, pH 6.8). Each sample (25 μl) was electrophoresed on a 4-12% gradient gel (Novex) and then electrophoretically transferred to polyvinylidene difluoride membrane. Antiphosphotyrosine (4G10, from UBI, used at 1 μg/ml) immunoblots were developed, and the intensity of the predominant reactive band at $M_r$~180,000 was quantified by reflectance densitometry, as described previously (Holmes et al. *Science* 256:1205-1210 (1992); Sliwkowski et al. *J. Biol. Chem.* 269:14661-14665 (1994)).

Figure 2A:
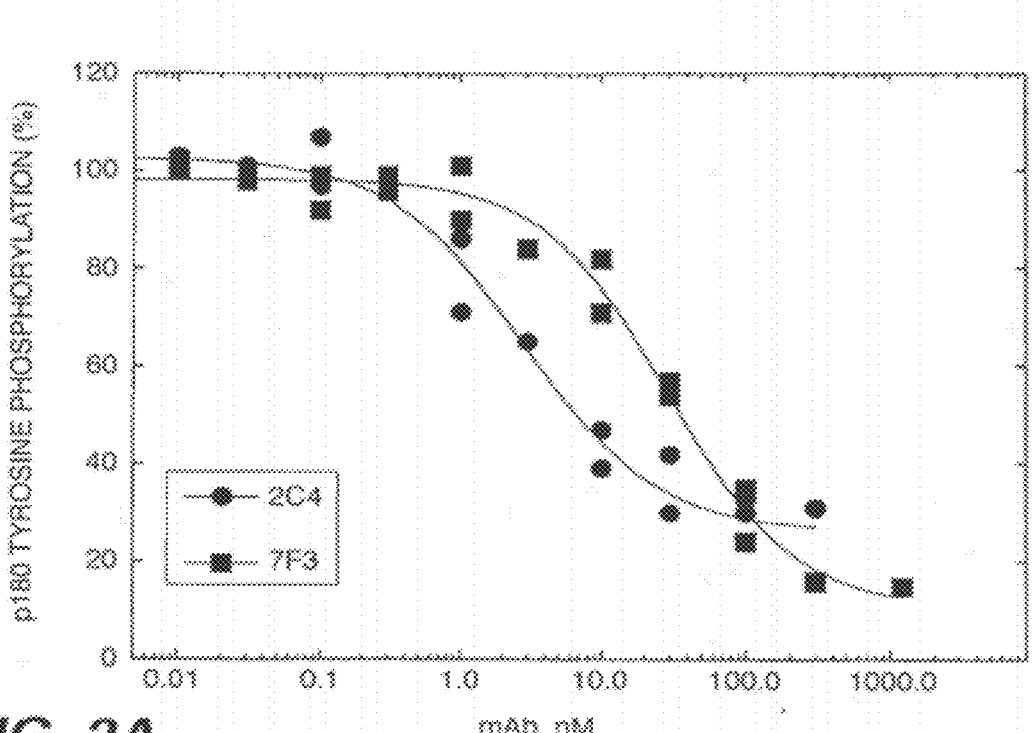
FIGS. 2A and 2B show the effect of anti-ErbB2 monoclonal antibodies 2C4 and 7F3 on rHRGβ1 activation of MCF7 cells.

Monoclonal antibodies 2C4, 7F3, and 4D5, significantly inhibited the generation of a HRG-induced tyrosine phosphorylation signal at $M_r$ 180,000. In the absence of HRG, none of these antibodies were able to stimulate tyrosine phosphorylation of proteins in the $M_r$ 180,000 range. Also, these antibodies do not cross-react with EGFR (Fendly et al. *Cancer Research* 50:1550-1558 (1990)), ErbB3, or ErbB4. Antibodies 2C4 and 7F3 significantly inhibited HRG stimulation of p180 tyrosine phosphorylation to <25% of control. Monoclonal antibody 4D5 was able to block HRG stimulation of tyrosine phosphorylation by ~50%. FIG. 2A shows dose-response curves for 2C4 or 7F3 inhibition of HRG stimulation of p180 tyrosine phosphorylation as determined by reflectance densitometry. Evaluation of these inhibition curves using a 4-parameter fit yielded an IC$_{50}$ of 2.8±0.7 nM and 29.0±4.1 nM for 2C4 and 7F3, respectively.

Figure 2B:
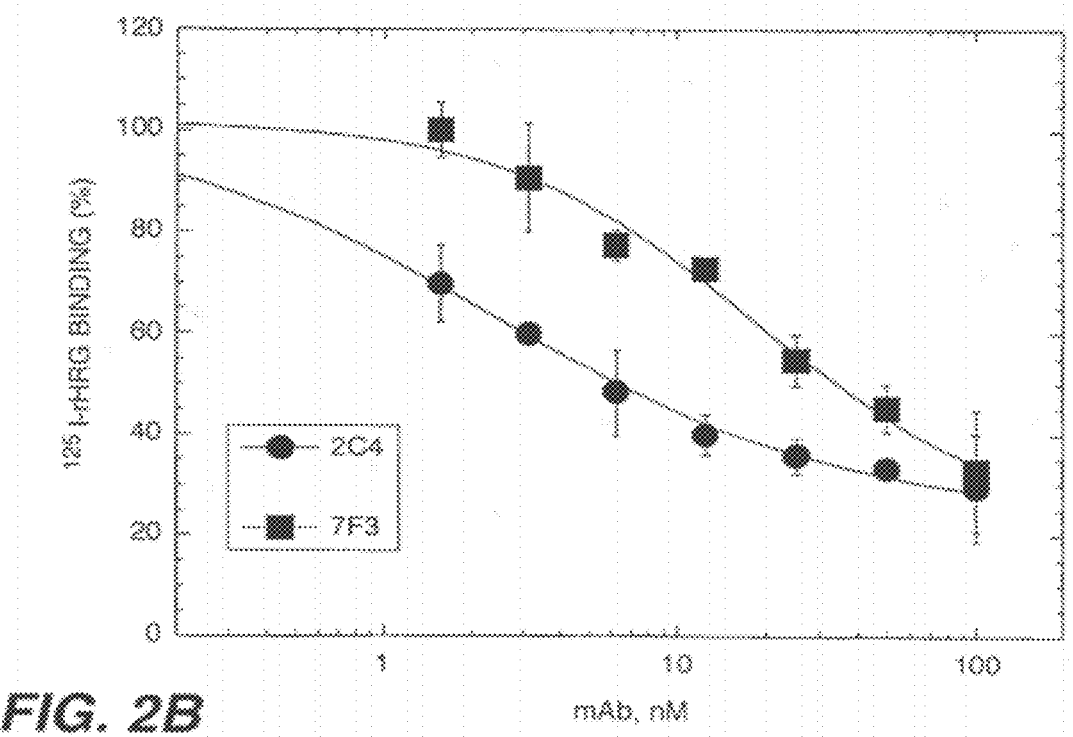

Inhibition of HRG binding to MCF7 breast tumor cell lines by anti-ErbB2 antibodies was performed with monolayer cultures on ice in a 24-well-plate format (Lewis et al. *Cancer Research* 56:1457-1465 (1996)). Anti-ErbB2 monoclonal antibodies were added to each well and incubated for 30 minutes $^{125}$I-labeled rHRGβ1$_{177-224}$ (25 pm) was added, and the incubation was continued for 4 to 16 hours. FIG. 2B provides dose-response curves for 2C4 or 7F3 inhibition of HRG binding to MCF7 cells. Varying concentrations of 2C4 or 7F3 were incubated with MCF7 cells in the presence of $^{125}$I-labeled rHRGβ1, and the inhibition curves are shown in FIG. 2B. Analysis of these data yielded an IC$_{50}$ of 2.4±0.3 nM and 19.0±7.3 nM for 2C4 and 7F3, respectively. A maximum inhibition of ~74% for 2C4 and 7F3 were in agreement with the tyrosine phosphorylation data.

Figure 3:
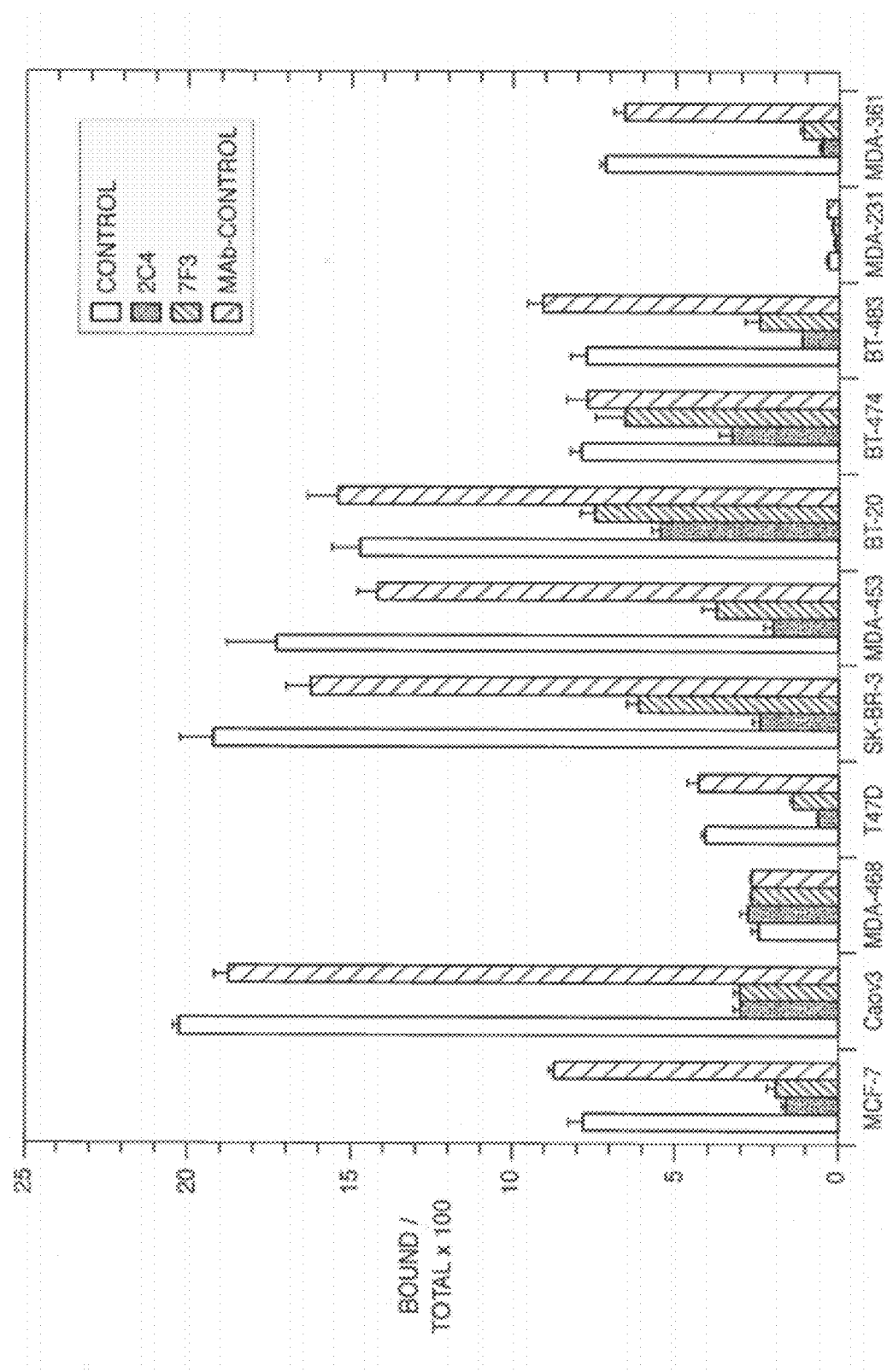
FIG. 3 depicts inhibition of specific $^{125}$I-labeled rHRGβ1$_{177-244}$ binding to a panel of human tumor cell lines by the anti-ErbB2 monoclonal antibodies 2C4 or 7F3. Monoclonal antibody-controls are isotype-matched murine monoclonal antibodies that do not block rHRG binding. Nonspecific $^{125}$I-labeled rHRGβ1$_{177-244}$ binding was determined from parallel incubations performed in the presence of 100 nM rHRGβ1. Values for nonspecific $^{125}$I-labeled rHRGβ1$_{177-244}$ binding were less than 1% of the total for all the cell lines tested.

To determine whether the effect of the anti-ErbB2 antibodies observed on MCF7 cells was a general phenomenon, human tumor cell lines were incubated with 2C4 or 7F3 and the degree of specific $^{125}$I-labeled rHRGβ1 binding was determined (Lewis et al. *Cancer Research* 56:1457 1465 (1996)). The results from this study are shown in FIG. 3. Binding of $^{121}$I-labeled rHRGβ1 could be significantly inhibited by either 2C4 or 7F3 in all cell lines, with the exception of the breast cancer cell line MDA-MB-468, which has been reported to express little or no ErbB2. The remaining cell lines are reported to express ErbB2, with the level of ErbB2 expression varying widely among these cell lines. In fact, the range of ErbB2 expression in the cell lines tested varies by more than 2 orders of magnitude. For example, BT-20, MCF7, and Caov3 express ~10$^4$ ErbB2 receptors/cell, whereas BT-474 and SK-BR-3 express ~10$^6$ ErbB2 receptors/cell. Given the wide range of ErbB2 expression in these cells and the data above, it was concluded that the interaction between ErbB2 and ErbB3 or ErbB4, was itself a high-affinity interaction that takes place on the surface of the plasma membrane.

Figure 4A:
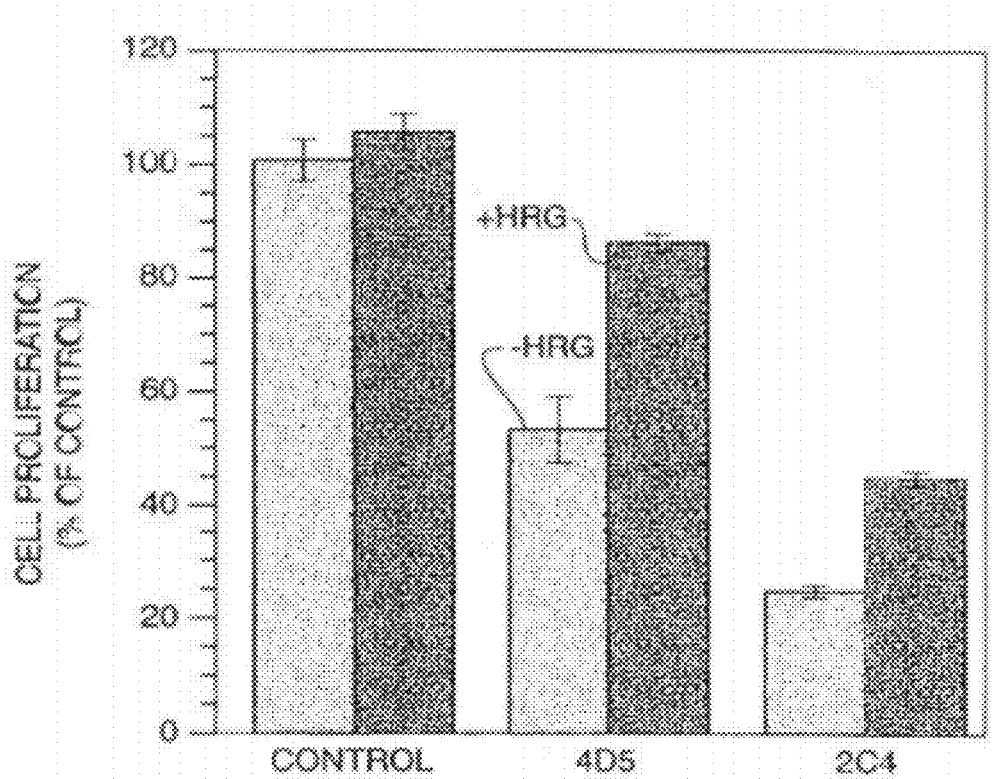
FIGS. 4A and 4B show the effect of monoclonal antibodies 2C4 and 4D5 on proliferation of MDA-MB-175 (FIG. 4A) and SK-BR-3 (FIG. 4B) cells. MDA-MB-175 and SK-BR-3 cells were seeded in 96 well plates and allowed to adhere for 2 hours. Experiment was carried out in medium containing 1% serum. Anti-ErbB2 antibodies or medium alone were added and the cells were incubated for 2 hours at 37° C. Subsequently rHRGβ1 (1 nM) or medium alone were added and the cells were incubated for 4 days. Monolayers were washed and stained/fixed with 0.5% crystal violet. To determine cell proliferation the absorbance was measured at 540 nm.
Figure 4B:
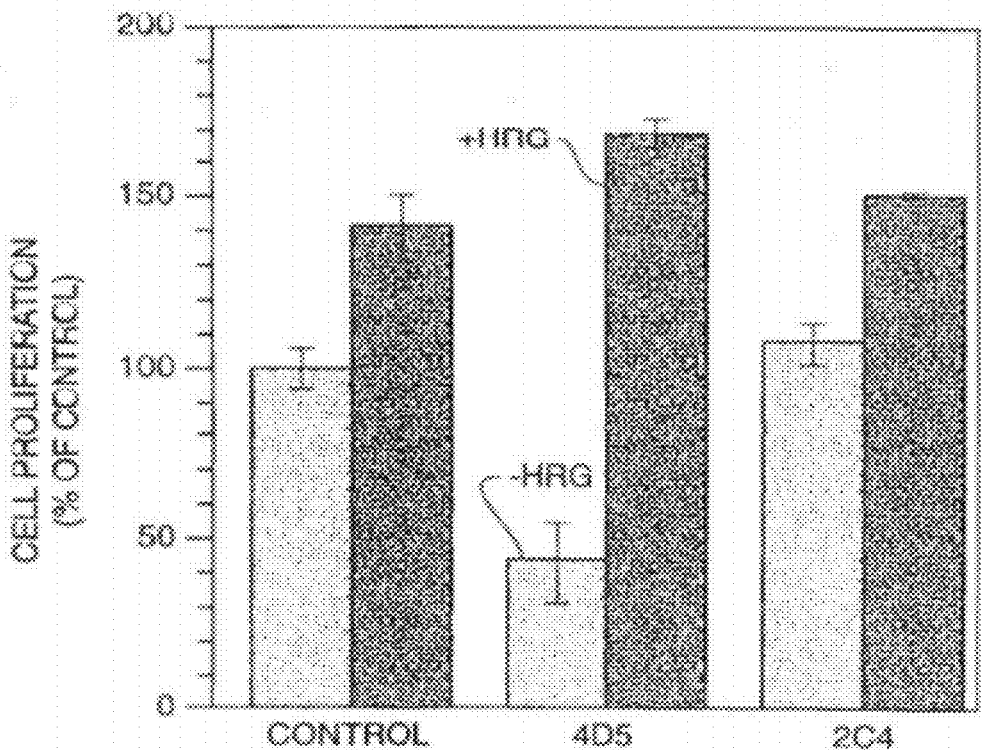

The growth inhibitory effects of monoclonal antibodies 2C4 and 4D5 on MDA-MB-175 and SK-BR-3 cells in the presence or absence of exogenous rHRGβ1 was assessed (Schaefer et al. *Oncogene* 15:1385-1394 (1997)). ErbB2 levels in MDA-MB-175 cells are 4-6 times higher than the level found in normal breast epithelial cells and the ErbB2-ErbB4 receptor is constitutively tyrosine phosphorylated in MDA-MB-175 cells. MDA-MB-175 cells were treated with an anti-ErbB2 monoclonal antibodies 2C4 and 4D5 (10 μg/mL) for 4 days. In a crystal violet staining assay, incubation with 2C4 showed a strong growth inhibitory effect on this cell line (FIG. 4A). Exogenous HRG did not significantly reverse this inhibition. On the other hand 2C4 revealed no inhibitory effect on the ErbB2 overexpressing cell line SK-BR-3 (FIG. 4B). Monoclonal antibody 2C4 was able to inhibit cell proliferation of MDA-MB-175 cells to a greater extent than monoclonal antibody 4D5, both in the presence and absence of exogenous HRG. Inhibition of cell proliferation by 4D5 is dependent on the ErbB2 expression level (Lewis et al. *Cancer Immunol. Immunother.* 37:255-263 (1993)). A maximum inhibition of 66% in SK-BR-3 cells could be detected (FIG. 4B). However this effect could be overcome by exogenous HRG.

EXAMPLE 2

HRG Dependent Association of ErbB2 with ErbB3 is Blocked by Monoclonal Antibody 2C4

The ability of ErbB3 to associate with ErbB2 was tested in a co-immunoprecipitation experiment. 1.0×10$^6$ MCF7 or SK-BR-3 cells were seeded in six well tissue culture plates in 50:50 DMEM/Ham's F12 medium containing 10% fetal bovine serum (FBS) and 10 mM HEPES, pH 7.2 (growth medium), and allowed to attach overnight. The cells were starved for two hours in growth medium without serum prior to beginning the experiment.

The cells were washed briefly with phosphate buffered saline (PBS) and then incubated with either 100 nM of the indicated antibody diluted in 0.2% w/v bovine serum albumin (BSA), RPMI medium, with 10 mM HEPES, pH 7.2 (binding buffer), or with binding buffer alone (control). After one hour at room temperature, HRG was added to a final concentration of 5 nM to half the wells (+). A similar volume of binding buffer was added to the other wells (−). The incubation was continued for approximately 10 minutes.

Supernatants were removed by aspiration and the cells were lysed in RPMI, 10 mM HEPES, pH 7.2, 1.0% v/v TRITON X-100®, 1.0% w/v CHAPS (lysis buffer), containing 0.2 mM PMSF, 10 µg/ml leupeptin, and 10 TU/ml aprotinin. The lysates were cleared of insoluble material by centrifugation.

ErbB2 was immunoprecipitated using a monoclonal antibody covalently coupled to an affinity gel (Affi-Prep 10, Bio-Rad). This antibody (Ab-3, Oncogene Sciences) recognizes a cytoplasmic domain epitope. Immunoprecipitation was performed by adding 10 µl of gel slurry containing approximately 8.5 µg of immobilized antibody to each lysate, and the samples were allowed to mix at room temperature for two hours. The gels were then collected by centrifugation. The gels were washed batchwise three times with lysis buffer to remove unbound material. SDS sample buffer was then added and the samples were heated briefly in a boiling water bath.

Supernatants were run on 4-12% polyacrylamide gels and electroblotted onto nitrocellulose membranes. The presence of ErbB3 was assessed by probing the blots with a polyclonal antibody against a cytoplasmic domain epitope thereof (c-17, Santa Cruz Biotech). The blots were visualized using a chemiluminescent substrate (ECL, Amersham).

Figure 5A:
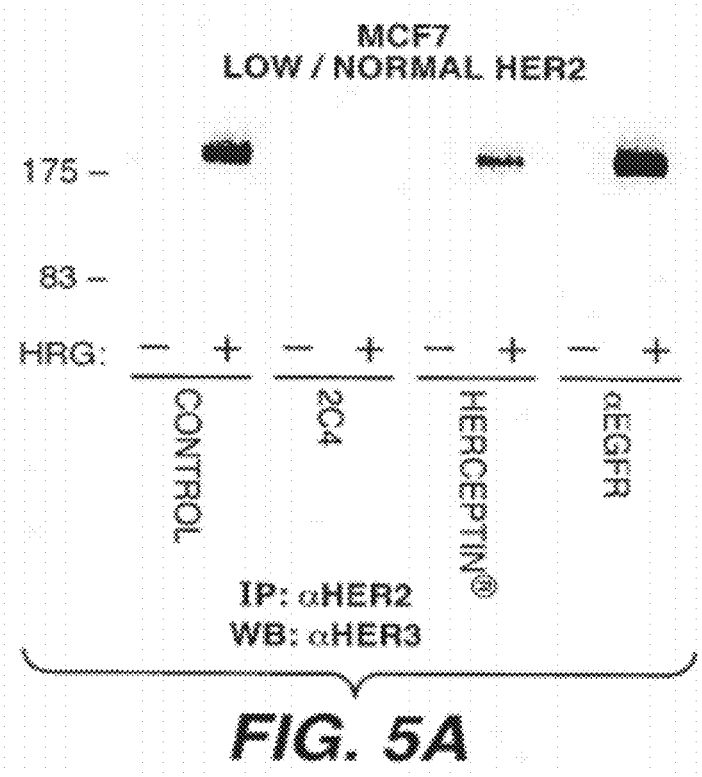
FIGS. 5A and 5B show the effect of monoclonal antibody 2C4, HERCEPTIN® antibody or an anti-EGFR antibody on heregulin (HRG) dependent association of ErbB2 with ErbB3 in MCF7 cells expressing low/normal levels of ErbB2 (FIG. 5A) and SK-BR-3 cells expressing high levels of ErbB2 (FIG. 5B); see Example 2 below.
Figure 5B:
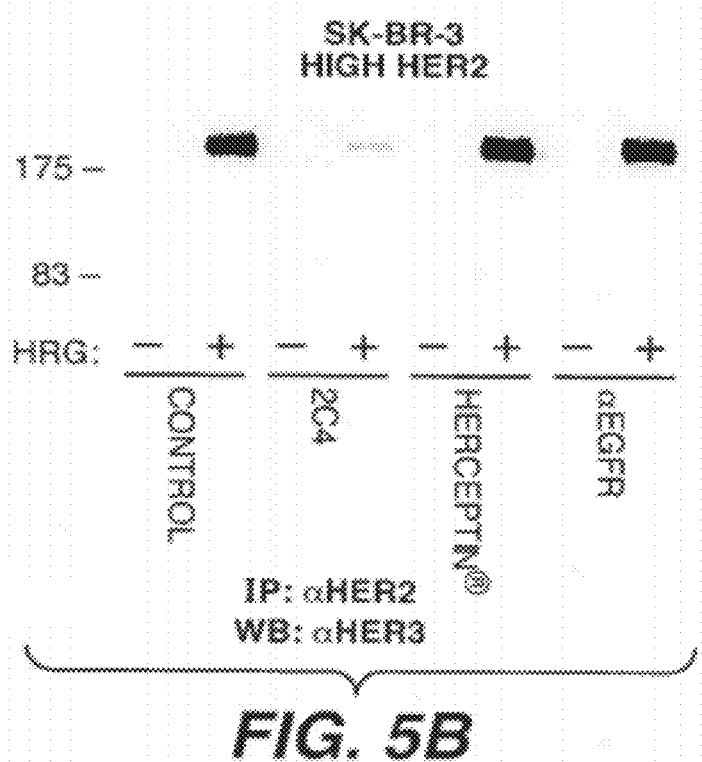

As shown in the control lanes of FIGS. 5A and 5B, for MCF7 and SK-BR-3 cells, respectively, ErbB3 was present in an ErbB2 immunoprecipitate only when the cells were stimulated with HRG. If the cells were first incubated with monoclonal antibody 2C4, the ErbB3 signal was abolished in MCF7 cells (FIG. 5A, lane 2C4+) or substantially reduced in SK-BR-3 cells (FIG. 5B, lane 2C4+). As shown in FIGS. 5A-B, monoclonal antibody 2C4 blocks heregulin dependent association of ErbB3 with ErbB2 in both MCF7 and SK-BR-3 cells substantially more effectively than HERCEPTIN®. Preincubation with HERCEPTIN® decreased the ErbB3 signal in MCF7 lysates but had little or no effect on the amount of ErbB3 co-precipitated from SK-BR-3 lysates. Preincubation with an antibody against the EGF receptor (Ab-1, Oncogene Sciences) had no effect on the ability of ErbB3 to co-immunoprecipitate with ErbB2 in either cell line.

EXAMPLE 3

Humanized 2C4 Antibodies

The variable domains of murine monoclonal antibody 2C4 were first cloned into a vector which allows production of a mouse/human chimeric Fab fragment. Total RNA was isolated from the hybridoma cells using a Stratagene RNA extraction kit following manufacturer's protocols. The variable domains were amplified by RT-PCR, gel purified, and inserted into a derivative of a pUC119-based plasmid containing a human kappa constant domain and human $C_H1$ domain as previously described (Carter et al. *PNAS (USA)* 89:4285 (1992); and U.S. Pat. No. 5,821,337). The resultant plasmid was transformed into *E. coli* strain 16C9 for expression of the Fab fragment. Growth of cultures, induction of protein expression, and purification of Fab fragment were as previously described (Werther et al. *J. Immunol.* 157:4986-4995 (1996); Presta et al. *Cancer Research* 57: 4593-4599 (1997)).

Figure 6A:
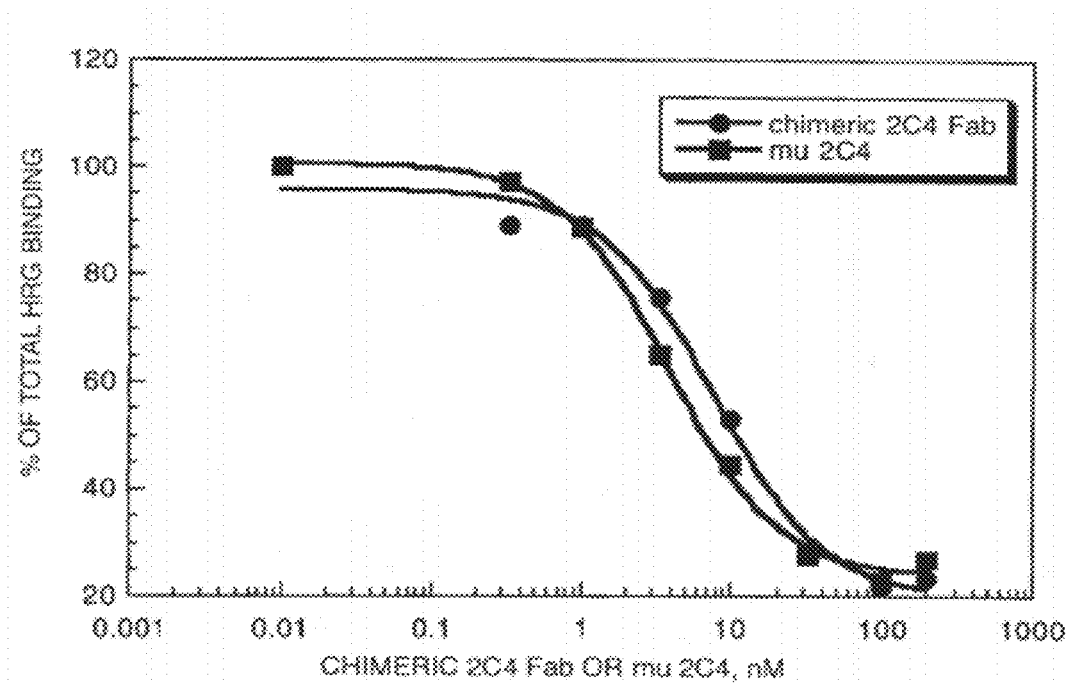
FIGS. 6A and 6B compare the activities of intact murine monoclonal antibody 2C4 (mu 2C4) and a chimeric 2C4 Fab fragment.
Figure 6B:
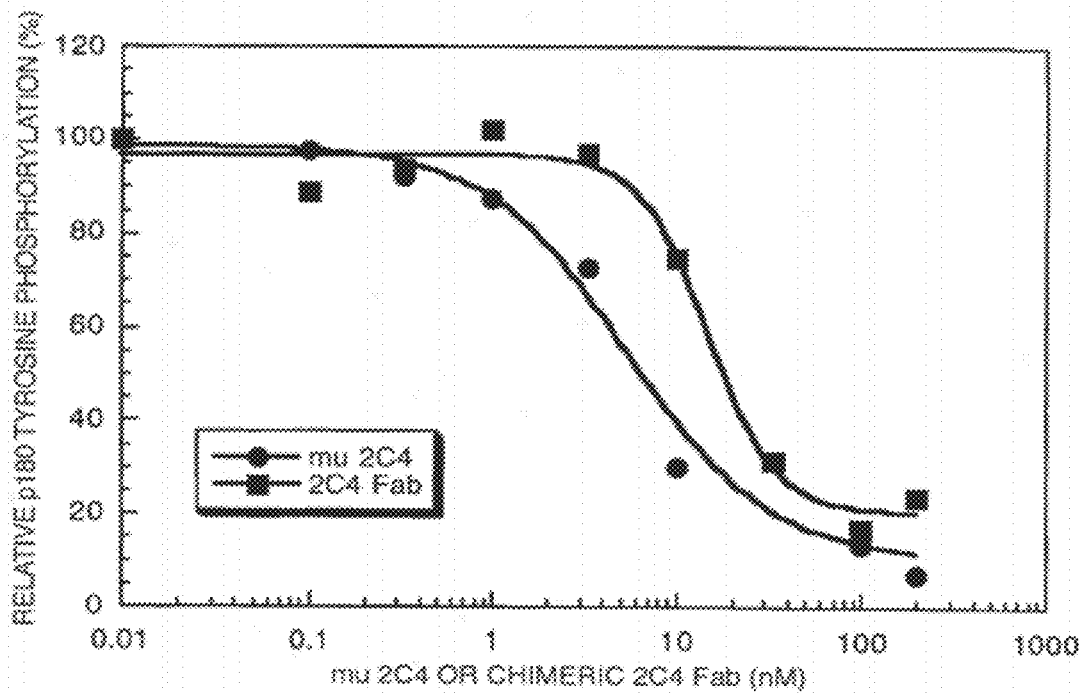

Purified chimeric 2C4 Fab fragment was compared to the murine parent antibody 2C4 with respect to its ability to inhibit $^{125}$I-HRG binding to MCF7 cells and inhibit rHRG activation of p180 tyrosine phosphorylation in MCF7 cells. As shown in FIG. 6A, the chimeric 2C4 Fab fragment is very effective in disrupting the formation of the high affinity ErbB2-ErbB3 binding site on the human breast cancer cell line, MCF7. The relative $IC_{50}$ value calculated for intact murine 2C4 is 4.0±0.4 nM, whereas the value for the Fab fragment is 7.7±1.1 nM. As illustrated in FIG. 6B, the monovalent chimeric 2C4 Fab fragment is very effective in disrupting HRG-dependent ErbB2-ErbB3 activation. The $IC_{50}$ value calculated for intact murine monoclonal antibody 2C4 is 6.0±2 nM, whereas the value for the Fab fragment is 15.0±2 nM.

Figure 8A:
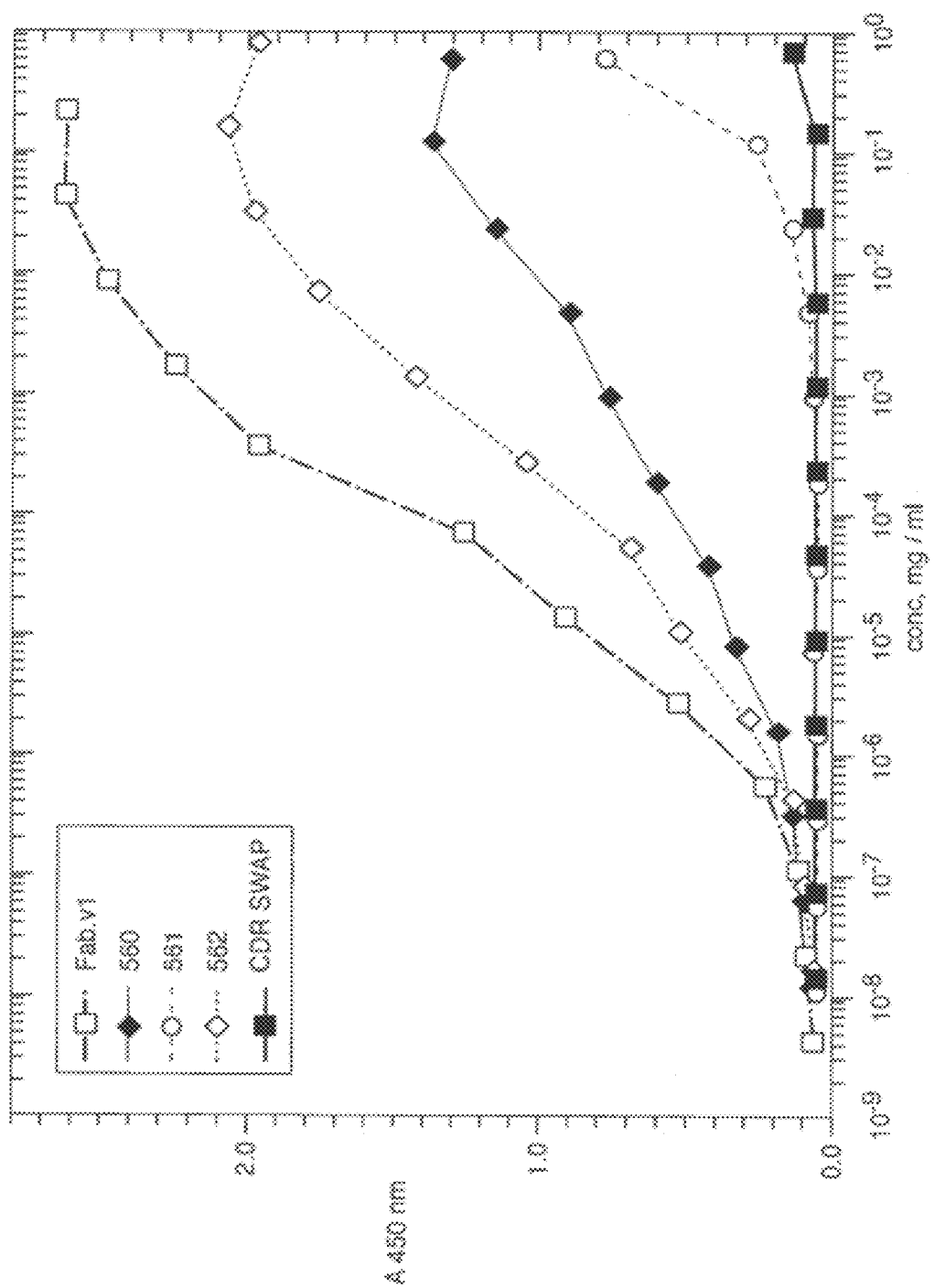
FIGS. 8A to C show binding of chimeric Fab 2C4 (Fab.v1) and several humanized 2C4 variants to ErbB2 extracellular domain (ECD) as determined by ELISA in Example 3.

DNA sequencing of the chimeric clone allowed identification of the CDR residues (Kabat et al., *Sequences of Proteins of Immunological Interest*, 5$^{th}$ Ed. Public Health Service, National Institutes of Health, Bethesda, Md. (1991)) (FIGS. 7A and B). Using oligonucleotide site-directed mutagenesis, all six of these CDR regions were introduced into a complete human framework ($V_L$ kappa subgroup I and $V_H$ subgroup III) contained on plasmid VX4 as previously described (Presta et al., *Cancer Research* 57: 4593-4599 (1997)). Protein from the resultant "CDR-swap" was expressed and purified as above. Binding studies were performed to compare the two versions. Briefly, a NUNC MAXISORP® plate was coated with 1 microgram per ml of ErbB2 extracellular domain (ECD; produced as described in WO 90/14357) in 50 mM carbonate buffer, pH 9.6, overnight at 4° C., and then blocked with ELISA diluent (0.5% BSA, 0.05% polysorbate 20, PBS) at room temperature for 1 hour. Serial dilutions of samples in ELISA diluent were incubated on the plates for 2 hours. After washing, bound Fab fragment was detected with biotinylated murine anti-human kappa antibody (ICN 634771) followed by streptavidin-conjugated horseradish peroxidase (Sigma) and using 3,3',5,5'-tetramethyl benzidine (Kirkegaard & Perry Laboratories, Gaithersburg, Md.) as substrate. Absorbance was read at 450 nm. As shown in FIG. 8A, all binding was lost on construction of the CDR-swap human Fab fragment.

Figure 9:
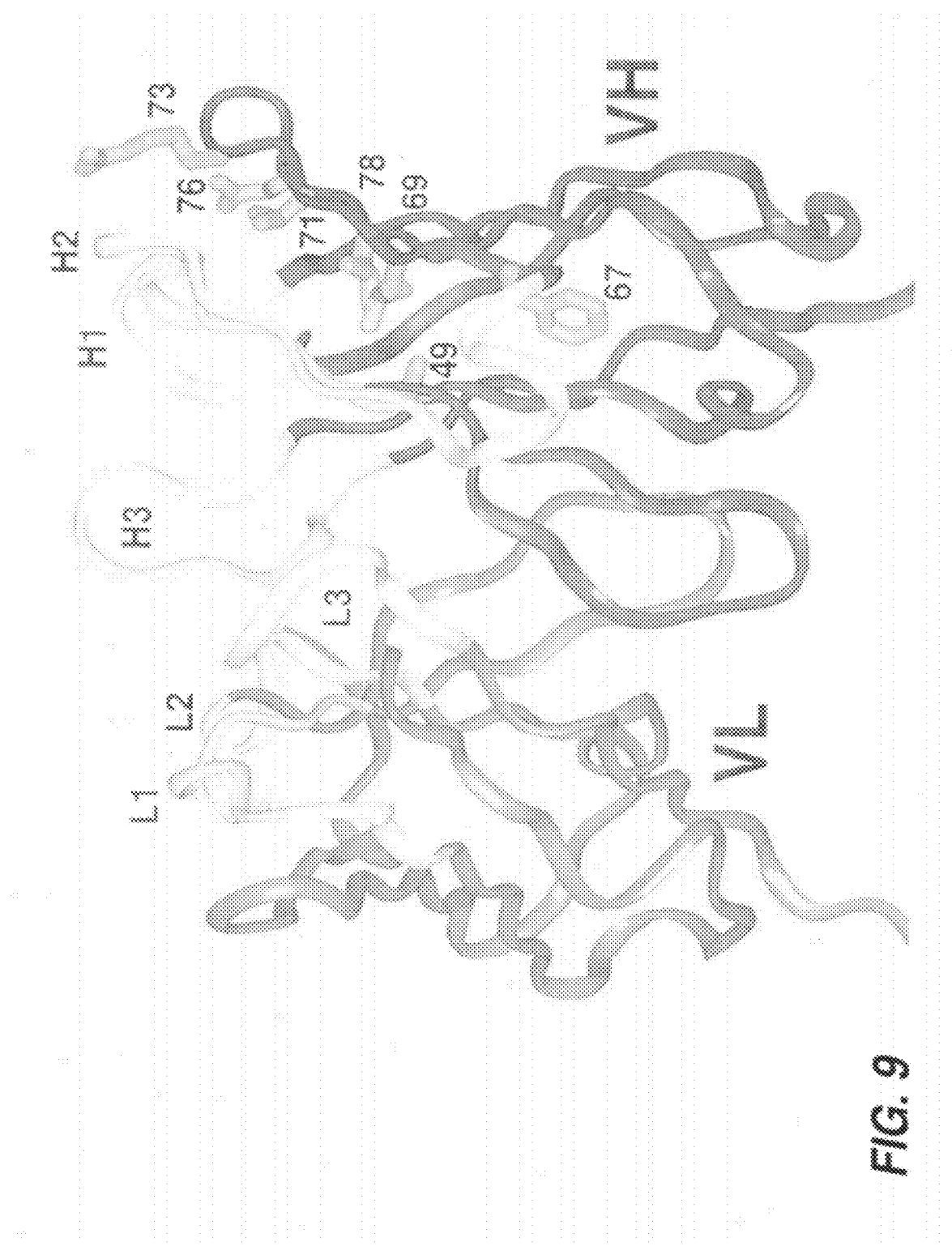
FIG. 9 is a ribbon diagram of the $V_L$ and $V_H$ domains of monoclonal antibody 2C4 with white CDR backbone labeled (L1, L2, L3, H1, H2, H3). $V_H$ side chains evaluated by mutagenesis during humanization (see Example 3, Table 2) are also shown.

To restore binding of the humanized Fab, mutants were constructed using DNA from the CDR-swap as template. Using a computer generated model (FIG. 9), these mutations were designed to change human framework region residues to their murine counterparts at positions where the change might affect CDR conformations or the antibody-antigen interface. Mutants are shown in Table 2.

TABLE 2

Designation of Humanized 2C4 FR Mutations

| Mutant no. | Framework region (FR) substitutions |
|---|---|
| 560 | ArgH71Val |
| 561 | AspH73Arg |
| 562 | ArgH71Val, AspH73Arg |
| 568 | ArgH71Val, AspH73Arg, AlaH49Gly |
| 569 | ArgH71Val, AspH73Arg, PheH67Ala |
| 570 | ArgH71Val, AspH73Arg, AsnH76Arg |
| 571 | ArgH71Val, AspH73Arg, LeuH78Val |
| 574 | ArgH71Val, AspH73Arg, IleH69Leu |
| 56869 | ArgH71Val, AspH73Arg, AlaH49Gly, PheH67Ala |

Figure 8B:
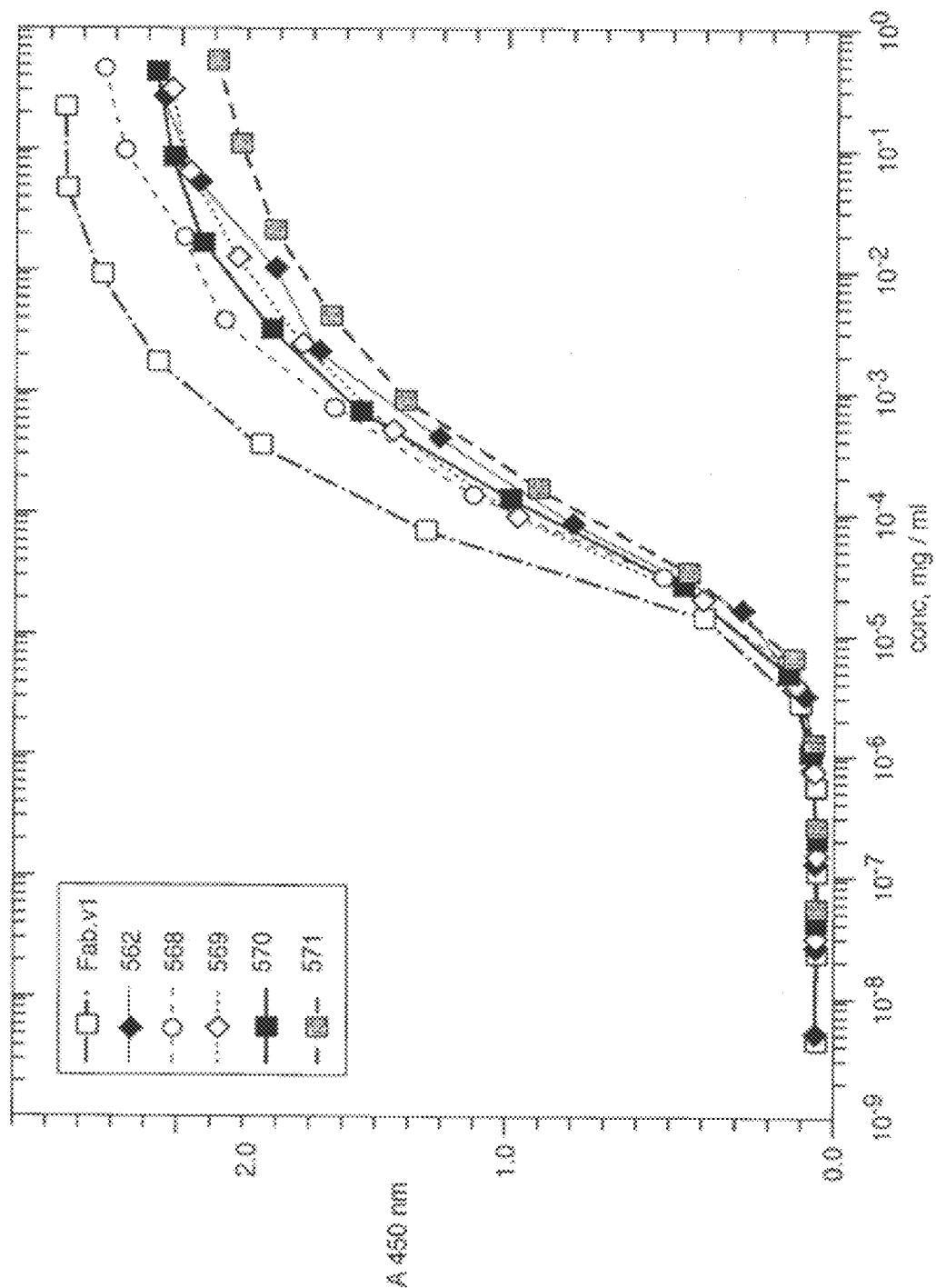
Figure 8C:
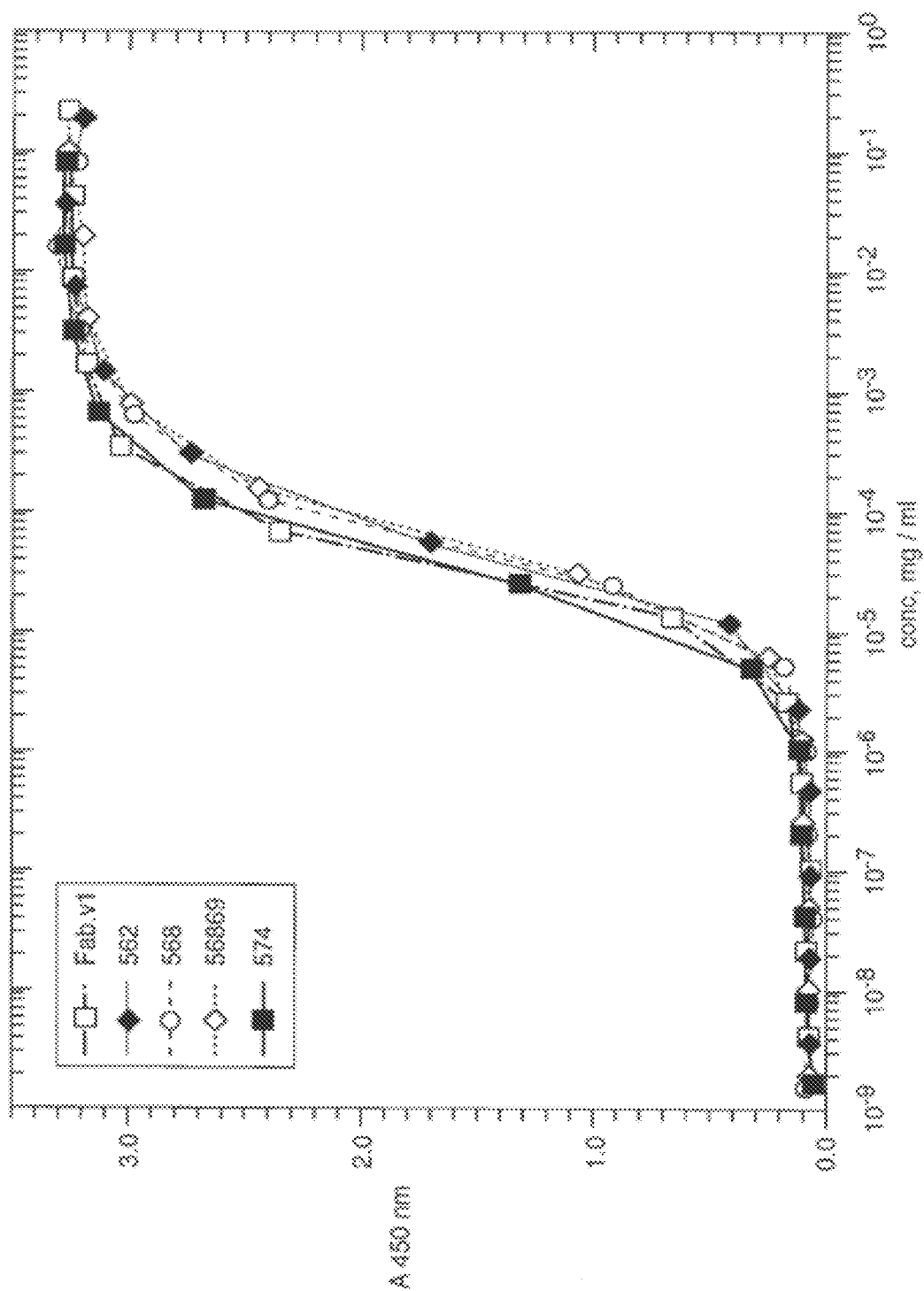

Binding curves for the various mutants are shown in FIGS. 8A-C. Humanized Fab version 574, with the changes ArgH71Val, AspH73Arg and IleH69Leu, appears to have binding restored to that of the original chimeric 2C4 Fab fragment. Additional FR and/or CDR residues, such as L2, L54, L55, L56, H35 and/or H48, may be modified (e.g. substituted as follows—IleL2Thr; ArgL54Leu; TyrL55Glu; ThrL56Ser; AspH35Ser; and ValH48Ile) in order to further refine or enhance binding of the humanized antibody. Alternatively, or additionally, the humanized antibody may be affinity matured (see above) in order to further improve or refine its affinity and/or other biological activities.

Humanized 2C4 version 574 was affinity matured using a phage-display method. Briefly, humanized 2C4.574 Fab was cloned into a phage display vector as a geneIII fusion. When phage particles are induced by infection with M13KO7 helper phage, this fusion allows the Fab to be displayed on the N-terminus of the phage tail-fiber protein, geneIII (Baca et J Biol. Chem. 272:10678 (1997)).

Individual libraries were constructed for each of the 6 CDRs identified above. In these libraries, the amino acids in the CDRs which were identified using a computer generated model (FIG. 9) as being potentially significant in binding to ErbB2 were randomized using oligos containing "NNS" as their codons. The libraries were then panned against ErbB2 ECD coated on NUNC MAXISORP™ plates with 3% dry milk in PBS with 0.2% TWEEN 20® (MPBST) used in place of all blocking solutions. In order to select for phage with affinities higher than that of 2C4.574, in panning rounds 3, 4, and 5, soluble ErbB2 ECD or soluble Fab 2C4.574 was added during the wash steps as competitor. Wash times were extended to 1 hour at room temperature.

After 5 rounds of panning, individual clones were again analyzed by phage-ELISA. Individual clones were grown in Costar 96-well U-bottomed tissue culture plates, and phage were induced by addition of helper phage. After overnight growth, E. coli cells were pelleted, and the phage-containing supernates were transferred to 96-well plates where the phage were blocked with MPBST for 1 hr at room temperature. NUNC MAXISORP™ plates coated with ErbB2 ECD were also blocked with MPBST as above. Blocked phage were incubated on the plates for 2 hours. After washing, bound phage were detected using horseradish-peroxidase-conjugated anti-M13 monoclonal antibody (Amersham Pharmacia Biotech, Inc. 27-9421-01) diluted 1:5000 in MPBST, followed by 3,3',5,5',-tetramethyl benzidine as substrate. Absorbance was read at 450 nm.

The 48 clones from each library which gave the highest signals were DNA sequenced. Those clones whose sequences occurred the most frequently were subcloned into the vector described above which allows expression of soluble Fabs. These Fabs were induced, proteins purified and the purified Fabs were analyzed for binding by ELISA as described above and the binding was compared to that of the starting humanized 2C4.574 version.

After interesting mutations in individual CDRs were identified, additional mutants which were various combinations of these were constructed and tested as above. Mutants which gave improved binding relative to 574 are described in Table 3.

TABLE 3

Designation of mutants derived from affinity maturation of 2C4.574

| Mutant Name | Change from 574 | Mutant/574* |
| --- | --- | --- |
| H3.A1 | serH99trp, metH34leu | 0.380 |
| L2.F5 | serL50trp, tyrL53gly, metH34leu | 0.087 |
| H1.3.B3 | thrH28gln, thrH30ser, metH34leu | 0.572 |
| L3.G6 | tyrL92pro, ileL93lys, metH34leu | 0.569 |
| L3.G11 | tyrL92ser, ileL93arg, tyrL94gly, metH34leu | 0.561 |
| L3.29 | tyrL92phe, tyrL96asn, metH34leu | 0.552 |
| L3.36 | tyrL92phe, tyrL94leu, tyrL96pro, metH34leu | 0.215 |
| 654 | serL50trp, metH34leu | 0.176 |
| 655 | metH34ser | 0.542 |
| 659 | serL50trp, metH34ser | 0.076 |
| L2.F5.H3.A1 | serL50trp, tyrL53gly, metH34leu, serH99trp | 0.175 |
| L3G6.H3.A1 | tyrL92pro, ileL93lys, metH34leu, serH99trp | 0.218 |
| H1.3.B3.H3.A1 | thrH28gln, thrH30ser, metH34leu, serH99trp | 0.306 |

TABLE 3-continued

Designation of mutants derived from affinity maturation of 2C4.574

| Mutant Name | Change from 574 | Mutant/574* |
| --- | --- | --- |
| L3.G11.H3.A1 | tyrL92ser, ileL93arg, tyrL94gly, metH34leu, serH99trp | 0.248 |
| 654.H3.A1 | serL50trp, metH34leu, serH99trp | 0.133 |
| 654.L3.G6 | serL50trp, metH34leu, tyrL92pro, ileL93lys | 0.213 |
| 654.L3.29 | serL50trp, metH34leu, tyrL92phe, tyrL96asn | 0.236 |
| 654.L3.36 | serL50trp, metH35leu, tyrL92phe, tyrL94leu, tyrL96pro | 0.141 |

*Ratio of the amount of mutant needed to give the mid-OD of the standard curve to the amount of 574 needed to give the mid-OD of the standard curve in an Erb2-ECD ELISA. A number less than 1.0 indicates that the mutant binds Erb2 better than 574 binds.

The following mutants have also been constructed, and are currently under evaluation:

| | |
| --- | --- |
| 659.L3.G6 | serL50trp, metH34ser, tyrL92pro, ileL93lys |
| 659.L3.G11 | serL50trp, metH34ser, tyrL92ser, ileL93arg, tyrL94gly |
| 659.L3.29 | serL50trp, metH34ser, tyrL92phe, tyrL96asn |
| 659.L3.36 | serL50trp, metH34ser, tyrL92phe, tyrL94leu, tyrL96pro |
| L2F5.L3G6 | serL50trp, tyrL53gly, metH34leu, tyrL92pro, ileL93lys |
| L2F5.L3G11 | serL50trp, tyrL53gly, metH34leu, tyrL92ser, ileL93arg, tyrL94gly |
| L2F5.L29 | serL50trp, tyrL53gly, metH34leu, tyrL92phe, tyrL96asn |
| L2F5.L36 | serL50trp, tyrL53gly, metH34leu, tyrL92phe, tyrL94leu, tyrL96pro |
| L2F5.L3G6.655 | serL50trp, tyrL53gly, metH35ser, tyrL92pro, ileL93lys |
| L2F5.L3G11.655 | serL50trp, tyrL53gly, metH34ser, tyrL92ser, ileL93arg, tyrL94gly |
| L2F5.L29.655 | serL50trp, tyrL53gly, metH34ser, tyrL92phe, tyrL96asn |
| L2F5.L36.655 | serL50trp, tyrL53gly, metH34ser, tyrL92phe, tyrL94leu, tyrL96pro. |

The following mutants, suggested by a homology scan, are currently being constructed:

| | |
| --- | --- |
| 678 | thrH30ala |
| 679 | thrH30ser |
| 680 | lysH64arg |
| 681 | leuH96val |
| 682 | thrL97ala |
| 683 | thrL97ser |
| 684 | tyrL96phe |
| 685 | tyrL96ala |
| 686 | tyrL91phe |
| 687 | thrL56ala |
| 688 | glnL28ala |
| 689 | glnL28glu |

The preferred amino acid at H34 would be methionine. A change to leucine might be made if there were found to be oxidation at this position.

AsnH52 and asnH53 were found to be strongly preferred for binding. Changing these residues to alanine or aspartic acid dramatically decreased binding.

An intact antibody comprising the variable light and heavy domains of humanized version 574 with a human IgG1 heavy chain constant region has been prepared (see U.S. Pat. No. 5,821,337). The intact antibody is produced by Chinese Hamster Ovary (CHO) cells. That molecule is designated rhuMAb 2C4 herein.

EXAMPLE 4

Monoclonal Antibody 2C4 Blocks EGF, TGF-α or HRG Mediated Activation of MAPK

Many growth factor receptors signal through the mitogen-activated protein kinase (MAPK) pathway. These dual specificity kinases are one of the key endpoints in signal transduction pathways that ultimately triggers cancer cells to divide. The ability of monoclonal antibody 2C4 or HERCEPTIN® to inhibit EGF, TGF-α or HRG activation of MAPK was assessed in the following way.

MCF7 cells ($10^5$ cells/well) were plated in serum containing media in 12-well cell culture plates. The next day, the cell media was removed and fresh media containing 0.1% serum was added to each well. This procedure was then repeated the following day and prior to assay the media was replaced with serum-free binding buffer (Jones et al. *J. Biol. Chem.* 273: 11667-74 (1998); and Schaefer et al. *J. Biol. Chem.* 274:859-66 (1999)). Cells were allowed to equilibrate to room temperature and then incubated for 30 minutes with 0.5 mL of 200 nM HERCEPTIN® or monoclonal antibody 2C4. Cells were then treated with 1 nM EGF, 1 nM TGF-α or 0.2 nM HRG for 15 minutes. The reaction was stopped by aspirating the cell medium and then adding 0.2 mL SDS-PAGE sample buffer containing 1% DTT. MAPK activation was assessed by Western blotting using an anti-active MAPK antibody (Promega) as described previously (Jones et al. *J. Biol. Chem.* 273:11667-74 (1998)).

Figure 10:
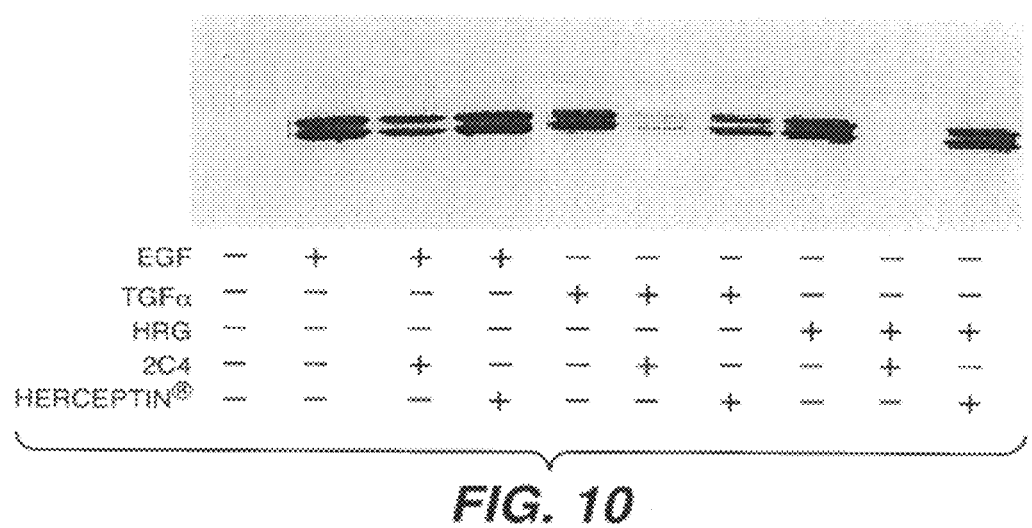
FIG. 10 depicts the effect of monoclonal antibody 2C4 or HERCEPTIN® on EGF, TGF-α, or HRG-mediated activation of mitogen-activated protein kinase (MAPK).

As shown in FIG. 10, monoclonal antibody 2C4 significantly blocks EGF, TGF-α and HRG mediated activation of MAPK to a greater extent than HERCEPTIN®. These data suggest that monoclonal antibody 2C4 binds to a surface of ErbB2 that is used for its association with either EGFR or ErbB3 and thus prevents the formation of the signaling receptor complex.

Monoclonal antibody 2C4 was also shown to inhibit heregulin (HRG)-dependent Akt activation. Activation of the PI3 kinase signal transduction pathway is important for cell survival (Carraway et al. *J. Biol. Chem.* 270: 7111-6 (1995)). In tumor cells, PI3 kinase activation may play a role in the invasive phenotype (Tan et al. *Cancer Research.* 59: 1620-1625, (1999)). The survival pathway is primarily mediated by the serine/threonine kinase AKT (Bos et al. *Trends Biochem Sci.* 20: 441-442 (1995). Complexes formed between ErbB2 and either ErbB3 or EGFR can initiate these pathways in response to heregulin or EGF, respectively (Olayioye et al. *Mol. & Cell. Biol.* 18: 5042-51 (1998); Karunagaran et al., *EMBO Journal.* 15: 254-264 (1996); and Krymskaya et al. *Am. J. Physiol.* 276: L246-55 (1999)). Incubation of MCF7 breast cancer cells with 2C4 inhibits heregulin-mediated AKT activation. Moreover, the basal level of AKT activation present in the absence of heregulin addition is further reduced by the addition of 2C4. These data suggest that 2C4 may inhibit ErbB ligand-activation of PI3 kinase and that this inhibition may lead to apoptosis. The increased sensitivity to apoptosis may manifest in a greater sensitivity of tumor cells to the toxic effects of chemotherapy.

Thus, monoclonal antibody 2C4 inhibits ligand initiated ErbB signaling through two major signal transduction pathways—MAP Kinase (a major proliferative pathway) and PI3 kinase (a major survival/anti-apoptotic pathway).

EXAMPLE 5 rhuMAb 2C4 for Treating Cancer-Associated Pain

A 43 years old male patient diagnosed with liposarcoma and receiving chemotherapy for two years was hospitalized with a deep wound in the left leg, requiring opiate analgesia prior to packing. The size of the tumor lesion was 6.6 cm. After two cycles of treatment with monoclonal antibody 2C4 (10 mg/kg), the patient could be wound packed without the administration of any additional analgesic agent. The tumor itself did not respond to 2C4 antibody treatment, but 2C4 exhibited analgesic activity.

EXAMPLE 6 rhuMAb 2C4 for Treating Pain Associated with Androgen-Independent Prostate Cancer Patients diagnosed with hormone-resistant (androgen-independent) prostate cancer with bony metastasis, which had progressed after taxane-based chemotherapy, were treated with rhuMAb 2C4. All patients recorded a Present Pain Intensity Score of 1 or more on a 6 point scale (McGill Pain Index) prior to starting rhuMAb 2C4 administration, where 0=no pain
1=mild pain
2=discomforting pain
3=distressing pain
4=horrible pain
5=excruciating pain.

The analgesia intake of the patients was measured using a daily diary. One dose of a non-steroidal analgesic agent was assigned a score of 1, one 10-mg dose of morphine or an equivalent dose of another opiate analgesic was assigned a score of 2.

rhuMAb 2C4 was administered starting with a 840 mg loading bolus dose followed by a 420 mg intravenous (i.v.) dose every three weeks.

One patient had a fall in pain score from 3 to 1, with modest reduction in analgesia requirement. This effect lasted for 24 weeks. The patient showed a reduction in the rate of rise of PSA, but no reduction in absolute value.

One patient had a stable pain score of 2, but stopped all analgesia. The effect is ongoing at 24 weeks, despite progression of PSA.

One patient showed an initial improvement in pain (score was reduced from 2 to 1) with more than 50% reduction in analgesia requirement. The treatment had no effect on the PSA of the patient. The effect on pain lasted for 6 weeks, then the disease progressed and pain increased.

The data show that rhuMAb 2C4 was able to reduce and stabilize the pain of patients even when prostate cancer was not in remission or continued to progress.

What is claimed is:

1. A method of treating cancer related pain comprising administering to a patient diagnosed with cancer-related pain an ErbB2 antagonist in a dose confirmed to reduce or eliminate the pain or the analgesia requirement of the patient, wherein the cancer continues to grow during said treatment and administration is continued during progression of the cancer, and wherein said ErbB2 antagonist blocks the binding of recombinant humanized monoclonal antibody 2C4 (rhuMAb 2C4) to ErbB2.

2. The method of claim 1 wherein pain is measured by a pain score or quality of life score reflective of pain.

3. The method of claim 2 wherein pain is measured by the McGill Pain Index on a six point scale of 0 to 5.

4. The method of claim 2 wherein pain is measured using a visual analog scale of 0-100 reflective of the subjective feeling of pain of the patient.

5. The method of claim 1 wherein analgesia requirement is measured using an analgesia score.

6. The method of claim 5 wherein one dose of a non-steroidal analgesic agent corresponds to an analgesia score of 1, and one 10 mg dose of morphine, or an equivalent dose of another opiate analgesic agent corresponds to an analgesia score of 2.

7. The method of claim 1 wherein pain is monitored daily.

8. The method of claim 1 wherein analgesia requirement is monitored daily.

9. The method of claim 1 wherein the antagonist is an antibody that binds ErbB2.

10. The method of claim 9 wherein the antibody blocks ligand activation of an ErbB.

11. The method of claim 9 wherein the antibody blocks formation of an ErbB heterodimer.

12. The method of claim 9 wherein the antibody comprises monoclonal antibody 2C4 or humanized 2C4.

13. The method of claim 9 wherein the antibody is not conjugated with a cytotoxic agent.

14. The method of claim 9 wherein the antibody is conjugated with a cytotoxic agent.

15. The method of claim 9 wherein the antibody is an antibody fragment.

16. The method of claim 15 wherein the antibody fragment is a Fab fragment.

17. The method of claim 15 wherein the antibody fragment is not conjugated with a cytotoxic agent.

18. The method of claim 15 wherein the antibody fragment is conjugated with a cytotoxic agent.

19. The method of claim 1 wherein the pain is chronic pain.

20. The method of claim 19 wherein the chronic pain is selected from the group consisting of nociceptive pain, neuropathic pain and psychogenic pain.

21. The method of claim 20 wherein the pain is nociceptive pain.

22. The method of claim 1 wherein the cancer expresses ErbB2.

23. The method of claim 1 or claim 22 wherein the cancer is metastatic cancer.

24. The method of claim 23 wherein the pain is associated with cancer metastasis.

25. The method of claim 23 wherein the metastasis is bone metastasis.

26. The method of claim 1 or claim 22 wherein the cancer is prostate cancer.

27. The method of claim 1 or claim 22 wherein the cancer is selected from the group consisting of breast cancer, ovarian cancer, prostate cancer, pancreatic cancer, squamous cell cancer, lung cancer, cancer of the peritoneum, hepatocellular cancer, gastric cancer, glioblastoma, cervical cancer, liver cancer, bladder cancer, hepatoma, colon cancer, rectal cancer, colorectal cancer, endometrial or uterine carcinoma, salivary gland carcinoma, kidney cancer, vulval cancer, thyroid cancer, hepatic carcinoma, anal carcinoma, penile carcinoma, and head and neck cancer.

28. The method of claim 27 wherein the cancer is prostate cancer.

29. The method of claim 28 wherein the cancer is androgen independent prostate cancer.

30. A method for treating cancer-related pain, comprising administering to a patient diagnosed with cancer-related pain an effective amount of a recombinant humanized monoclonal antibody 2C4 (rhuMAb 2C4), wherein the cancer is not in remission or continues to grow during said treatment.

31. The method of claim 30 wherein the cancer is not in remission during said treatment.

32. The method of claim 30 wherein the cancer continues to grow during said treatment.

33. The method of claim 30 wherein the cancer is selected from the group consisting of breast cancer, ovarian cancer, prostate cancer, pancreatic cancer, squamous cell cancer, lung cancer, cancer of the peritoneum, hepatocellular cancer, gastric cancer, glioblastoma, cervical cancer, liver cancer, bladder cancer, hepatoma, colon cancer, rectal cancer, colorectal cancer, endometrial or uterine carcinoma, salivary gland carcinoma, kidney cancer, vulval cancer, thyroid cancer, hepatic carcinoma, anal carcinoma, penile carcinoma, and head and neck cancer.

34. The method of claim 33 wherein the cancer is prostate cancer.

35. The method of claim 34 wherein the cancer is androgen independent prostate cancer.

36. The method of claim 34 wherein the patient's PSA shows no reduction during treatment.

37. The method of claim 34 wherein the patient's PSA becomes elevated during treatment.

38. The method of claim 30 wherein the cancer is metastatic cancer.

39. The method of claim 38 wherein the metastasis is soft tissue metastasis.

40. The method of claim 38 wherein the metastasis includes bone metastasis.

41. The method of claim 30 wherein the antibody is an antibody fragment.

42. The method of claim 41 wherein the antibody fragment is a Fab fragment.

43. The method of claim 41 wherein the antibody fragment is not conjugated with a cytotoxic agent.

44. The method of claim 41 wherein the antibody fragment is conjugated with a cytotoxic agent.

45. The method of claim 30 wherein the antibody is not conjugated with a cytotoxic agent.

46. The method of claim 30 wherein the antibody is conjugated with a cytotoxic agent.

* * * * *